(12) United States Patent
Lee et al.

(10) Patent No.: US 9,814,741 B2
(45) Date of Patent: Nov. 14, 2017

(54) METHODS RELATING TO DNA-SENSING PATHWAY RELATED CONDITIONS

(71) Applicant: THE GENERAL HOSPITAL CORPORATION, Boston, MA (US)

(72) Inventors: Mark Nackyoung Lee, Cambridge, MA (US); Nir Hacohen, Brookline, MA (US)

(73) Assignee: The General Hospital Corporation, Boston, MA (US)

( * ) Notice: Subject to any disclaimer, the term of this patent is extended or adjusted under 35 U.S.C. 154(b) by 0 days.

(21) Appl. No.: 14/676,933

(22) Filed: Apr. 2, 2015

(65) Prior Publication Data
US 2015/0202223 A1 Jul. 23, 2015

Related U.S. Application Data

(63) Continuation-in-part of application No. PCT/US2013/063025, filed on Oct. 2, 2013.

(60) Provisional application No. 61/708,719, filed on Oct. 2, 2012.

(51) Int. Cl.

| | |
|---|---|
| *C12N 15/113* | (2010.01) |
| *A61K 31/713* | (2006.01) |
| *C12Q 1/68* | (2006.01) |
| *A61K 31/192* | (2006.01) |
| *A61K 31/395* | (2006.01) |
| *A61K 31/35* | (2006.01) |
| *A61K 31/506* | (2006.01) |
| *A61K 31/56* | (2006.01) |
| *A61K 31/635* | (2006.01) |
| *A61K 39/00* | (2006.01) |

(52) U.S. Cl.
CPC .......... *A61K 31/713* (2013.01); *A61K 31/192* (2013.01); *A61K 31/35* (2013.01); *A61K 31/395* (2013.01); *A61K 31/506* (2013.01); *A61K 31/56* (2013.01); *A61K 31/635* (2013.01); *A61K 39/00* (2013.01); *C12Q 1/6876* (2013.01); *C12Q 1/6883* (2013.01); *A61K 2039/53* (2013.01); *C12Q 2600/118* (2013.01); *C12Q 2600/156* (2013.01); *C12Q 2600/158* (2013.01); *C12Q 2600/16* (2013.01)

(58) Field of Classification Search
CPC ..... A61K 31/713; A61K 39/00; C12N 15/111
See application file for complete search history.

(56) References Cited

U.S. PATENT DOCUMENTS

| | | | | |
|---|---|---|---|---|
| 2004/0259247 A1* | 12/2004 | Tuschl | ........... | A61K 48/00 435/375 |
| 2007/0071675 A1 | 3/2007 | Wu et al. | | |
| 2011/0230444 A1 | 9/2011 | Garcia-Echeverria et al. | | |
| 2012/0238540 A1* | 9/2012 | Holcomb | ........... | C07D 239/42 514/210.18 |

FOREIGN PATENT DOCUMENTS

WO    2011/046970    4/2011

OTHER PUBLICATIONS

Lenert (Clinic. & Exper. Immunol. (2010) 161:208-222).*
D'Arrigo et al. (Dev. Med. Child Neur. (2008) 50:631-634).*
Seissler et al. (Transpl. Immunol. (2012) 27:157-161).*
Clark et al. (Biochem. Journal (Jan. 2011) 434, 93-104).*
International Search Report and Written Opinion of the International Searching Authority dated dated Jan. 30, 2014, which issued during prosecution of International Application No. PCT/US2013/063025.
Clark, et al. "Novel cross-talk within the IKK family controls innate immunity" Biochem J. 434:93-104, 2011.
Ostman, et al. "Protein-tyrosine phosphatases and cancer" Nature Reviews Cancer 6:307-320, 2006.
Smith, et al. "Targeting CDC37: An alternative, kinase directed strategy for disruption of oncogenic chaperoning" Cell Cycle 8(3):362-372, 2009.
Szoor, et al. "Protein tyrosine phosphatase TbPTP1: a molecular switch controlling life cycle differentiation in trypanosomes" The Journal of Cell Biology 175(2):293-303, Oct. 2006.
Yang, et al. "Hsp90 Regulates Activation of Interferon Regulatory Factor 3 and TBK-1 Stabilization in Sendai Virus-infected Cells" Molecular Biology of the Cells 17:1461-1471, Mar. 2006.
European Extended Search Report dated Oct. 10, 2016, which issued during prosecution of Application No. EP13844520.
Supplementary Partial European Search Report dated dated May 31, 2016, which issued during prosecution of Application No. EP13844520.

* cited by examiner

Primary Examiner — J. E. Angell
(74) Attorney, Agent, or Firm — Vedder Price P.C.; Thomas J Kowalski; Deborah L. Lu

(57) ABSTRACT

The invention provides, inter alia, methods for modulating DNA sensing pathways and the innate immune responses downstream of such pathways. The invention contemplates methods for down-regulating this pathway and/or the downstream innate immune response. The invention further contemplates methods for up-regulating this pathway and/or the downstream innate immune response.

20 Claims, 31 Drawing Sheets

Fig. 11A  Fig. 11B

METHODS RELATING TO DNA-SENSING PATHWAY RELATED CONDITIONS

RELATED APPLICATIONS AND INCORPORATION BY REFERENCE

This application is a continuation-in-part application of international patent application Serial No. PCT/US2013/063025 filed Oct. 2, 2013, which published as PCT Publication No. WO 2014/055624 A1 on Apr. 10, 2014, which claims benefit of U.S. provisional patent application Ser. No. 61/708,719 filed Oct. 2, 2012.

FEDERAL FUNDING LEGEND

This invention was made with government support under grant number DP2 OD002230 awarded by the National Institutes of Health. The government has certain rights in this invention.

The foregoing applications, and all documents cited therein or during their prosecution ("appln cited documents") and all documents cited or referenced in the appln cited documents, and all documents cited or referenced herein ("herein cited documents"), and all documents cited or referenced in herein cited documents, together with any manufacturer's instructions, descriptions, product specifications, and product sheets for any products mentioned herein or in any document incorporated by reference herein, are hereby incorporated herein by reference, and may be employed in the practice of the invention. More specifically, all referenced documents are incorporated by reference to the same extent as if each individual document was specifically and individually indicated to be incorporated by reference.

FIELD OF THE INVENTION

The invention relates to a method of modulating an innate immune response by targeting the DNA sensing pathway.

BACKGROUND OF INVENTION

The innate immune system detects viral infection primarily by recognizing viral nucleic acids inside an infected cell. In the case of retroviruses, which are RNA viruses that replicate via a DNA intermediate, the reverse transcribed DNA is believed to be recognized during entry into a host cell by a cytoplasmic DNA sensor(s) that triggers type I IFN production. This latter response has been observed in cells that lack the endoplasmic reticulum (ER)-associated 3'->5' exonuclease, TREX1. When TREX1 is present, it can degrade the viral DNA before sensing occurs.

A similar fate appears to be the case with self DNA from the host cell, as deficiency in TREX1 leads to the accumulation of endogenous retroelements and genomic DNA in the cytoplasm, causing aberrant over-activation of the DNA-sensing pathway and subsequent initiation of autoimmune disease. Currently treatments target the symptoms of such autoimmune diseases. Accordingly, there is a need for a more complete understanding of the DNA sensing pathway to develop targeted treatments.

Citation or identification of any document in this application is not an admission that such document is available as prior art to the present invention.

SUMMARY OF INVENTION

The invention relates broadly to monitoring and modulation of DNA sensing pathways and concomitant innate immune responses for diagnostic and therapeutic purposes. The invention is premised in part on a more complete understanding of the mechanisms involved in DNA sensing pathways which in turn has led to a more complete understanding of the mechanism involved in DNA-triggered innate immune response induction.

Using an integrative approach that combined quantitative proteomics, genomics and small molecule perturbations, novel components of the DNA sensing pathway were identified. These novel components include ABCF1, HSP90, and CDC37. TBK1 was also found to be involved in the DNA sensing pathway. The invention therefore provides methods for modulating the DNA sensing pathway and related methods for modulating the innate immune response that results from this pathway. In some instances, the method provided herein down-regulate the DNA sensing pathway and the downstream innate immune response. Such down-regulation is useful in the treatment of autoimmune disorders. Of particular interest are Aicardi-Goutieres syndrome (AGS), familial chilblain lupus (FCL), and retinal vasculopathy with cerebral leukodystrophy (RVCL). Accordingly, some aspects of the invention provide methods for treating subjects having any of these autoimmune disorders by modulating the DNA sensing pathway. More specifically, the invention contemplates treatment of these conditions using inhibitors of ABCF1, HSP900, and/or CDC37. Certain embodiments of the invention contemplate the use of inhibitors of TBK1, optionally in combination with inhibitors of ABCF1, HSP900, and CDC37.

The invention also provides methods for up-regulating the DNA-triggered innate immune response. It was found unexpectedly that inhibition of other components of the DNA sensing pathway led to an increased innate immune response. In particular, inhibition of PTPN1 and PPP6C, individually or together, increased the innate immune response. Such up-regulation is useful in the treatment of conditions that would benefit from a heightened immune response such as but not limited to infections such as viral infections and cancers. Additionally, such up-regulation is useful in the context of DNA and RNA vaccination in order to enhance the immune response to the antigen of interest.

The invention provides insight into the upstream events involved in DNA-triggered immune response induction. In this way, it identifies factors involved in these upstream events that can be targeted to prevent or reduce the underlying immune response. This is in contrast to the amelioration of symptoms resulting from the underlying immune response. Accordingly, certain methods of the method are directed towards avoiding or reducing the immune response rather than dampening the symptoms of the immune response.

Thus, in one aspect, the invention provides a method comprising measuring presence or level of a DNA sensing pathway marker in a subject, and administering to a subject having an aberrant level of the DNA sensing pathway marker an effective amount of an active agent selected from the group consisting of an ABCF1 inhibitor, an HSP900 inhibitor, and a CDC37 inhibitor, or a combination thereof.

In another aspect, the invention provides a method comprising administering to a subject, identified as having an aberrant level of a DNA sensing pathway marker, an effective amount of an active agent selected from the group consisting of an ABCF1 inhibitor, an HSP900 inhibitor, and a CDC37 inhibitor, or a combination thereof.

In some embodiments, the method further comprises administering a TBK1 inhibitor to the subject. When the active agents administered together, in some embodiments, the result is a synergistic effect (i.e., the effect is more than additive).

In some embodiments, the DNA sensing pathway marker is aberrant interferon-stimulated gene (ISG) expression, a mutation in Trex1, Dnase1, Dnase2, Fen1 (DnaseIV), RnaseH2, SAMHD1, or another nuclease, reduced expression of Trex1, Dnase1, Dnase2, Fen1 (DnaseIV), RnaseH2, SAMHD1, or another nuclease, or reduced activity of Trex1, Dnase1, Dnase2, Fen1 (DnaseIV), RnaseH2, SAMHD1, or another nuclease.

Aberrant (ISG) expression may be mRNA expression or protein expression and thus may be measured at the mRNA level and/or the protein level. Aberrant ISG expression is an expression of an interferon-stimulated gene (ISG) that is abnormal. Such expression is above the normal expression level of ISG. In some instances, that abnormal level is simply presence of ISG expression where in a normal setting such expression is absent. ISGs are known in the art as evidenced by de Veer et al. J Leukoc Biol, 2001, 69(6):912-20. Examples include IRF1, C6orf150 (also known as MB21D1), HPSE, RIG-I (also known as DDX58), MDA5 (also known as IFIH1) and IFITM3, DDX60, IFI44L, IFI6, IFITM2, MAP3K14, MOV10, NAMPT (also known as PBEF1), OASL, RTP4, TREX1 and UNC84B (also known as SUN2).

In some embodiments, the active agent is an ABCF1 inhibitor. The ABCF1 inhibitor may be an siRNA or other inhibitor that down-regulates or prevents translation of the ABCF1 protein. An example is the siRNA sc-140760. The ABCF1 inhibitor may act on the ABCF1 protein and may interfere with the ability of ABCF1 to bind to DNA.

In some embodiments, the active agent is an HSP900 inhibitor. In some embodiments, the active agent is a CDC37 inhibitor. In some embodiments, the active agent is administered together with a TBK1 inhibitor. In some embodiments, a CDC37 inhibitor and an HSP900 inhibitor are used together (i.e., two separate and different active agents are administered to the subject). In some embodiments, an ABCF1 inhibitor is administered together with another inhibitor. In some embodiments, three inhibitors of different classes are administered to the subject (e.g., an HSP900 inhibitor, a CDC37 inhibitor, and a TBK1 inhibitor). In some embodiments, four inhibitors of different classes are administered to the subject (e.g., an HSP900 inhibitor, a CDC37 inhibitor, a TBK1 inhibitor, and an ABCF1 inhibitor).

In some embodiments, the ABCF1 inhibitor, the HSP900 inhibitor, the CDC37 inhibitor, and/or the TBK1 inhibitor is a small molecule. In some embodiments, the ABCF1 inhibitor, the HSP900 inhibitor, the CDC37 inhibitor, or the TBK1 inhibitor is an siRNA.

In some embodiments, the HSP900 inhibitor is 17-DMAG, 17-AAG, or geldanamycin. In some embodiments, the CDC37 inhibitor is celastrol. In some embodiments, the TBK1 inhibitor is BX795 or MRT67307.

In some embodiments, the active agent is administered prior to the onset of symptoms associated with an autoimmune disorder. In some embodiments, the active agent(s) is administered at regular intervals (or chronically) to the subject (e.g., daily, weekly, monthly) in order to prevent the onset or occurrence of the immune response. The active agent(s) may be administered more regularly during certain times, including for example when exposure to stimuli of the immune response is most prevalent.

Various of the foregoing embodiments apply to the following aspects of the invention.

In another aspect, the invention provides a method for treating a subject having Aicardi-Goutieres syndrome (AGS) comprising administering to said subject an effective amount of an ABCF1 inhibitor, an HSP900 inhibitor, or a CDC37 inhibitor, or a combination thereof.

In another aspect, the invention provides a method for treating a subject having familial chilblain lupus (FCL) comprising administering to said subject an effective amount of an ABCF1 inhibitor, an HSP900 inhibitor, or a CDC37 inhibitor, or a combination thereof.

In another aspect, the invention provides a method for treating a subject having retinal vasculopathy with cerebral leukodystrophy (RVCL) comprising administering to said subject an effective amount of an ABCF1 inhibitor, an HSP900 inhibitor, or a CDC37 inhibitor, or a combination thereof.

In some embodiments, the subject carries a mutation in Trex1. Dnase1. Dnase2, Fen1 (DnaseIV), RnaseH2, SAMHD1, or another nuclease, or manifests aberrant interferon-stimulated gene (ISG) expression or reduced expression of Trex1, Dnase1, Dnase2, Fen1 (DnaseIV), RnaseH2, SAMHD1 or another nuclease, or reduced activity of Trex1, Dnase1, Dnase2, Fen1 (DnaseIV), RnaseH2, SAMHD1, or another nuclease.

In another aspect, the invention provides a method for stimulating an immune response in a subject comprising administering to a subject an effective amount of a PTPN1 inhibitor, a PPP6C inhibitor, or a combination thereof. In some embodiments, the subject has a viral infection. In some embodiments, the viral infection is a retroviral infection. In some embodiments, the retroviral infection is an HIV infection. In some embodiments, the viral infection is an infection with a DNA virus. In some embodiments, the DNA virus is HSV. In some embodiments, the subject has cancer. In some embodiments, the PTPN1 inhibitor, or the PPP6C inhibitor, or a combination thereof is used in combination with a DNA vaccine. In some embodiments, the immune response is an innate immune response. In some embodiments, the PTPN1 inhibitor is 3-(3,5-Dibromo-4-hydroxy-benzoyl)-2-ethyl-benzofuran-6-sulfonicacid-(4-(thiazol-2-ylsulfamyl)-phenyl)-amide. The PTPN1 inhibitor may be an siRNA. The PPP6C inhibitor may be an siRNA.

Other advantages and novel features of the present invention will become apparent from the following detailed description of various non-limiting embodiments of the invention when considered in conjunction with the accompanying Figures. In cases where the present specification and a document incorporated by reference include conflicting and/or inconsistent disclosure, the present specification shall control. If two or more documents incorporated by reference include conflicting and/or inconsistent disclosure with respect to each other, then the document having the later effective date shall control.

Accordingly, it is an object of the invention to not encompass within the invention any previously known product, process of making the product, or method of using the product such that Applicants reserve the right and hereby disclose a disclaimer of any previously known product, process, or method. It is further noted that the invention does not intend to encompass within the scope of the invention any product, process, or making of the product or method of using the product, which does not meet the written description and enablement requirements of the USPTO (35 U.S.C. §112, first paragraph) or the EPO (Article 83 of the EPC), such that Applicants reserve the right and hereby disclose a disclaimer of any previously described product, process of making the product, or method of using the product.

It is noted that in this disclosure and particularly in the claims and/or paragraphs, terms such as "comprises", "comprised", "comprising" and the like can have the meaning attributed to it in U.S. Patent law; e.g., they can mean "includes", "included", "including", and the like; and that terms such as "consisting essentially of" and "consists essentially of" have the meaning ascribed to them in U.S. Patent law, e.g., they allow for elements not explicitly recited, but exclude elements that are found in the prior art or that affect a basic or novel characteristic of the invention. Nothing herein is intended as a promise.

These and other embodiments are disclosed or are obvious from and encompassed by, the following Detailed Description.

BRIEF DESCRIPTION OF DRAWINGS

The patent or application file contains at least one drawing executed in color. Copies of this patent or patent application publication with color drawing(s) will be provided by the Office upon request and payment of the necessary fee.

The following detailed description, given by way of example, but not intended to limit the invention solely to the specific embodiments described, may best be understood in conjunction with the accompanying drawings.

Figure 1A:
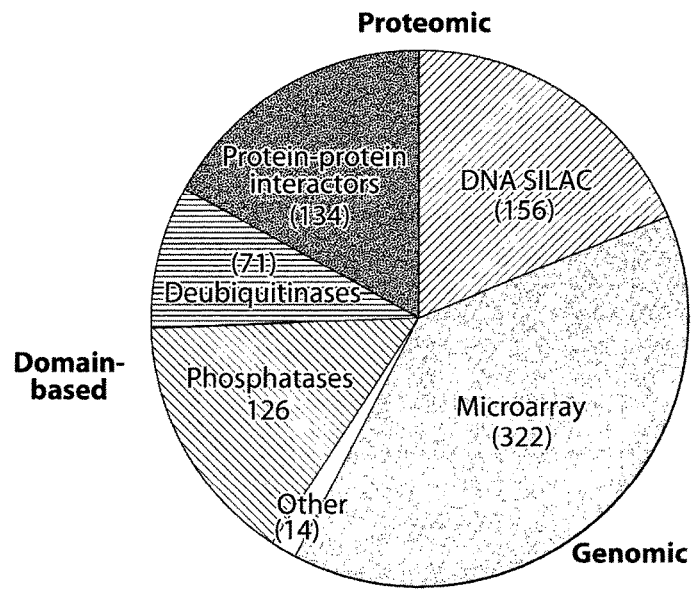
Figure 1B:
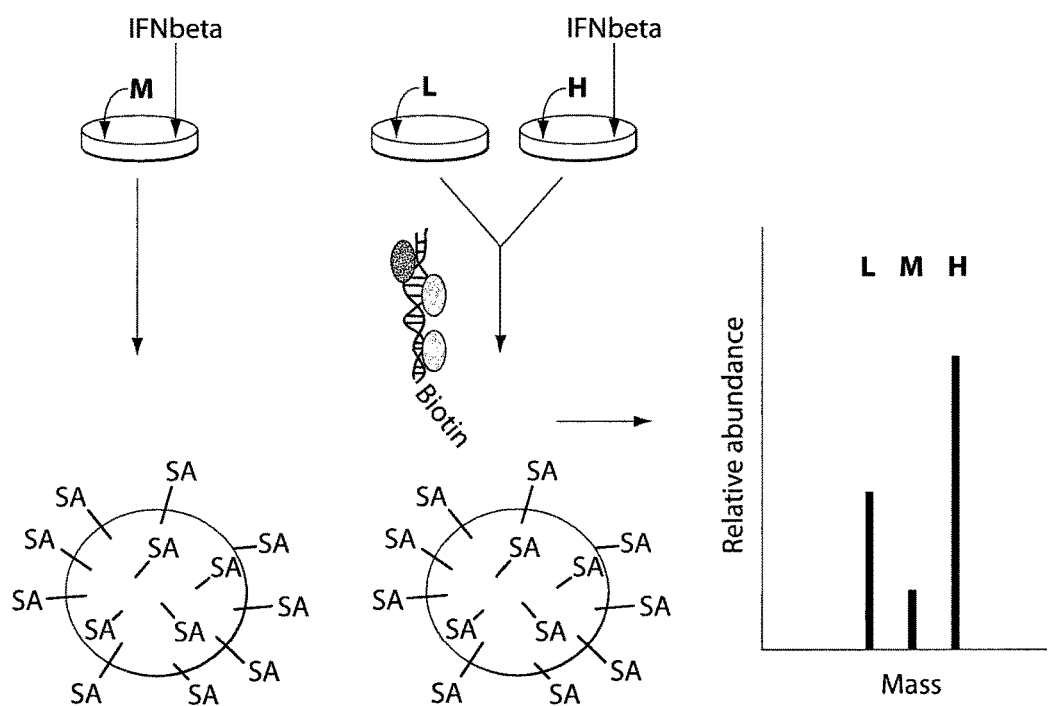
Figure 1C:
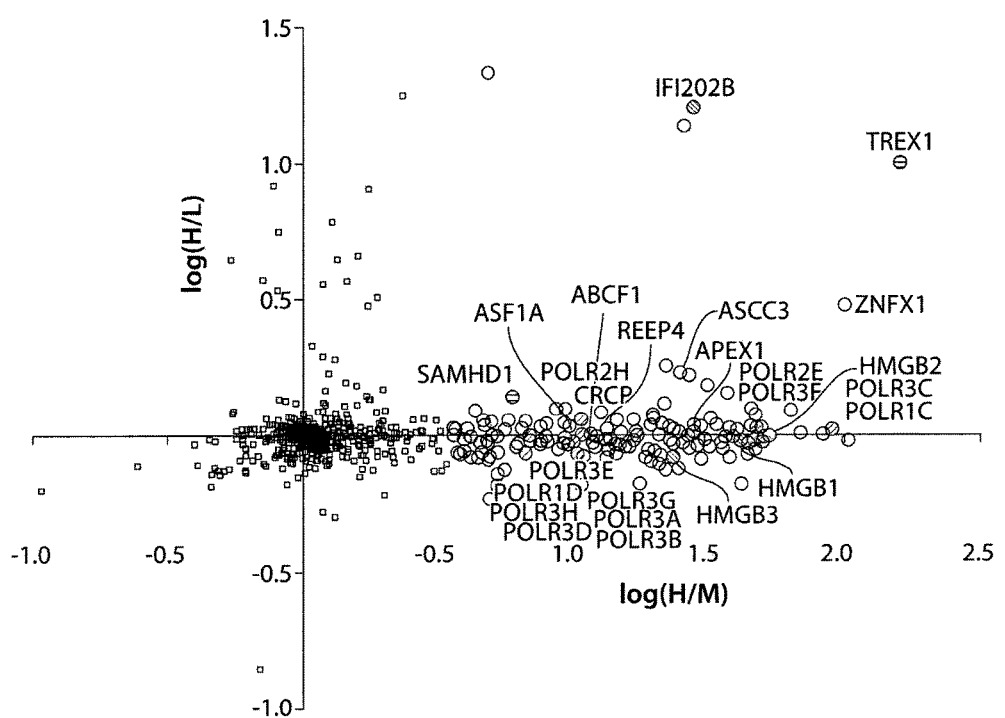
Figure 1D:
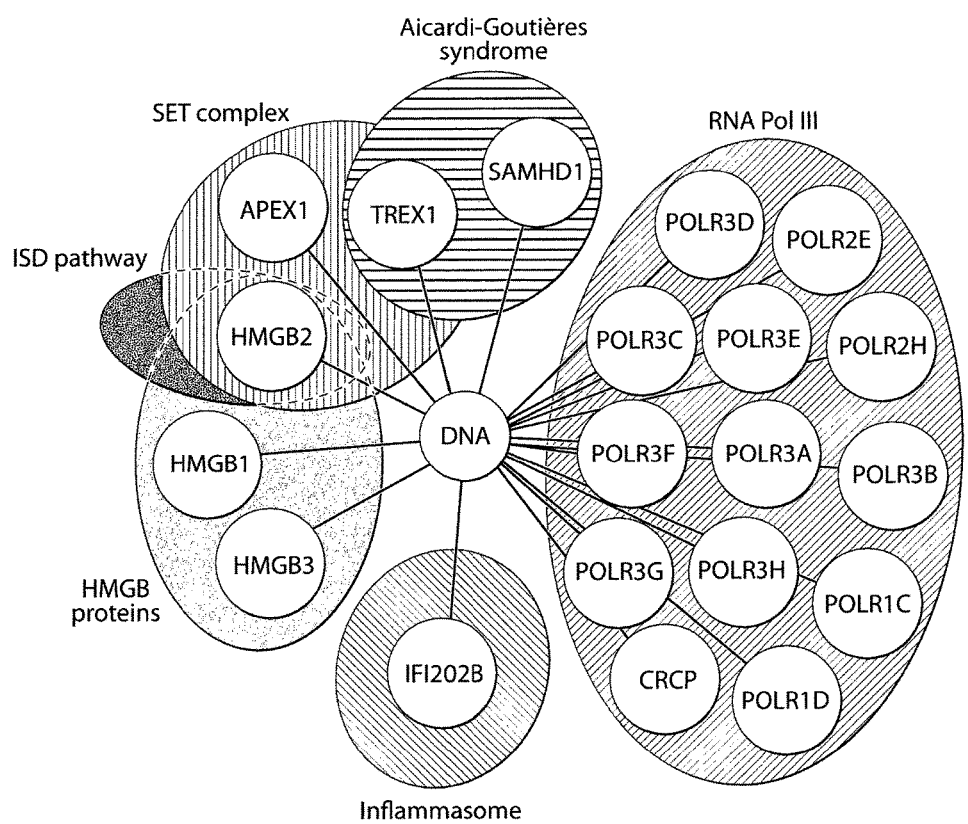

The accompanying Figures are not intended to be drawn to scale. For purposes of clarity, not every component may be labeled in every Figure. In the Figures:

FIG. 1A-D shows the generation of a candidate gene set by curation and quantitative proteomics. FIG. 1A show candidate genes from proteomic, genomic, and domain-based datasets hypothesized to contain unidentified ISD pathway components. FIG. 1B shows three-state SILAC (stable isotope labeling by amino acids in cell culture) used to label and quantitate peptides using mass spectrometry. FIG. 1C shows a graph of 184 proteins identified with SILAC ratios. FIG. 1D shows a plot of proteins identified as involved in the immune sensing of cytosolic DNA.

Figure 2A:
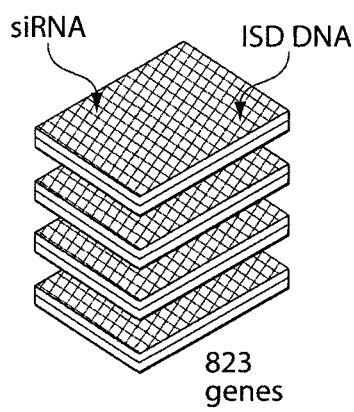
Figure 2A:
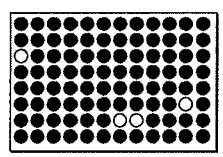
Figure 2B:
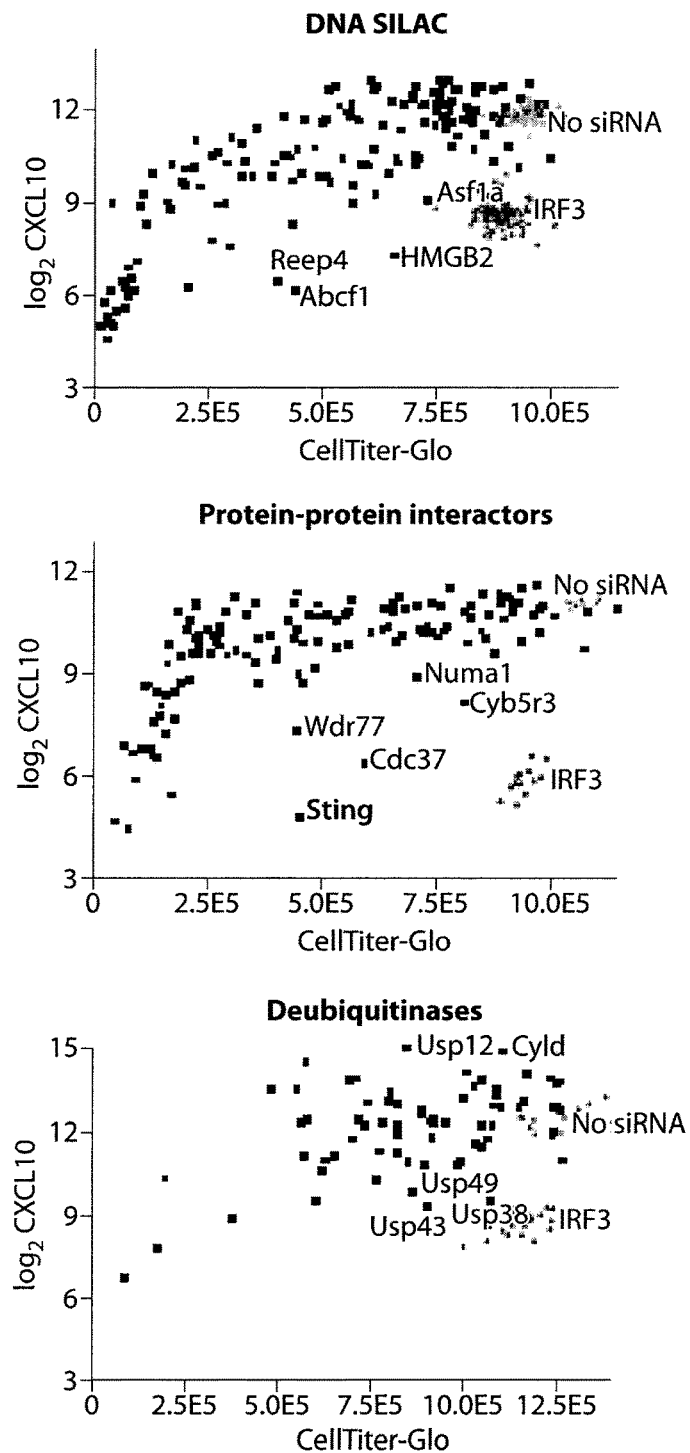
Figure 2C:
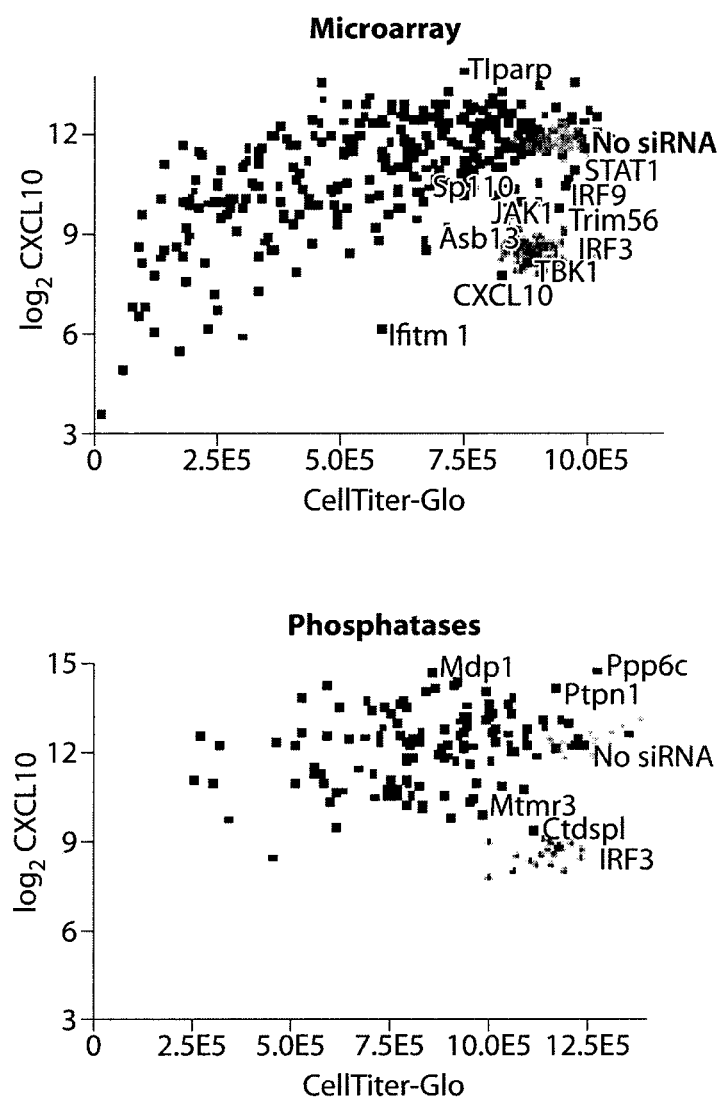
Figure 2D:
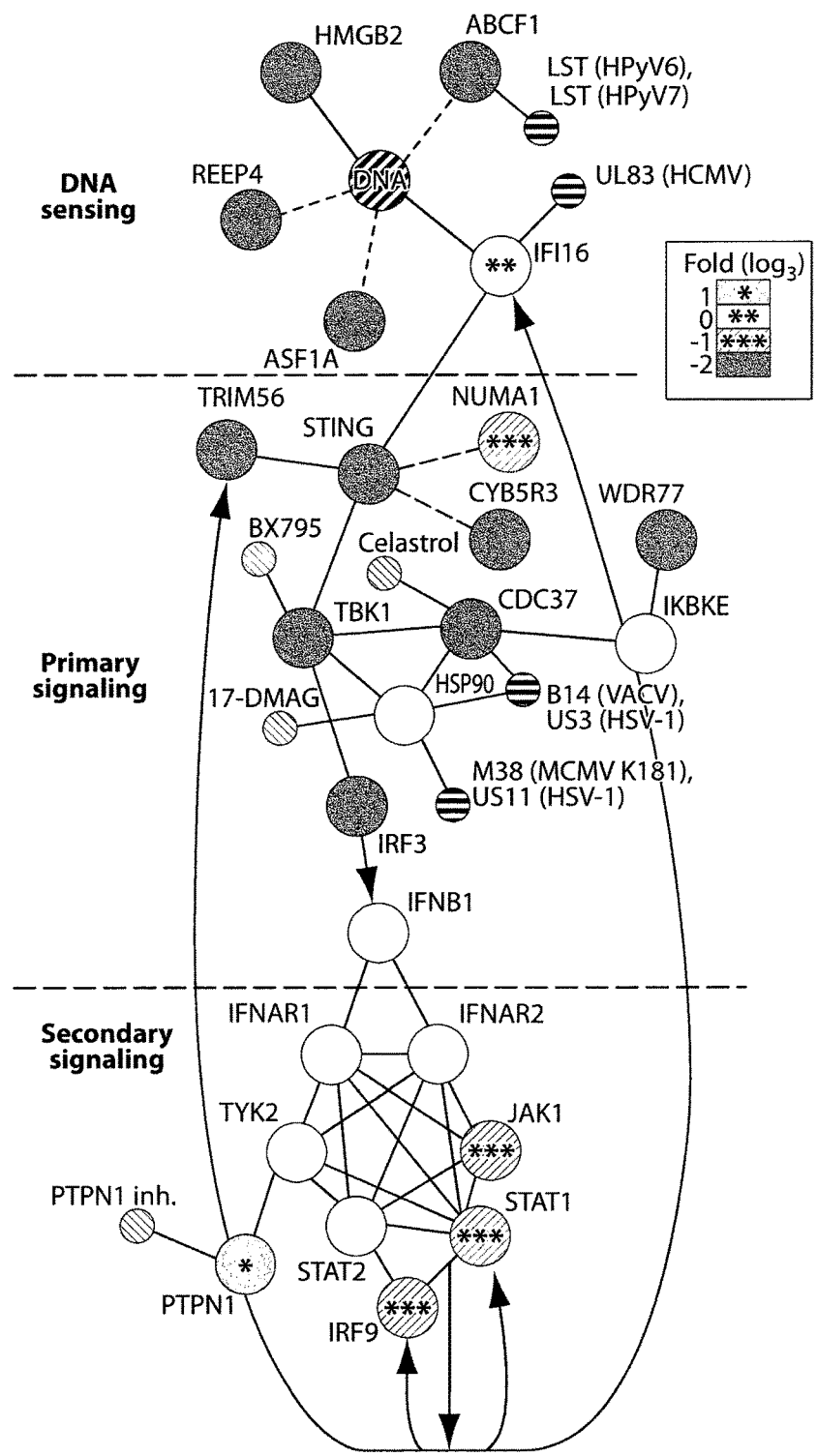

FIG. 2A-D shows high-throughput loss-of-function screening of candidates and network analysis. FIG. 2A shows an illustration of measured production of the IFN-inducible protein, CXCL10, by ELISA. FIG. 2B and 2C show graphs of the average of triplicate wells. FIG. 2D shows the expected positions for selected hits in the IDS pathway, found by bringing together information from the PPI datasets.

Figure 3A:
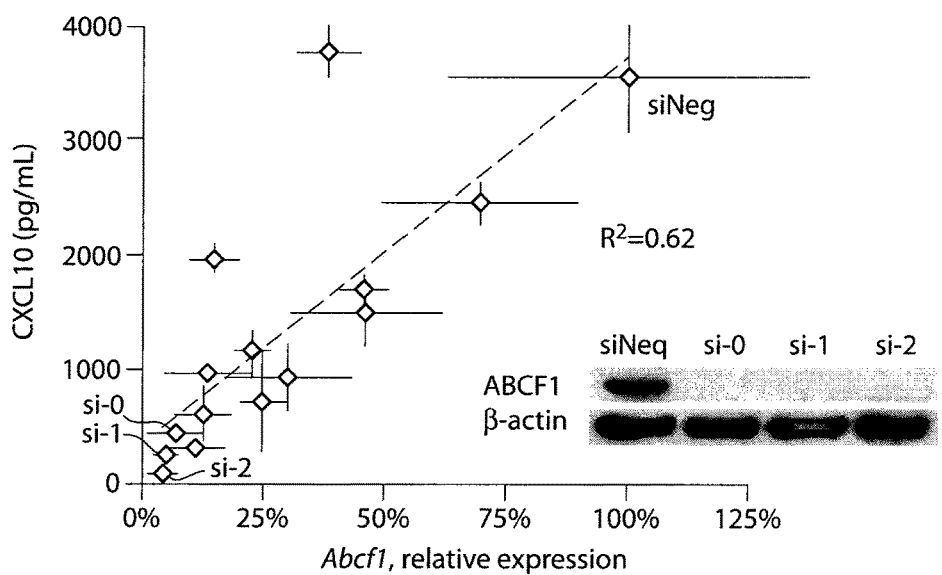
Figure 3B:
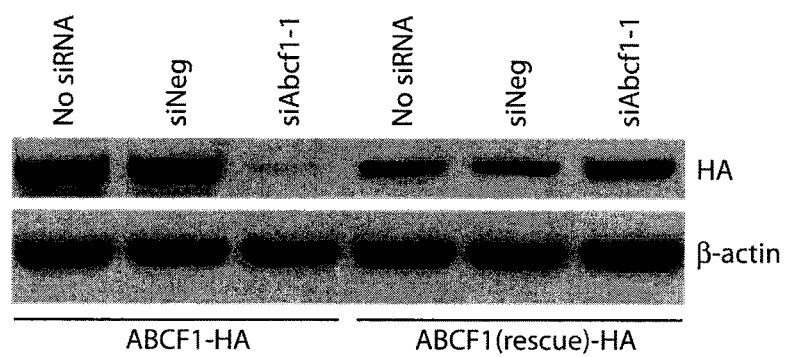
Figure 3C:
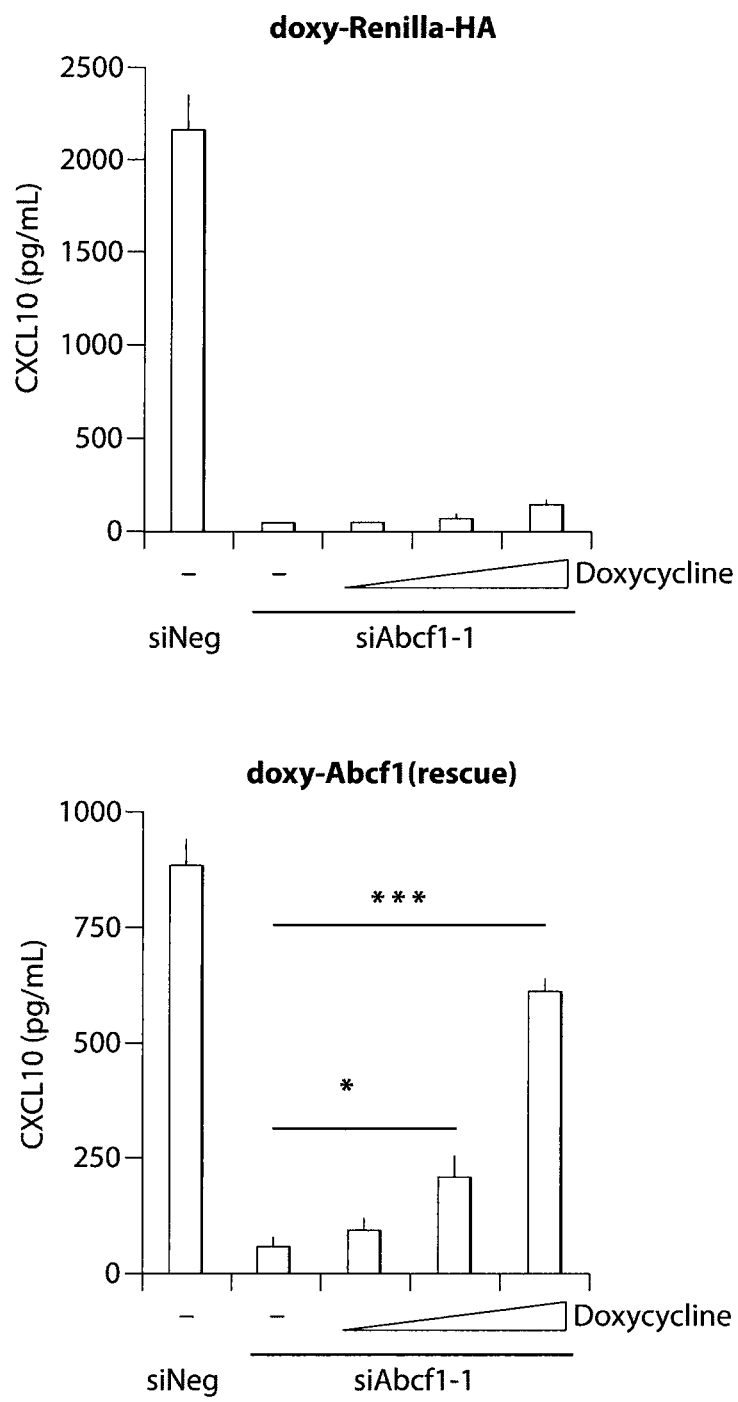

FIG. 3A-C shows validation by targeted knockout, cDNA rescue, and chemical inhibition. FIG. 3A is a graph showing that knockdown of Abcf1 correlated with CXCL1 induction ($R^2=0.62$), with the screening siRNA pool (si-0) and two other siRNAs (si-1 and -2) inhibiting both Abcf1 mRNA and protein expression and CXCL10 induction most strongly. FIG. 3B is an image demonstrating the created siRNA-resistant cDNA (Abcf1(rescue) gene. FIG. 3C shows that knockdown of Abcf1 reduced CXCL10 production by 14.9-fold ($P<0.01$) and expression of Abcf1(rescue) cDNA, but not of a *Renilla* cDNA control, significantly rescued this phenotype in a dose-dependent manner.

Figure 4A:
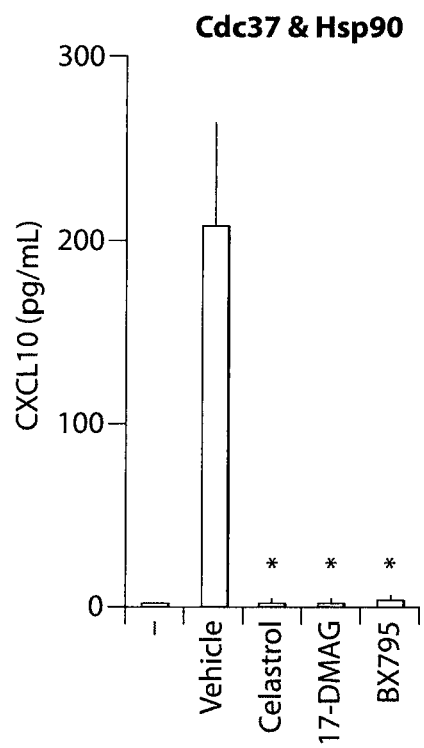
Figure 4B:
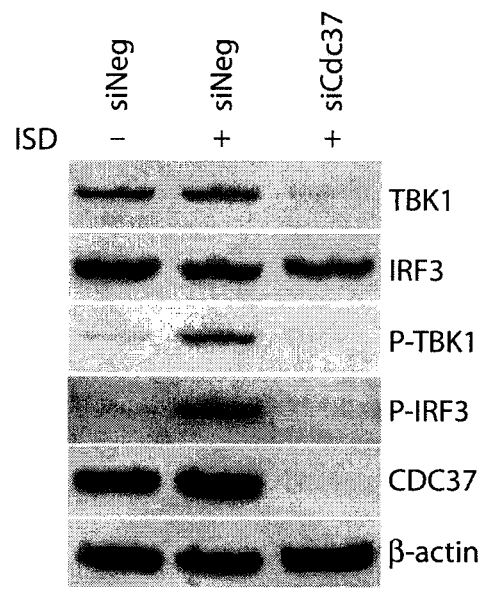
Figure 4C:
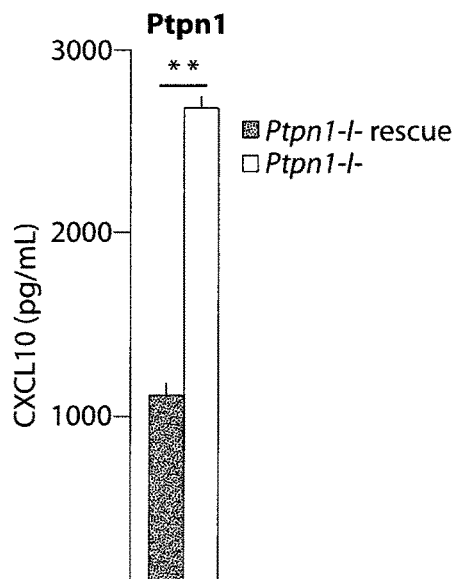
Figure 4D:
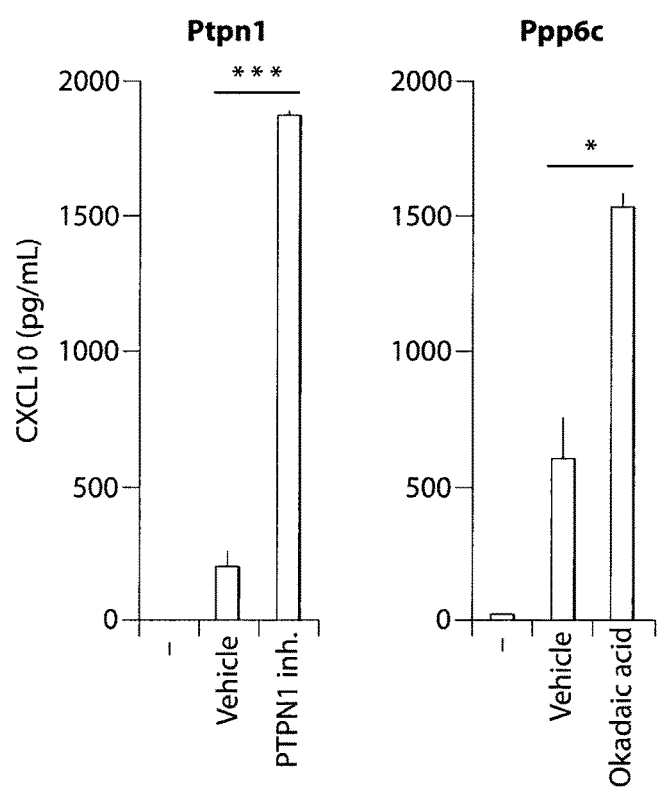

FIG. 4A-D shows targeting of screening hits by small molecule inhibitors. FIG. 4A is a graph showing treatment of murine or human cells with celastrol, a small molecule inhibitor of the CDC37-HSP900 interaction potently reduced Ifnb1 and CXCL10 induction. FIG. 4B is an image showing the effect of the knockdown of Cdc37. FIG. 4C is a graph showing CXCL10 production in treated MoDCs as measured by ELISA. * $P<0.05$, *** $P<0.001$ compared with vehicle control. FIG. 4D is two graphs showing CXCL10 production in MoDCs stimulated with ISD and treated with a small molecule inhibitor of PTPN1 or PPP6C.

Figure 5A:
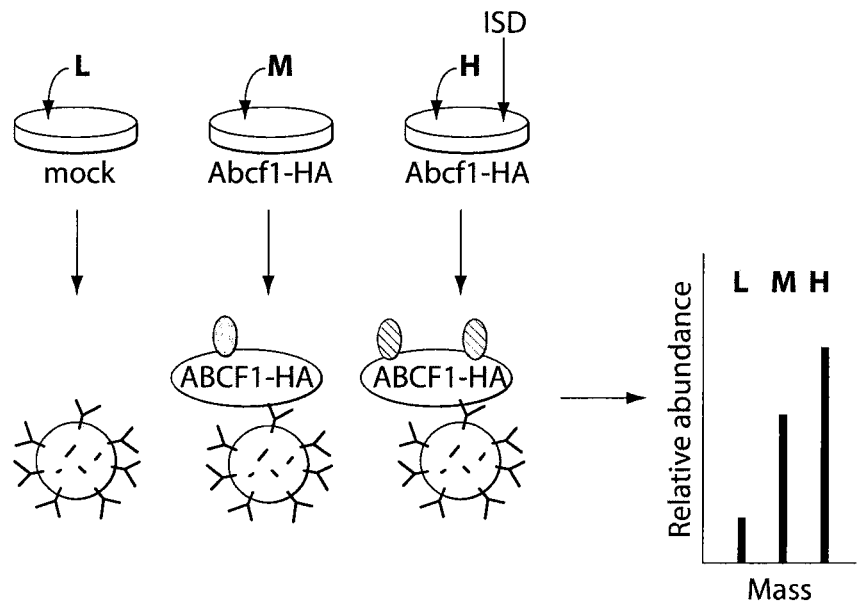
Figure 5A:
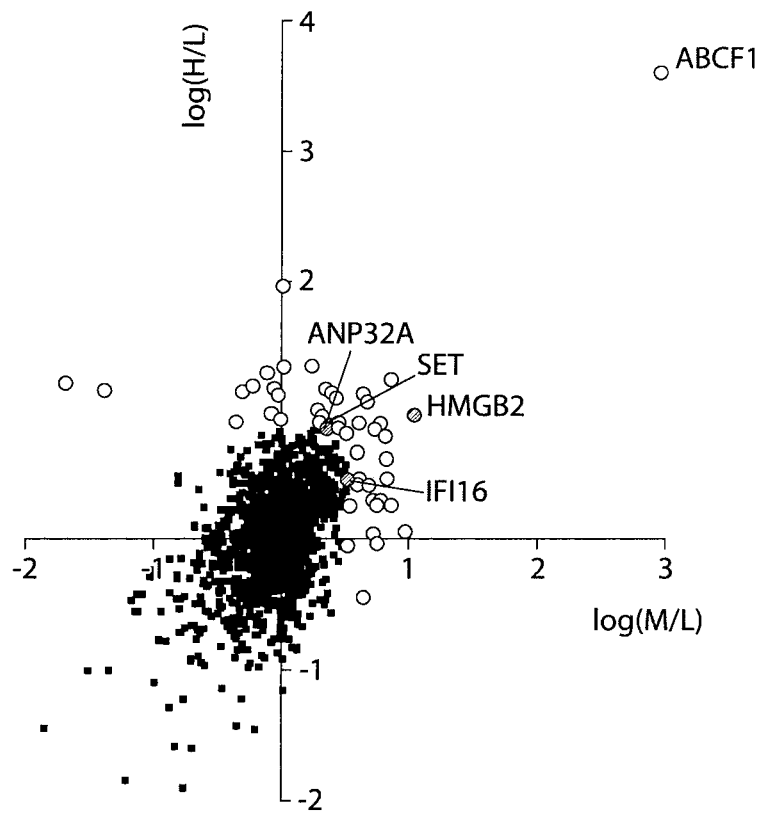
Figure 5B:
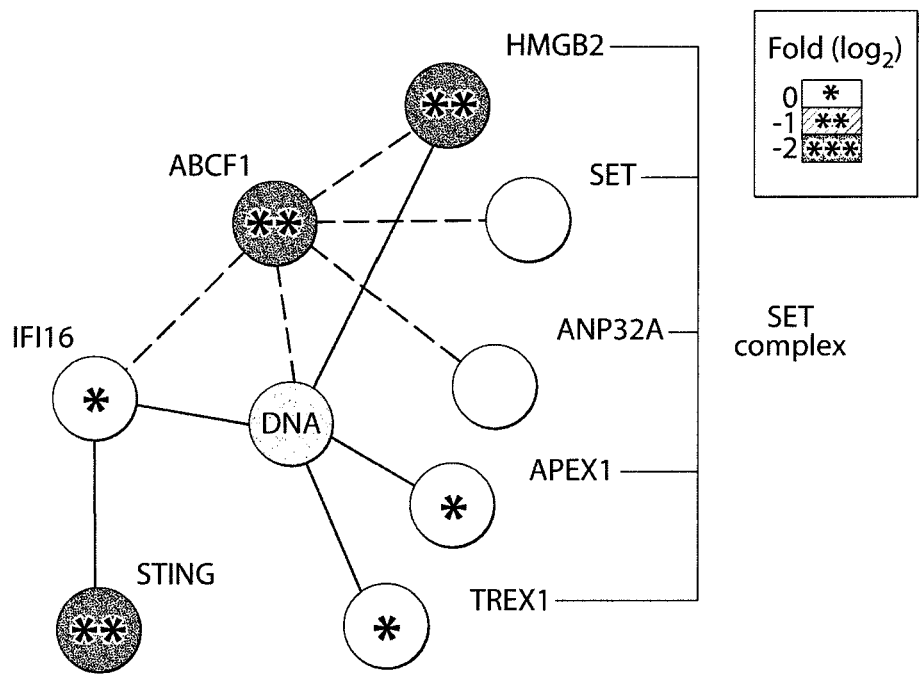
Figure 5C:
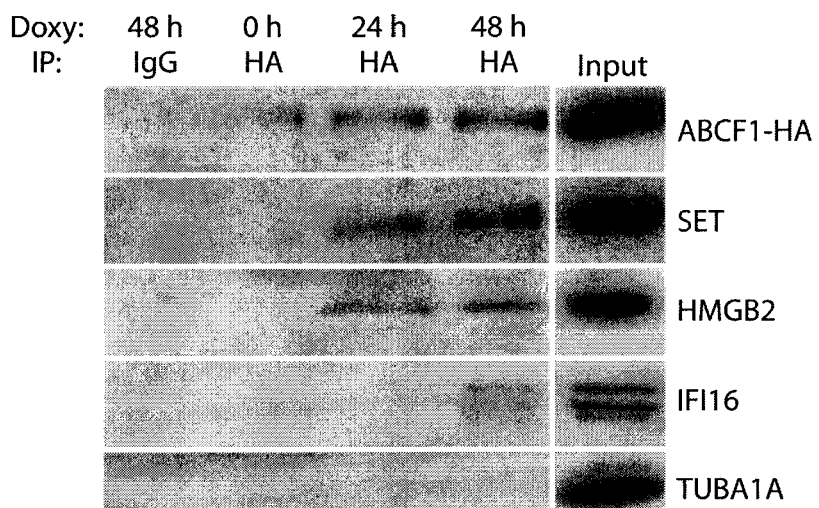
Figure 5D:
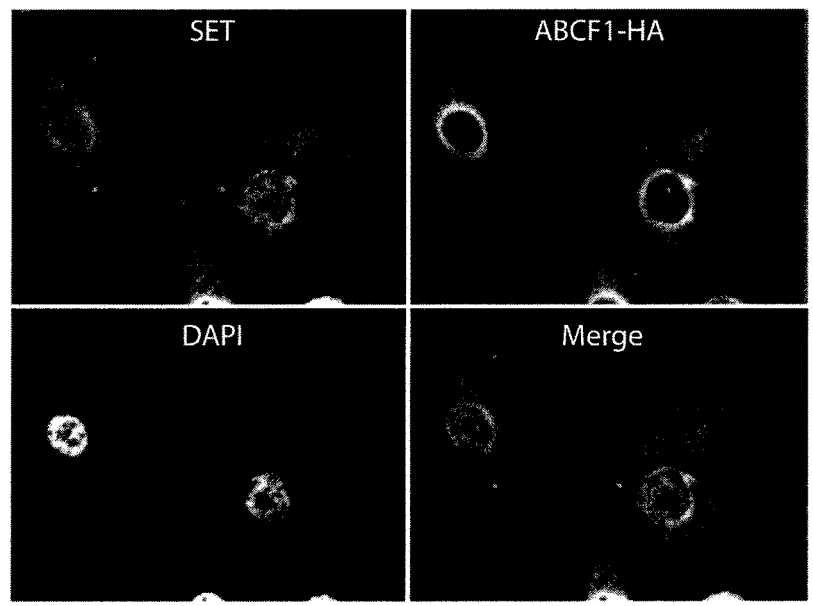
Figure 5E:
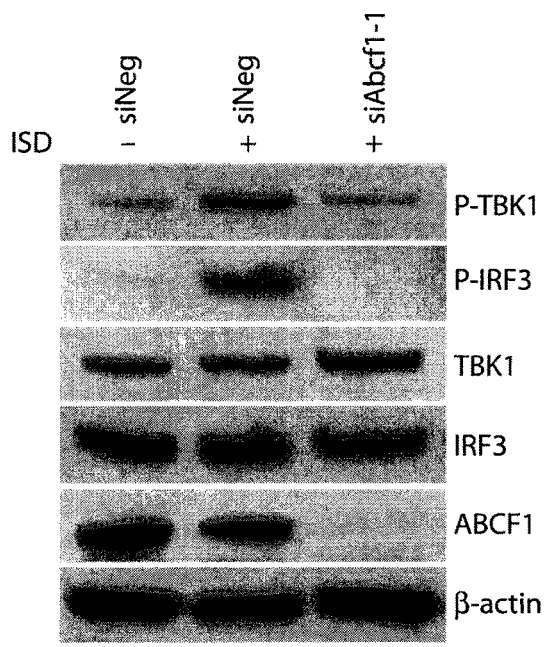
Figure 5F:
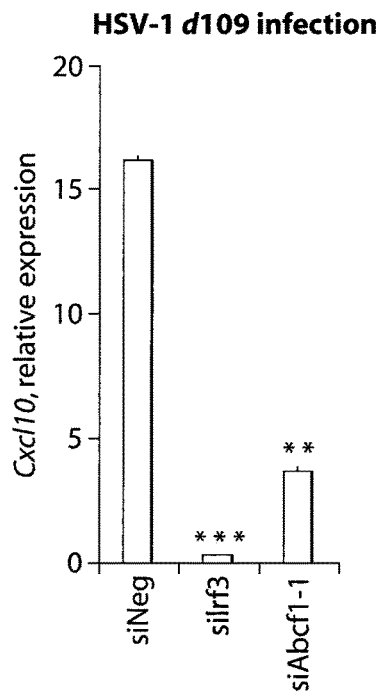
Figure 5G:
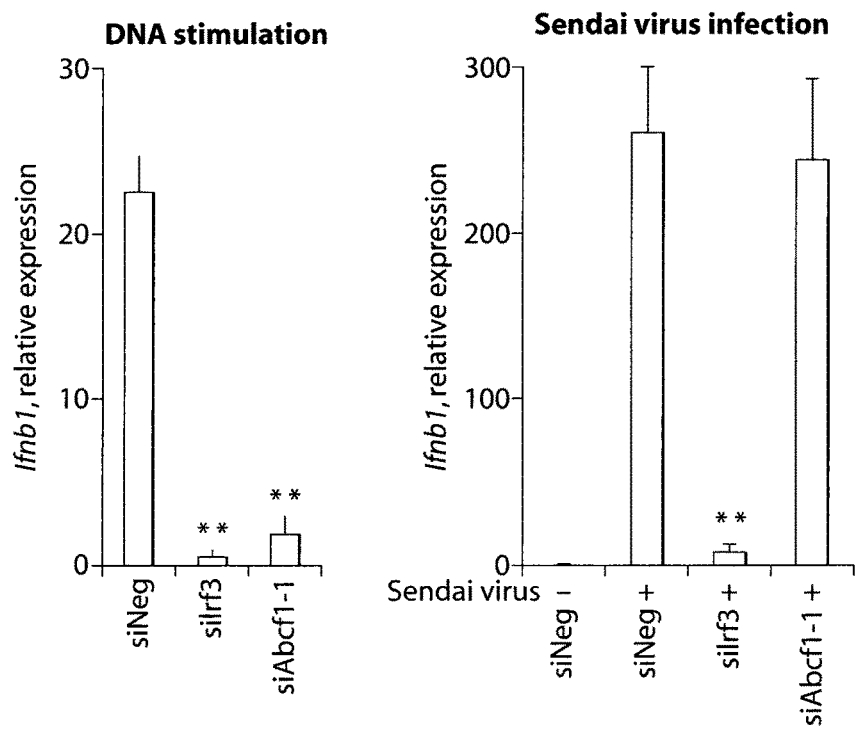
Figure 5H:
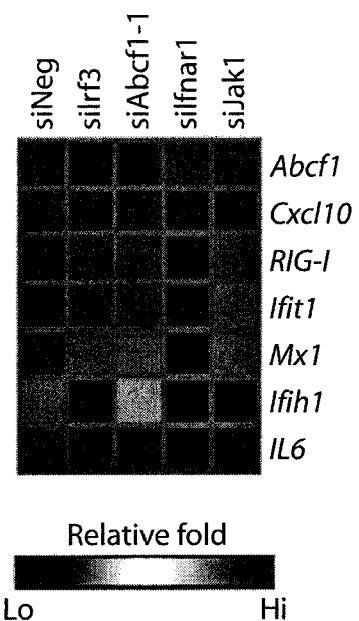

FIG. 5A-H is a series of graphs and illustrations shows identification of components of DNA sensing complex. FIG. 5A shows ABCF1 interactors. MEFs stably expressing Abcf1-HA or mock-transduced MEFs were stimulated with ISD or left unstimulated. Lysates were precipitated with anti-HA antibody. X-axis (M/L) and y-axis (H/L) correspond to co-precipitation with ABCF1-HA in the unstimulated and stimulated states, respectively. Blue/purple circles, hits with P-value <0.01; yellow squares, non-hit. FIG. 5B shows Interaction among proteins in DNA sensing network. Legend is same as in FIG. 2C. FIG. 5C shows MEFs stably expressing doxycycline-inducible Abcf1-HA were treated with doxycycline for 0, 24, or 48 h. Lysates were precipitated with anti-HA antibody or IgG control. Precipitates were immunoblotted with indicated antibodies. FIG. 5D Immunofluorescent microscopy of MEFs expressing HA-tagged Abcf1, stained for DAPI, HA, and SET. Merge of images is shown. FIG. 5E shows MEFs treated with indicated siRNAs were stimulated for 4 h with ISD, and lysates were immunoblotted with indicated antibodies. FIG. 5F shows MEFs treated with indicated siRNAs were infected with HSV-1 d109 for 6 h, and induction levels of Cxcl10 mRNA were determined by qRT-PCR. Data presented as mean and s.d. (n=4). FIG. 5G shows Trex1–/– MEFs treated with indicated siRNAs were stimulated with 4 ug/mL DNA (HIV gag-100) for 5.5 h or infected with Sendai virus for 6 h, and induction levels of Ifnb1 mRNA were determined by qRT-PCR. Data presented as mean and s.d. (n=3). In FIGS. 5F and 5G,  $P<0.01$,  $P<0.001$ compared with cells treated with control siRNA. FIG. 5H shows Trex1–/–MEFs treated with indicated siRNAs were stimulated with 300 U/mL IFNβ for 8 h, and expression levels of Abcf1 and ISG mRNA were determined by qRT-PCR. Data are averages of triplicate wells.

FIG. 6A-E is series of graphs and heat maps showing the inhibition of identified regulators by RNAi or small molecules modulates the innate immune response to retroviral infection. (FIG. 6A) Trex1–/–MEFs treated with indicated siRNAs were infected with retrovirus for 21.5 h, and induction levels of Cxcl10 mRNA were determined by qRT-PCR. P-values compared with control siRNA (siNeg)-treated cells (after Benjamini-Hochberg correction for multiple testing, marked as asterisks) with P=0.05 and P=0.10 indicated as dotted lines. Data presented as mean and s.d. (n=3). Known ISD pathway genes are indicated with arrowheads. Genes whose protein products can be inhibited by existing small molecule inhibitors are marked with arrows. (FIGS. 6B,6C) Trex1–/–MEFs treated with indicated siRNAs were infected with retrovirus, and induction levels of Ifnb1 mRNA were determined by qRT-PCR. Data presented as mean and s.d. (n=3). (FIGS. 6D, 6E) Trex1–/–MEFs treated with small molecule inhibitors were infected with retrovirus, and induction levels of Ifnb1 or a panel of ISGs was determined by qRT-PCR. Data are averages of duplicate wells. Small molecules were used at: 400 nM celastrol, 750 nM 17-DMAG, 500 nM BX795, 30 uM PTPN1 inhibitor, and 10 nM okadaic acid.

Figure 7:
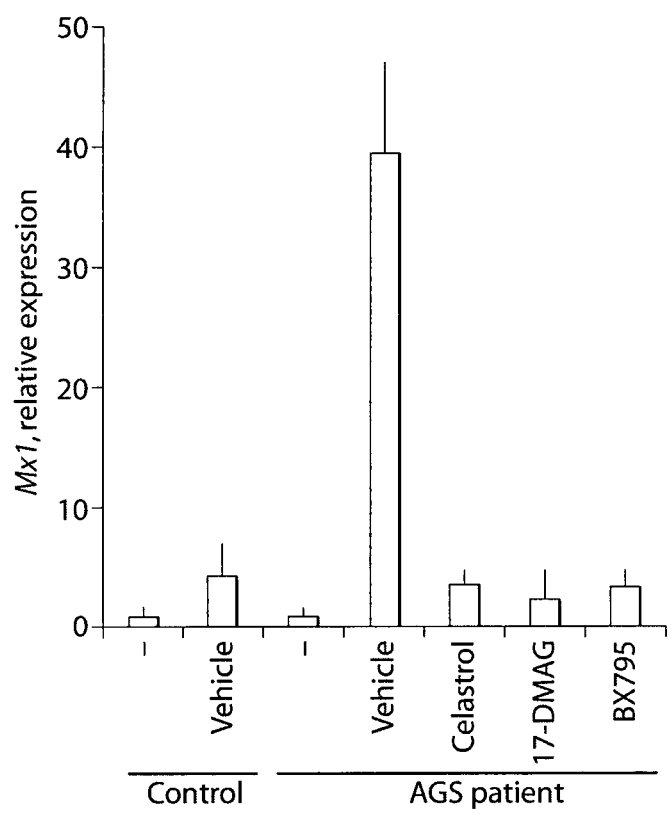

FIG. 7 is a graph showing the relative expression of Mx1 in Aicardi-Goutieres syndrome (AGS) patient and control cells. Human fibroblasts cultured from a healthy control and a patient with AGS who is compound heterozygote for mutations in the Trex1 gene (R114H/D201ins). Cells were treated with vehicle alone or small molecule inhibitors and infected with retrovirus. Induction levels of Mx1 were determined by qRT-PCR. Data are averages of triplicate wells. Small molecules were used at: 500 nM celastrol, 100 nM 17-DMAG, and 500 nM BX795.

Figure 8A:
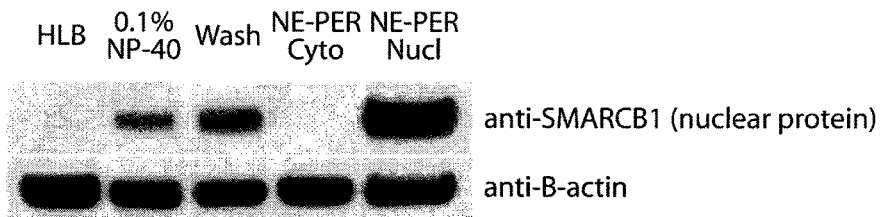
Figure 8B:
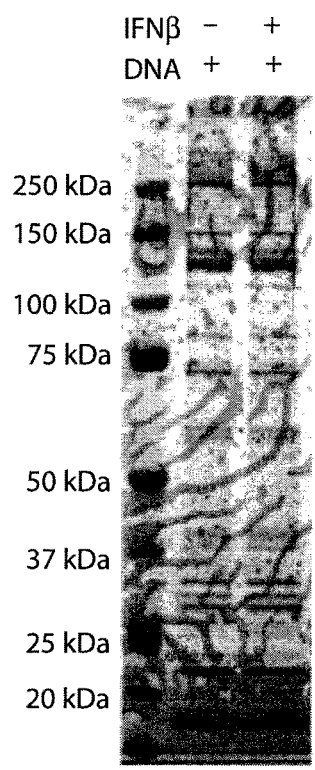
Figure 8C:
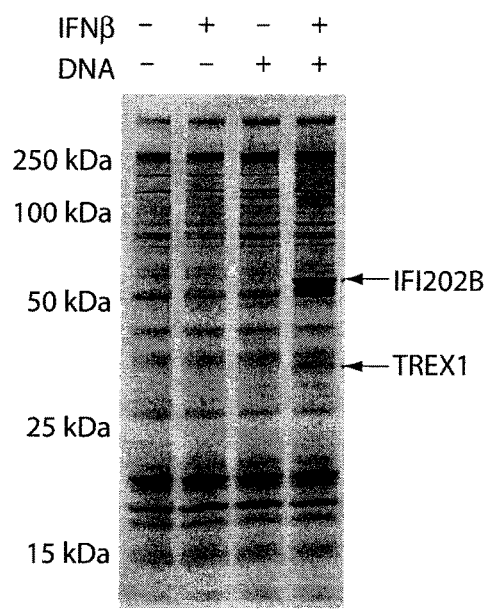
Figure 8D:
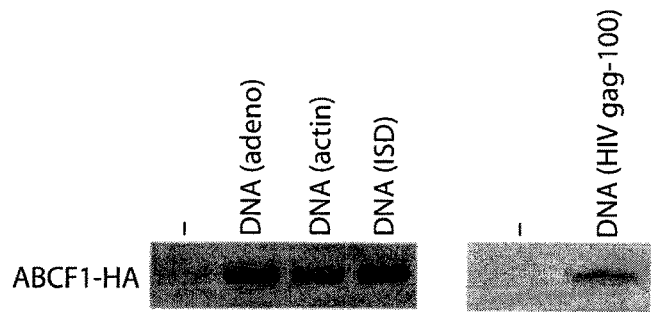

FIG. 8A-D is a series of blots and assays depicting the generation of a candidate gene set by curation and quantitative proteomics. FIG. 8A shows cytoplasmic extract preparation. MEFs were lysed in panel of lysis buffers. Lysates were immunoblotted with anti-SMARCB1 antibody (nuclear protein) and with anti-β-actin antibody (loading) control. Lysis buffers are described herein. FIG. 8B shows DNA pulldown. MEFs were pre-treated with IFNβ for 18 h or left unstimulated. Cytoplasmic extracts were prepared and incubated with biotinylated ISD. ISD-interacting proteins were precipitated with streptavidin beads, resolved by SDS-PAGE, and stained with Coomassie blue. Visualizable bands near 55 kDa and 35 kDa were identified by mass spectrometry as IFI202B and TREX1, respectively. FIG. 8C shows S35 DNA pulldown. MEFs were labeled with S35, and incubated with IFNβ for 6 h or left unstimulated. Cytoplasmic extracts were prepared and incubated with or without biotinylated ISD. ISD interacting proteins were precipitated with streptavidin beads, resolved by SDS-PAGE, and visualized by autoradiography. FIG. 8D shows DNA pulldown assays performed in MEFs stably expressing HA-tagged Abcf1 with biotinylated 45-bp dsDNA of various sequences. Precipitates were resolved by SDS-PAGE and immunoblotted with anti-HA antibody.

Figure 9A:
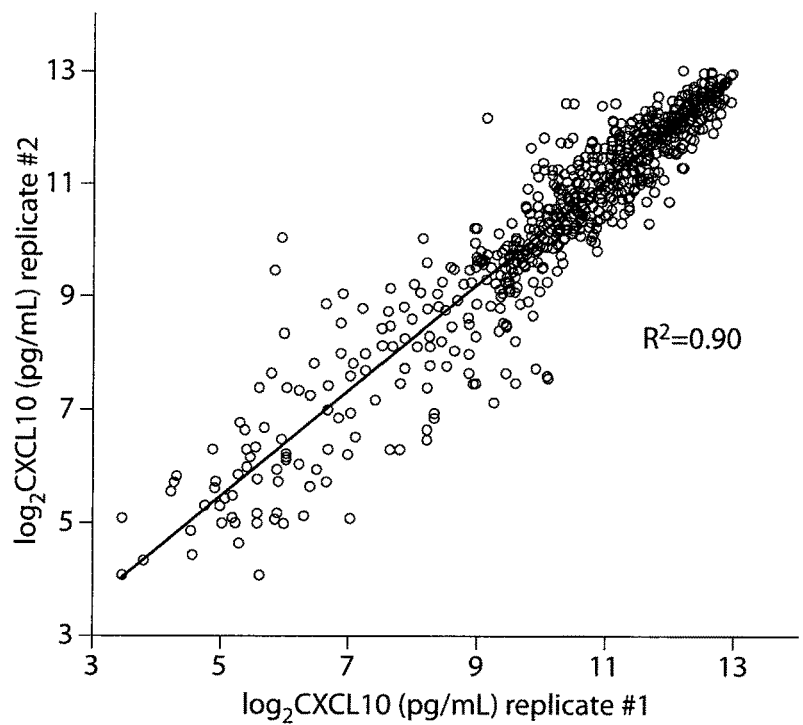
Figure 9A:
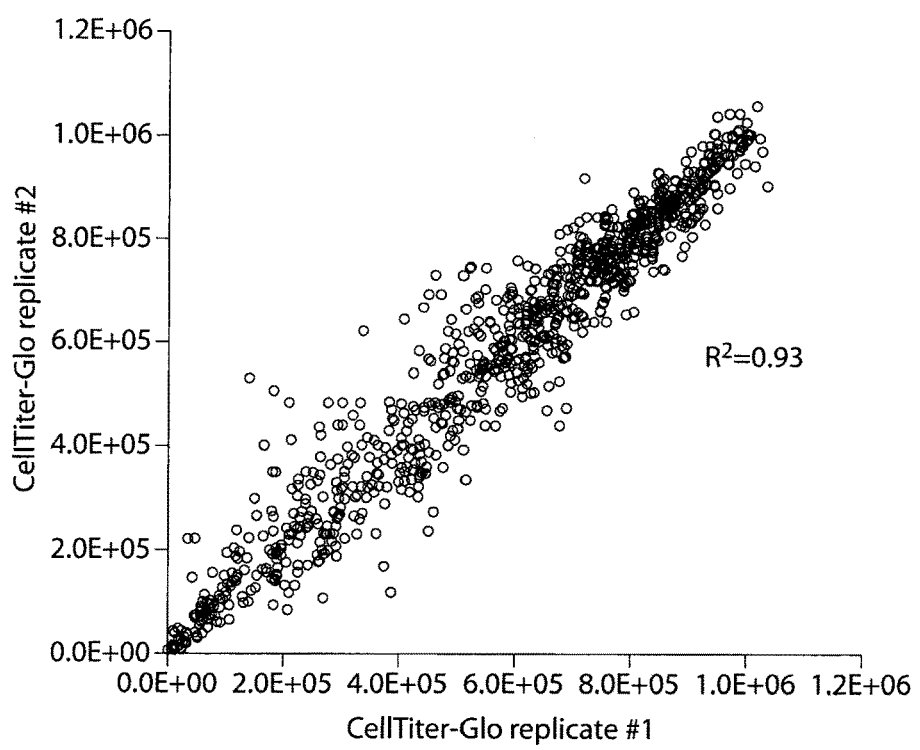
Figure 9B:
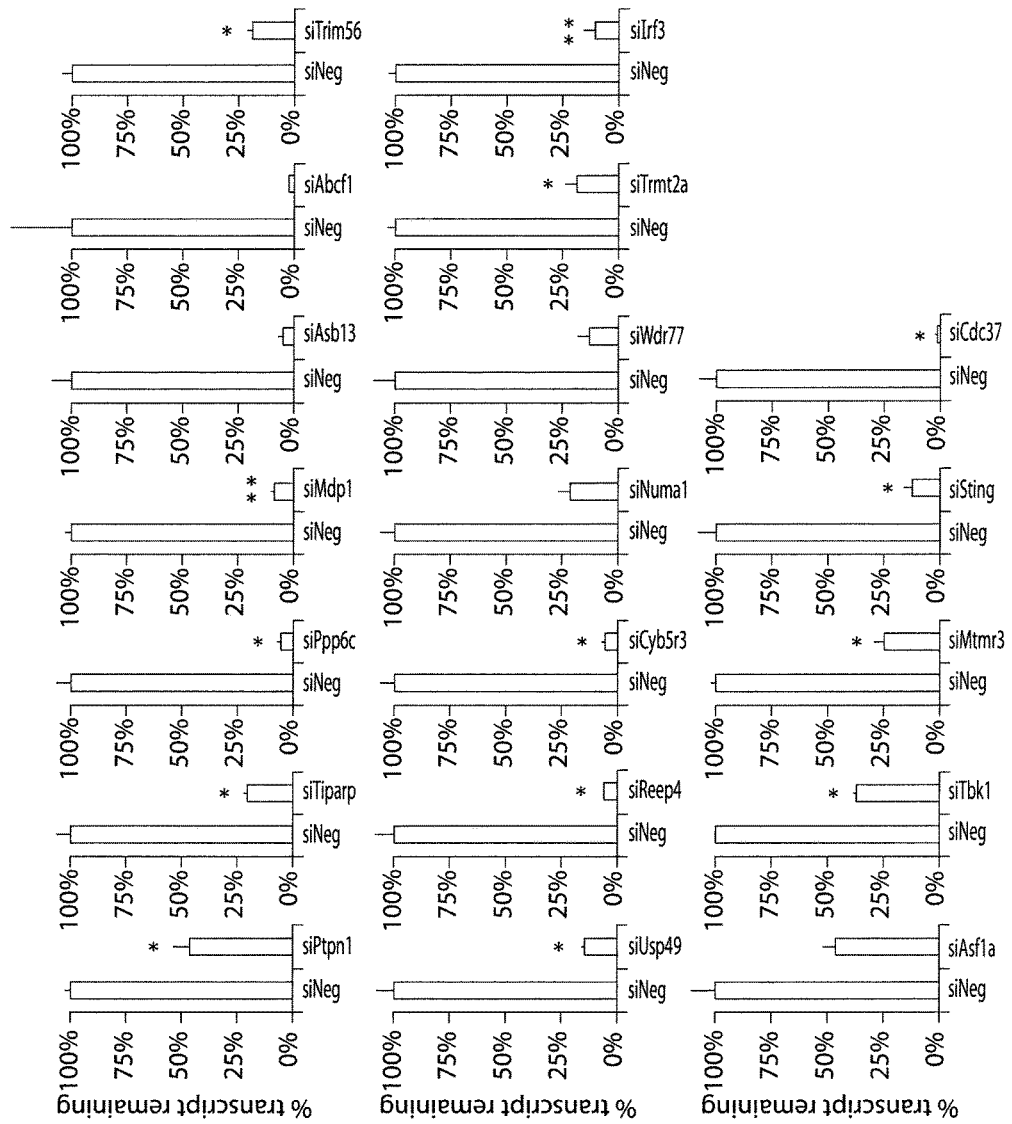

FIG. 9A-B is a series of graphs depicting high-throughput loss-of-function screening and network analysis of hits. FIG. 9A shows robustness of an siRNA screening assay. Log 2 CXCL10 (pg/mL) and CellTiter-Glo luminescence levels from representative plates from the siRNA screen were graphed (x-axis) along with their respective values from replicate plates (y-axis). R2 values are shown. FIG. 9B shows MEFs treated with control siRNA (siNeg) or indicated siRNAs. Expression levels of respective genes were measured by qRT-PCR. Data is presented as mean and s.d. (n=2). * P<0.05, ** P<0.01. The x-axis label for the left bar in each graph is siNeg. The x-axis label for the right bar in each graph is as follows, from left to right: Top row: siPtpn1, siTiparp, siPpp6c, siMdp1, siAsb13, siAbcf1, siTrim56; Middle row: siUsp49, siReep4, siCyb5r3, siNuma1, siWdr77, siTrmt2a, siIrf3; Bottom row: siAsf1a, siTbk1, siMtmr3, siSting, and siCdc37.

Figure 10A:
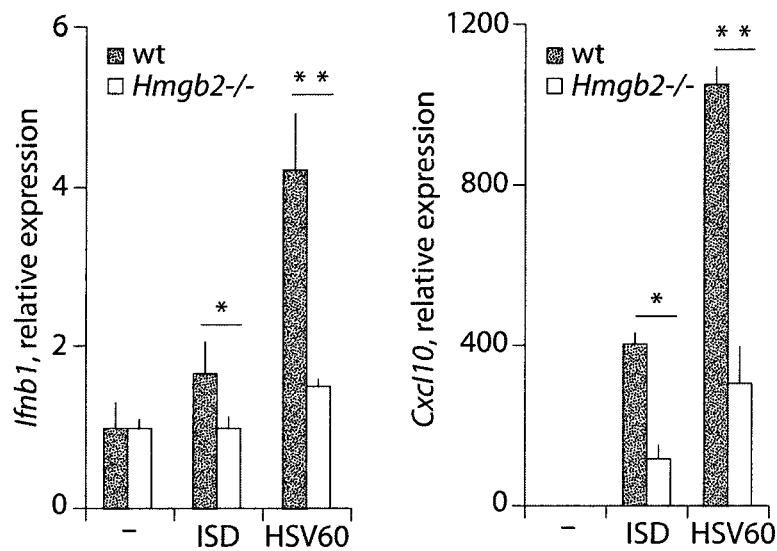
Figure 10B:
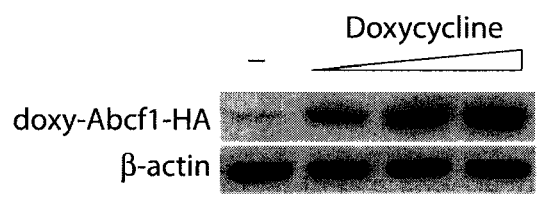
Figure 10C:
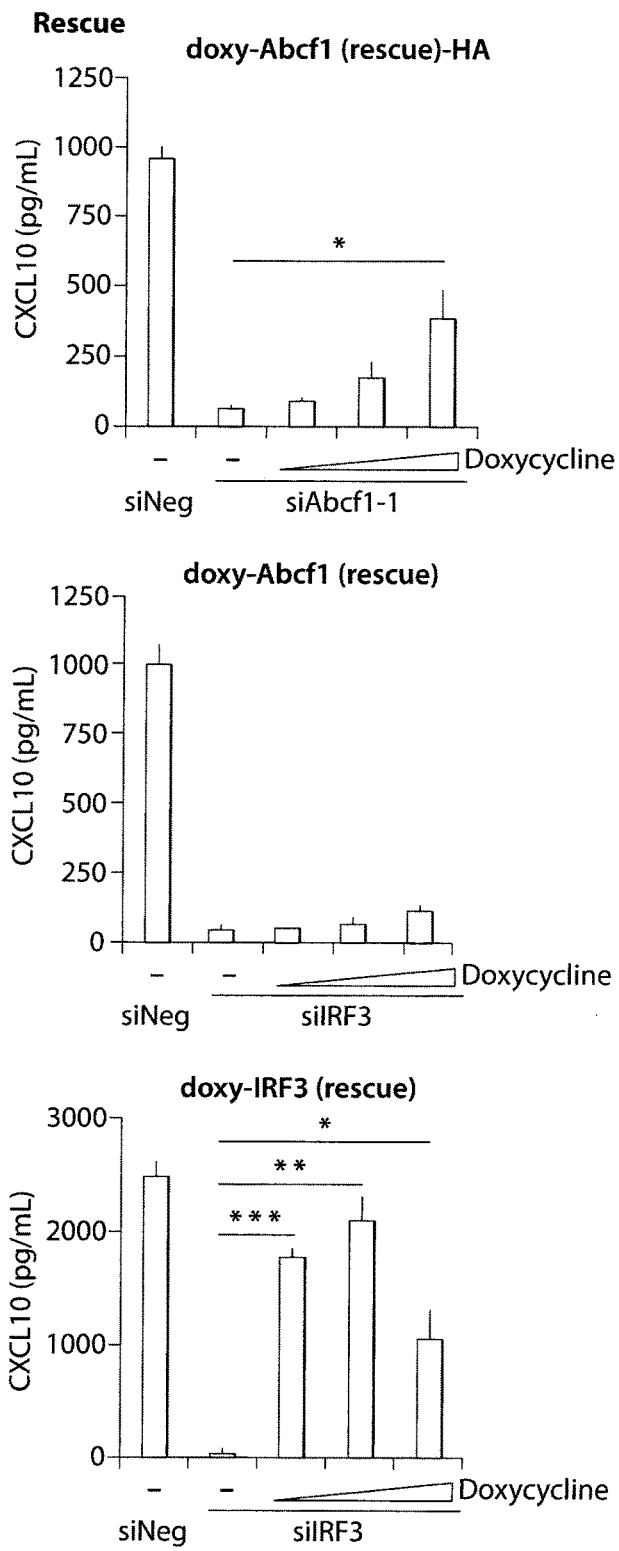

FIG. 10A-C is a series of graphs and an immunoblot showing validation of screening hits. FIG. 10A shows Hmgb2-/- and wt MEFs stimulated with DNA (ISD or HSV60 sequence) for 6 h. Cxcl10 induction was measured by qRT-PCR.* P<0.05, ** P<0.01. Data in all panels is presented as mean and s.d. (n=3). FIG. 1B shows MEFs stably expressing doxycycline-inducible Abcf1-HA which were treated with 0, 0.3, 3, or 30 ug/mL doxycycline. Lysates were immunoblotted with anti-HA or anti-β-actin antibody. FIG. 10C shows validation by cDNA rescue. MEFs stably expressing doxycycline-inducible Abcf1(rescue)-HA, Abcf1(rescue), or Irf3(rescue) cDNA were treated with siNeg, siAbcf1, or siIrf3 along with doxycycline (0, 0.3, 3, 30 ug/mL). Cells were stimulated with ISD and CXCL10 production was measured by ELISA. * P<0.05 compared with knockdown cells without doxycycline treatment.

Figure 11C:
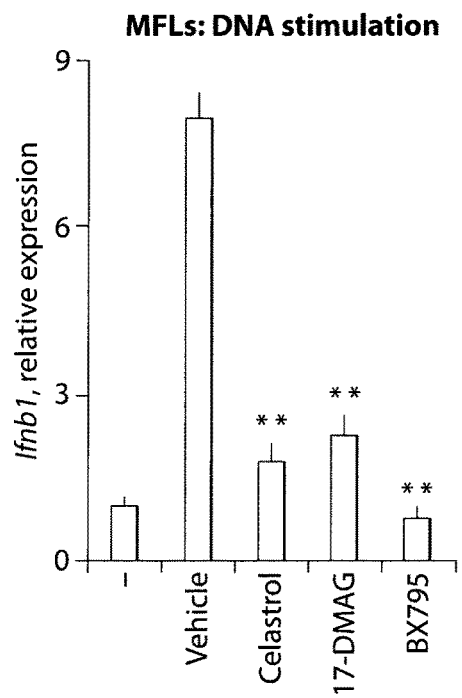
Figure 11C:
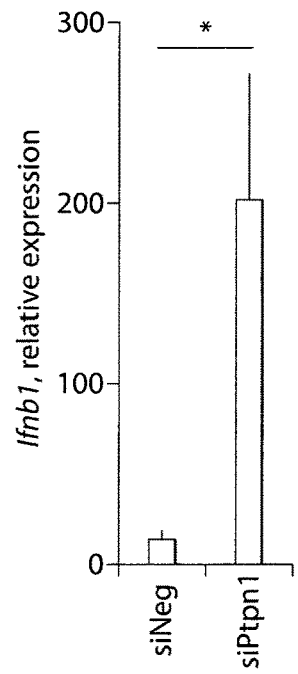
Figure 11C:
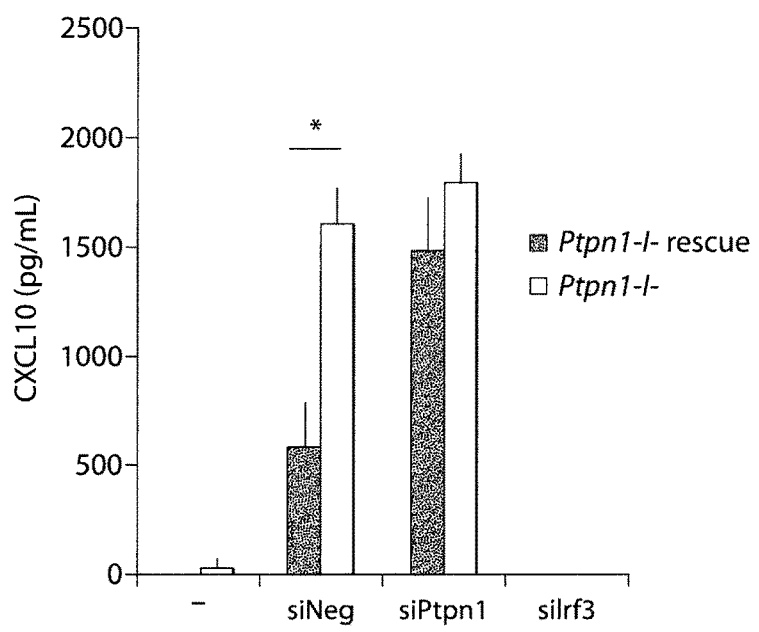
Figure 11D:
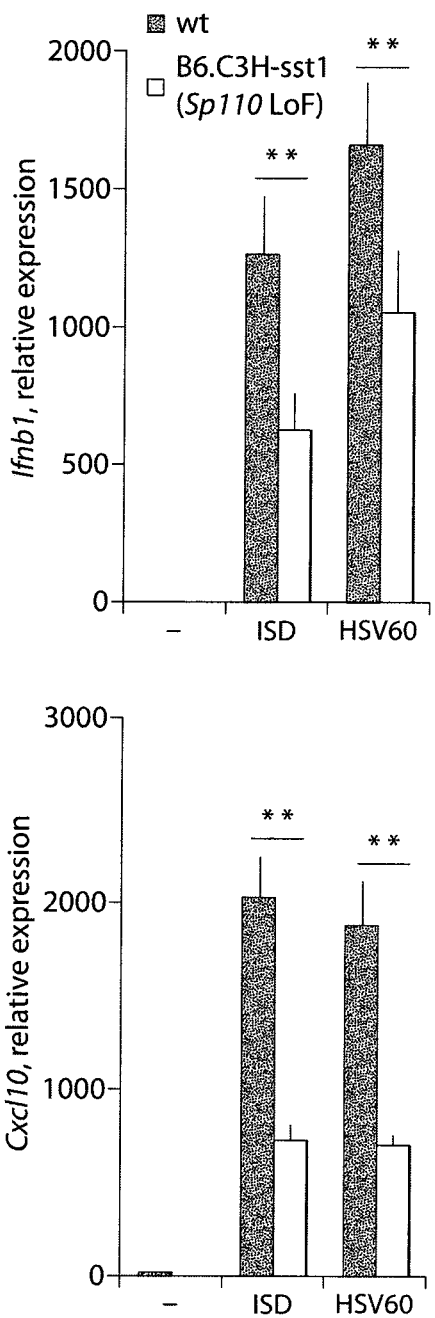

FIG. 11A-D is a series of graphs showing targeting of screening hits by small molecule inhibitors. FIG. 11A shows primary murine lung fibroblasts (MLFs) treated with small molecule inhibitors (500 nM celastrol, 750 nM 17-DMAG, 500 nM BX795) which were stimulated with 4 ug/mL DNA (HIV gag-100) for 5.5 h, and induction levels of Ifnb1 mRNA as determined by qRT-PCR. Data in all panels is presented as mean and s.d. (n=3). ** P<0.01 compared with DNA-stimulated vehicle-treated cells. FIG. 11B shows Trex1-/- MEFs treated with indicated siRNAs which were stimulated with DNA (HIV gag-100) for 5.5 h, and Ifnb1 induction as measured by qRT-PCR. * P<0.05. FIG. 11C shows Ptpn1-/- MEFs and Ptpn1-/- MEFs rescued with Ptpn1 cDNA which were treated with indicated siRNAs and then stimulated with ISD for 26 h; CXCL10 levels were determined by ELISA. Graphs show that siPtpn1 increases CXCL10 levels in rescued MEFs, but does not have a significant phenotype in Ptpn1-/- MEFs. * P<0.05. FIG. 11D shows B6.C3H-sst1 (Sp110 LoF) cDCs and wt control cells which were stimulated with DNA for 6 h, and Ifnb1 and Cxcl1 induction as measured by qRT-PCR. ** P<0.01.

Figure 12A:
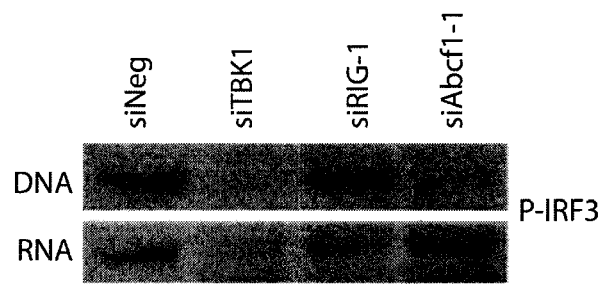
Figure 12B:
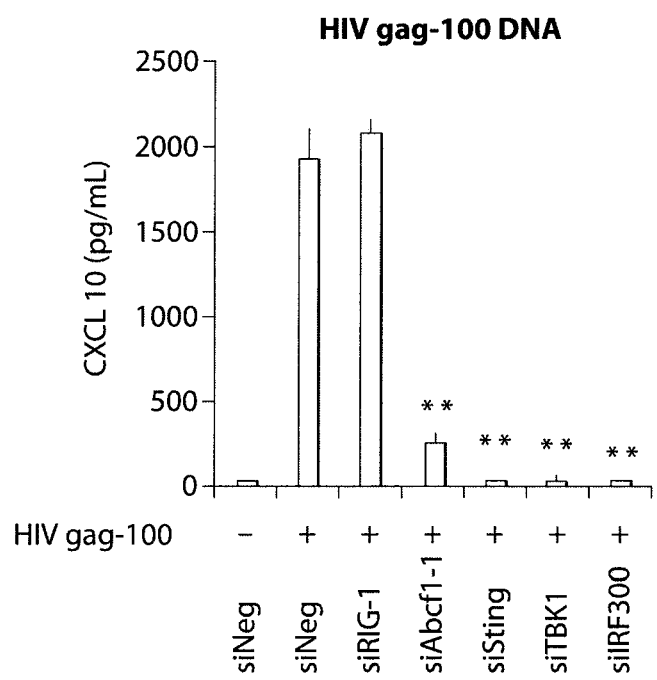
Figure 12C:
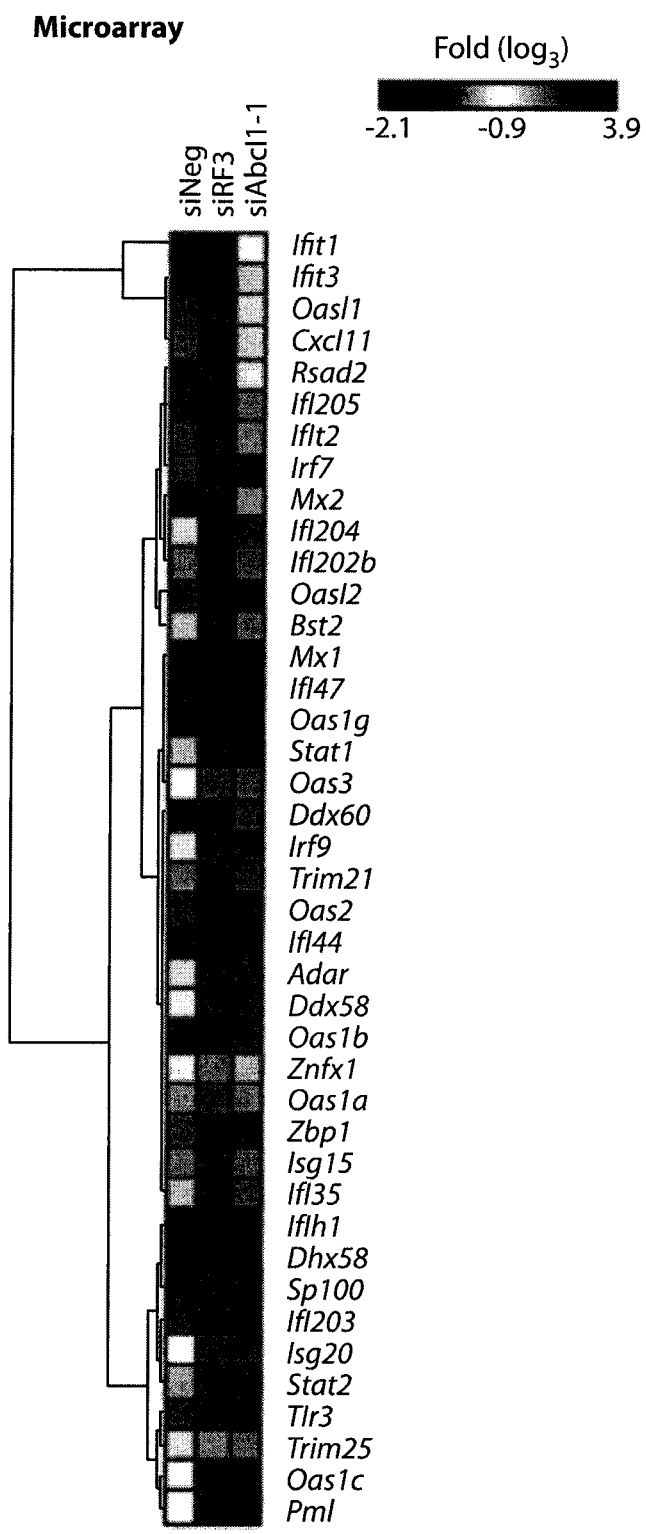
Figure 12D:
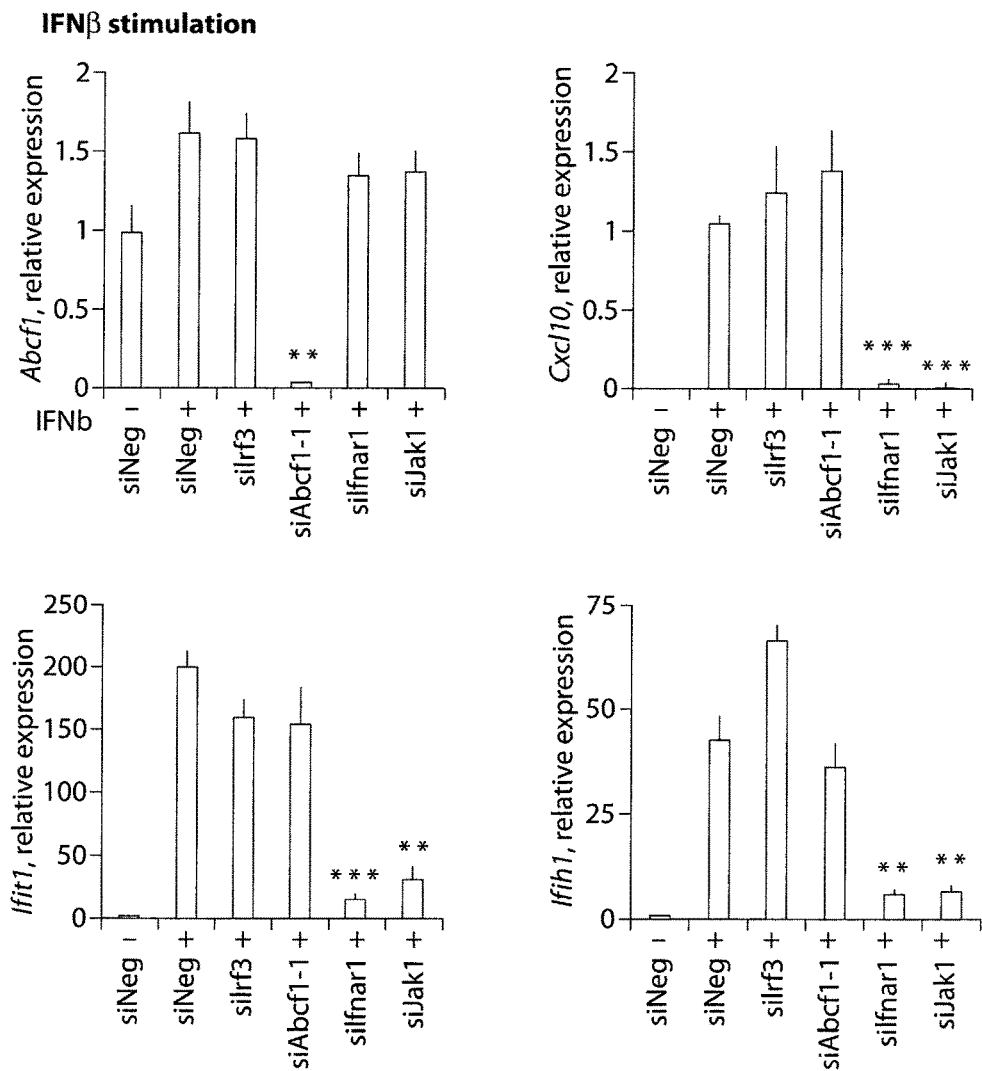

FIG. 12A-D shows identification of components of DNA sensing complex. FIG. 12A shows results where MEFs were treated with indicated siRNAs and stimulated for 3 h with ISD or in vitro transcribed RNA, and lysates, and were immunoblotted with anti-phopho-IRF3 (Ser396) antibody. FIG. 12B shows results where MEFs treated with indicated siRNAs were stimulated with DNA (HIV gag-100) for 26 h, and CXCL10 production was measured by ELISA.  P<0.01 compared with DNA-stimulated control siRNA (siNeg)-treated cells. Data is presented as mean and s.d. (n=3). FIG. 12C shows results of microarray analysis of MEFs treated with siRNAs and stimulated with ISD for 5.5 h. Log 2 fold changes of selected genes relative to unstimulated siNeg treated cells are displayed as a heat map. Data are averages of two biological replicates. The names listed at the left of FIG. 12C are from top to bottom: Ifit1, Ifit3, Oas1l, Cxcl11, Rsad2, Ifi205, Ifit2, Irf7, Mx2, Ifi204, Ifi202b, Oas12, Bst2, Mx1, Ifi47, Oas1g, Stat1, Oas3, Ddx60, Irf9, Trim21, Oas2, Ifi44, Adar, Ddx58, Oas1b, Znfx1, Oas1a, Zbp1, Isg15, Ifi35, Ifih1, Dhx58, Sp100, Ifi203, Isg20, Stat2, Tlr3, Trim25, Oas1c, and Pml. FIG. 12D shows results of raw data from FIG. 5H. Trex1-/- MEFs treated with indicated siRNAs which were stimulated with 300 U/mL IFNβ for 8 h, and expression of Abcf1 mRNA as well as induction levels of ISGs which were determined by qRT-PCR.  P<0.01, *** P<0.001 compared with IFNβ-stimulated siNeg-treated cells. Data is presented as mean and s.d. (n=3). For each graph in FIG. 12D, the X-axis column labels are from left to right: siNeg, siNeg, siIrf3, siAbcf1-1, silfnar1, and siJak1.

Figure 13A:
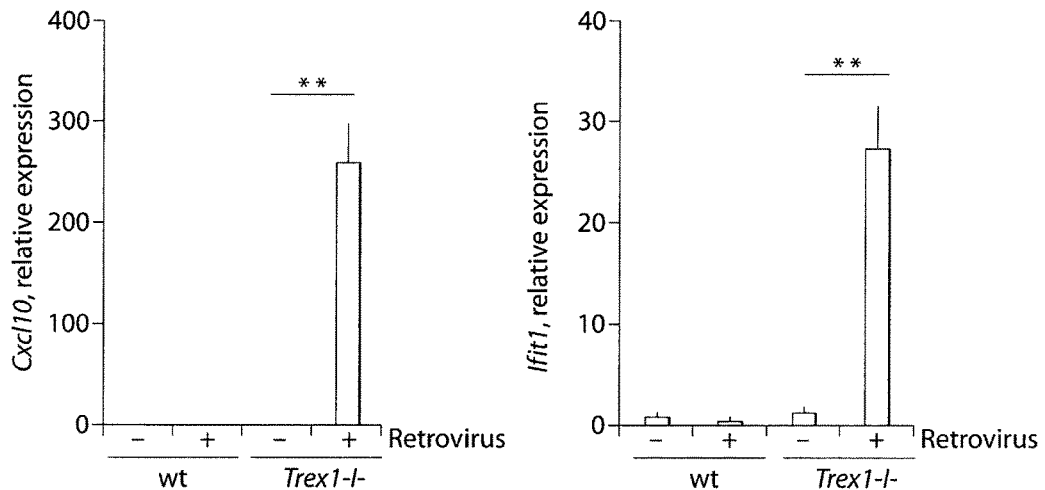
Figure 13B:
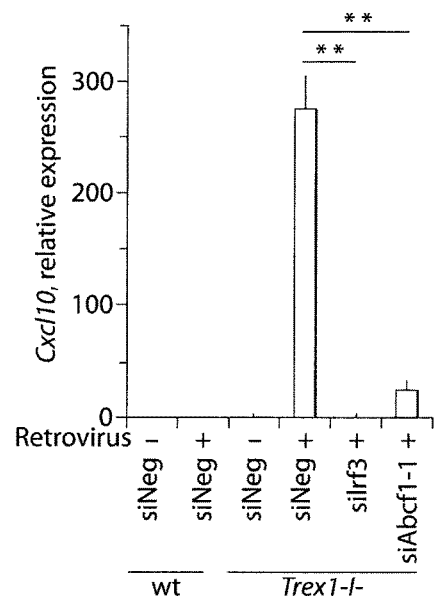
Figure 13C:
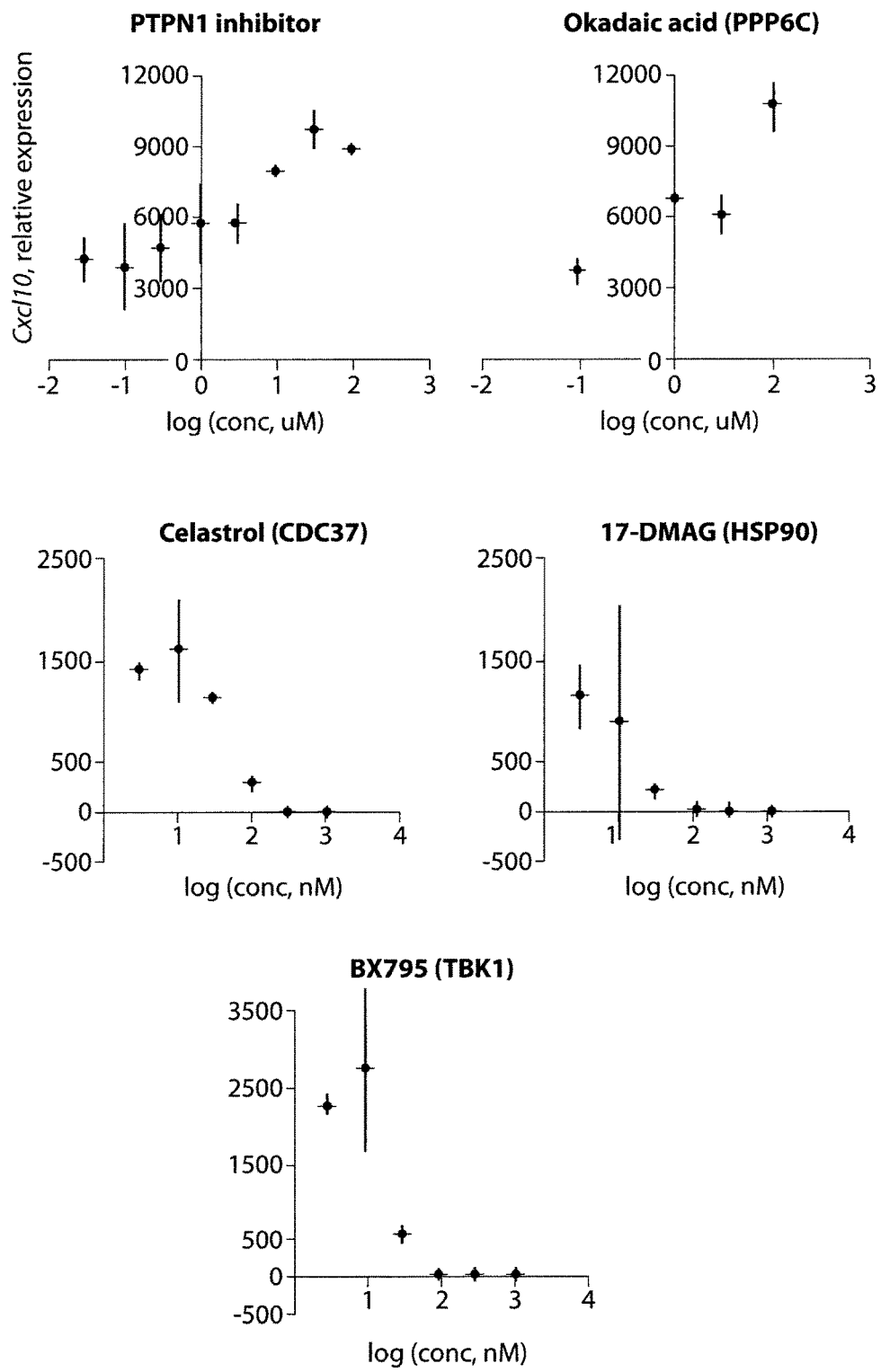

FIG. 13A-C is a series of graphs showing inhibition of identified regulators by RNAi or small molecules modulates the innate immune response to retroviral infection. FIG. 13A shows results where wt or Trex1-/- MEFs were infected with retrovirus for 21.5 h or left uninfected, and induction levels of Cxcl10 and Ifit1 were determined by qRT-PCR.  P<0.01. Data is presented as mean and s.d. (n=3). FIG. 13B shows results where wt or Trex1-/- MEFs treated with indicated siRNAs were infected with retrovirus for 21.5 h, and induction levels of Cxcl10 mRNA were determined by qRT-PCR.  P<0.01. Data presented as mean and s.d. (n=3). FIG. 13C shows results where Trex1-/- MEFs treated with small molecules at various doses were infected with retrovirus for 21.5 h, and induction levels of Cxcl10 mRNA were determined by qRT-PCR. Data presented as mean and s.d. (n=2).

DETAILED DESCRIPTION OF INVENTION

The invention is premised, in part, on the identification of novel components of a signaling pathway that mediates innate immune responses triggered by the presence of cytosolic DNA. This pathway is referred to herein as the "DNA sensing pathway". These newly discovered components can be targeted in order to modulate the DNA sensing pathway and the innate immune response it triggers. The invention therefore provides methods for modulating the DNA sensing pathway with the aim of also modulating the innate immune response activated by the pathway as a result of the presence of cytosolic DNA. Certain methods of the invention modulate other immune responses in addition to those responses triggered by the DNA sensing pathway. That is, some methods provided herein modulate the RNA sensing pathway as well the DNA sensing pathway.

Thus, in some instances, the invention contemplates down-regulating the DNA sensing pathway thereby reducing, in whole or in part, or preventing the occurrence of the downstream innate immune response. In some instances, the invention contemplates down-regulating the innate immune response that is downstream of the DNA sensing pathway by targeting intermediate components in the overall pathway. Such down-regulation would be useful in aberrant immune responses that are triggered by the presence of DNA (such as cytosolic DNA). The presence of cytosolic DNA may be the result of a mutation in a nuclease that normally functions to prevent the accumulation of DNA in the cytosol. An example of such a nuclease is TREX1. Examples of other nucleases involved in preventing accumulation of nucleic acids in the cytosol include Dnase1, Dnase2, Fen1 (DnaseIV), RnaseH2, and SAMHD1. Subjects having such nuclease mutations are more likely to develop aberrant immune responses due to the inappropriate presence of DNA. In some instances, the subjects have or are at risk of developing an autoimmune disorder. Of particular interest are the autoimmune disorders AGS, FCL, and RVCL. Also of interest are subjects having a nuclease mutation and, for example, a retroviral infection. In these latter instances, it may be desirable to down-regulate the DNA-triggered immune response to the retrovirus to a level that is sufficient to attack the retrovirus and keep it from spreading yet that is also sufficiently controlled so as not to induce autoimmunity (or bring about an autoimmune event or recurrence).

The methods of the invention may be used to treat subjects identified through the presence of or an abnormal level of a DNA sensing pathway marker. In this way, the invention provides a personalized medicine approach. The ability to identify subjects having an overactive DNA sensing pathway (as denoted by the presence of or by an abnormal level of a DNA sensing pathway marker) allows a medical practitioner to treat only that subset of subjects that is considered most likely to respond beneficially to the treatments contemplated herein. This tailored treatment strategy avoids administering ineffective agents to subjects, many of whom are severely ill, without therapeutic benefit and in some cases with unwanted and perhaps unacceptable side effects. The invention therefore contemplates that not all autoimmune disorders are associated with an aberrant DNA sensing pathway and that only those associated with such an aberrant pathway should be treated using the methods of the invention. As an example, EAE, an experimental model system of human autoimmune disorder, is not associated with an aberrant DNA sensing pathway.

Such markers include mRNA or protein levels of interferon or interferon-stimulated gene (collectively, referred to as ISG) in for example monocytes-derived dendritic cells, skin fibroblasts or blood cells, particularly following stimulation with transfected DNA or a retrovirus, levels of interferon proteins in peripheral blood serum or cerebrospinal fluid, and presence of nuclease mutations such as Trex1 mutations, Dnase1 mutations, Dnase2 mutations, Fen1 mutations, RnaseH2 mutations and SAMHD1 mutations. It is to be understood that such markers may also be used to diagnose an aberrant DNA sensing pathway. As used herein, an aberrant DNA sensing pathway is an overactive DNA sensing pathway. Any of the markers set forth herein may be used to determine if a subject has an aberrant or overactive DNA sensing pathway. This diagnosis may be performed in a subject who is asymptomatic. Certain methods of the invention therefore include a step of identifying a subject having an aberrant DNA sensing pathway following by a step of treating the subject with a particular inhibitors. The invention contemplates the use of ABCF1 inhibitors, HSP900 inhibitors, and/or CDC37 inhibitors, alone or in combination, including any combination thereof for down-regulating innate immune responses. These inhibitors are discussed in greater detail herein. These inhibitors may be used in combination with TBK1 inhibitors. As shown in the Examples, treatment of cells from an AGS patient with the CDC37 inhibitor celastrol or the HSP90 inhibitor 17-DMAG failed to induce Mx1 expression following retroviral infection, as compared to cells exposed to only vehicle. The reduction, in some instances, was also 40-fold compared to the vehicle-exposed cells. This degree of down-regulation was unexpected particularly since it was achieved using a variety of single agents that inhibit different targets.

In some embodiments, the level (e.g., gene or protein level) of HSP90, CDC37, ABCF1 and optionally TBK1 is normal in the subject (or in cells obtained from the subject). Accordingly, in some embodiments, subjects having normal levels of HSP90, CDC37, and/or ABCF1, and optionally TBK1 are intended to be treated by the methods of the invention using the classes of inhibitors taught herein.

In some embodiments, the HSP90 inhibitor is an agent that binds to HSP90 protein and interferes with its binding to CDC37. The HSP90 inhibitor may not interfere with the ATP-binding activity of HSP90, in some embodiments.

In some embodiments, the CDC37 inhibitor is an agent that binds to CDC37 protein and interferes with its binding to HSP90.

In some instances, the invention contemplates up-regulating the DNA-triggered innate immune response in order to provide a more robust immune response in a subject. Such up-regulation would be useful in instances where the DNA-triggered immune response is beneficial and it is desirable to increase the level of that response. As an example, it may be desirable to up-regulate an immune response in the context of infections such as certain viral infections and certain bacterial infections, in an environment of dying cells including dying tumor cells, dying infected cells, and the like, and in the context of DNA vaccines. The invention contemplates the use of PTPN1 and PPP6C inhibitors, alone or in combination, to up-regulate the innate immune response. These inhibitors are discussed in greater detail herein. The finding that inhibition of these signaling pathway components would up-regulate the immune response was unexpected.

Innate immunity, which is also known in the art as natural or native immunity, is an immune response that involves neutrophils, granulocytes, mononuclear phagocytes, dendritic cells, NKT cells, and NK cells. Innate immune responses can include, without limitation, type I interferon (such as IFN-alpha and IFN-beta) production, neutrophil activation, macrophage activation, phagocytosis, opsonization, complement activation, and any combination thereof.

Inhibitors

The invention contemplates the use of inhibitors to down-regulate or up-regulate innate immune responses. One or more inhibitors may target components of the DNA sensing pathway in order to down-regulate or up-regulate innate immune responses. Inhibitors that down-regulate the innate immune response may be used individually or in combination. Similarly, inhibitors that up-regulate the innate immune response may be used individually or in combination.

ABCF1 (ATP-binding cassette sub-family F member 1) is a 845 amino acid protein encoded by the human gene ABCF1. The human homolog of ABCF1 is also known as ABC50 and ABC27, and the murine homolog is also known as Abc50, GCN20, AU41969 and D17Wsu166e in mouse. Nucleotide and amino acid sequences can be found at GenBank Accession No. NM_001025091.1 for human ABCF1 and NM_013854.1 for mouse ABCF1. ABCF1 belongs to the ABC transporter family (EF3 subfamily) and contains two ABC transporter domains. ABC proteins are thought to transport various molecules across extra- and intra-cellular membranes.

As used herein, an ABCF1 inhibitor is an agent that inhibits ABCF1 activity. The inhibitor can be nucleic acid or amino acid in nature, and in some important embodiments it is a chemical compound, whether organic or inorganic in nature. The inhibitor may prevent or reduce the synthesis of ABCF1 for example by blocking its mRNA or protein expression. Alternatively, it may reduce activity by interfering with ABCF1 function, such as by binding by ABCF1 and thereby interfering with its ability to bind DNA, or HMGB2, IFI16 or other proteins. Antibodies that bind to ABCF1 are described in U.S. Pat. No. 7,612,181. U.S. Pat. No. 7,482,334 also provides compounds that may be used in the invention as inhibitors of ABCF1. Reference may also be made to U.S. Pat. Nos. 7,910,571, 7,935,839, and 7,547.687.

As used herein, a HSP90 inhibitor is an agent that inhibits HSP90 activity. The inhibitor can be nucleic acid or amino acid in nature, and in some important embodiments it is a chemical compound, whether organic or inorganic in nature. The inhibitor may prevent or reduce the synthesis of HSP90 for example by blocking mRNA or protein expression. Alternatively, it may reduce activity by interfering with HSP90 function, such as by binding by HSP90 and thereby interfering with its ability to bind ATP or other proteins. Examples of HSP90 inhibitors which can be used with the methods of the present invention include, but are not limited to, quinone ansamycin antibiotics, such as the macbecins, geldanamycin, including derivatives of geldanamycin, such as 17-(allylamino)-17-desmethoxygeldanamycin (17-AAG), its dihydro derivative, 17-AAGH$_2$, and 17-amino derivatives of geldanamycin such as 17-dimethylaminoethylamino-17-demethoxy-geldanamycin (17-DMAG), 11-oxogeldanamycin, and 5,6-dihydrogeldanamycin, which are disclosed in U.S. Pat. Nos. 4,261,989; 5,387,584; and 5,932,566, each of which is incorporated herein by reference. Another HSP90 inhibitor is ganetespib.

Other suitable HSP90 inhibitors include radicicol and oximes and other analogs thereof, disclosed in Soga, et al., Curr. Cancer Drug Targets, 3, 359-69 (2003), and in Yamamoto, et al., Angew. Chem., 42, 1280-84 (2003); and in Moulin, et al., J. Amer. Chem. Soc., vol 127, 6999-7004 (25); purine derivatives such as PU3, PU24FCI and PUH64 (see Chiosis et al., ACS Chem. Biol. Vol. 1(5), 279-284 (2006) and those disclosed in PCT Application No. WO 2002/0236075; related heterocyclic derivatives disclosed in PCT Application No. WO 2005/028434; and 3,4-diarylpyrazole compounds disclosed in Cheung, et al., Bioorg. Med. Chem. Lett., vol. 15, 3338-43 (2005). Other HSP90 inhibitors include novobiocin analogues, as provided by U.S. Pat. No. 7,622,451, which is incorporated herein by reference. Further examples of HSP90 inhibitors include dexamethasone and benzoquinone ansamycins such as those described in U.S. Pat. No. 6,872,715, incorporated herein by reference. Yet additional HSP90 inhibitors include herbimycin A and other synthetic compounds that can bind into the ATP-binding site of HSP90, as disclosed by U.S. Pat. No. 7,211,562, incorporated herein by reference. Antibodies or antibody fragments that selectively bind to HSP90 may also be administered as drugs to cause inhibition of HSP90, and can be used in combination with the compounds of the invention.

Nucleotide and amino acid sequences can be found using GenBank Accession No. NM_005348.2 for human Hsp90AA, NM_007355.2 for human Hsp9AB1, NM_010480.5 for mouse Hsp90AA 1, and NM_008302.3 for mouse Hsp90AB1.

As used herein, a CDC37 inhibitor is an agent that inhibits CDC37 activity. The inhibitor can be nucleic acid or amino acid in nature, and in some important embodiments it is a chemical compound, whether organic or inorganic in nature. The inhibitor may prevent or reduce the synthesis of CDC37 for example by blocking mRNA or protein expression. Alternatively, it may reduce activity by interfering with CDC37 function, including interaction with its partner HSP90.

An example of a CDC37 inhibitor is celastrol. Celastrol has been reported to be an HSP90 inhibitor in the art. However, the findings provided herein indicate that it binds to CDC37 and may inhibit HSP90 only indirectly (e.g., by preventing the binding of HSP90 to CDC37).

Nucleotide and amino acid sequences can be found using GenBank Accession No. NM_007065.3 for human CDC37 and NM_016742.4 for mouse CDC37.

As used herein, a TBK1 inhibitor is an agent that inhibits TBK1 activity. The inhibitor can be nucleic acid or amino acid in nature, and in some important embodiments it is a chemical compound, whether organic or inorganic in nature. The inhibitor may prevent or reduce the synthesis of TBK1 for example by blocking mRNA or protein expression. Alternatively, it may reduce activity by interfering with TBK1 function, such as binding to and/or interfering with catalytic sites (e.g., kinase domain) or protein-protein interaction domains.

Examples of TBK1 inhibitors include, but are not limited to, MPI-0485520 (Myrexis, Inc.), BX 795 (CAS No. 702675-74-9, Axon Medchem BV), MRT67307 (CAS No. 1190378-57-4, Medchem Express), CYT387, as well as those disclosed in U.S. Pat. Nos. 8,263,139; 7,211,597; 7,186.743; 6,956,052; and 6,849,653, all incorporated herein by reference.

Nucleotide and amino acid sequences can be found using GenBank Accession No. NM_013254.3 for human TBK1 and NM_019786.4 for mouse TBK1.

As used herein, a PTPN1 inhibitor is an agent that inhibits PTPN1 activity. The inhibitor can be nucleic acid or amino acid in nature, and in some important embodiments it is a chemical compound, whether organic or inorganic in nature. The inhibitor may prevent or reduce the synthesis of PTPN1 for example by blocking mRNA or protein expression. Alternatively, it may reduce activity by interfering with PTPN1 function.

In one example, a PTPN1 inhibitor is 3-(3,5-Dibromo-4-hydroxy-benzoyl)-2-ethyl-benzofuran-6-sulfonicacid-(4-(thiazol-2-ylsulfamyl)-phenyl)-amide.

As used herein, a PPP6C inhibitor is an agent that inhibits PPP6C activity. The inhibitor can be nucleic acid or amino acid in nature, and in some important embodiments it is a chemical compound, whether organic or inorganic in nature.

The inhibitor may prevent or reduce the synthesis of PPP6C for example by blocking mRNA or protein expression. Alternatively, it may reduce activity by interfering with PPP6C function.

In some embodiments, the innate immune response is down-regulated by one or more inhibitors that inhibits type I-interferon signaling, induction, or response. In some embodiments, the innate immune response is down-regulated by one or more inhibitors that inhibit the functions of one or more proteins selected from the group consisting of: TP53, RARRES3, IFNA1, IFNA2, IFNA4, IFNA5, IFNA6, IFNA7, IFNA8, IFNA10, IFNA13, IFNA14, IFNA16, IFNA17, IFNA21, IFNK, IFNB1, IL6, TICAM1, TICAM2, MAVS, STAT1, STAT2, EIF2AK2, IRF3, TBK1, CDKN1A, CDKN2A, RNASEL, IFNAR1, IFNAR2, OAS1, OAS2, OAS3, OASL, RBI, ISG15, MX1, IRF9, ISG20, IFIT1, IFIT2, IFIT3, IFIT5, PKR, RIG-1, MDA5, NF-κB, TRIF, Tyk2, and IRF7. The one or more inhibitors may be protein inhibitors. The protein inhibitors may be antibodies or artificial antibodies.

siRNA

The invention contemplates that inhibitors of the invention may be siRNA in nature. As used herein, siRNA shall refer to a particular type of isolated double-stranded ribonucleic acid (RNA) molecule characterized by a length of about 21-23 nucleotides, a single-stranded sense (s) strand and a single-stranded antisense (as) strand, wherein the antisense strand has a nucleotide sequence complementary to a target nucleotide sequence, which RNA molecule, when delivered into a cell expressing a protein encoded by the target sequence, reduces the amount of target nucleotide sequence (and the encoded protein) in the cell.

The sense and antisense strands of siRNA have nucleotide sequences which are strictly or at least substantially complementary to each other, such that they can form a stable duplex structure under suitable conditions, in vivo or in vitro. In certain embodiments one or both ends of either strand can extend beyond the corresponding end or ends of the other strand in the duplex structure, thereby allowing short overhanging sequence (generally 1-2 nucleotides long) at either or both ends of the siRNA.

The siRNA will generally include nucleotide subunits having canonical nucleobases common to RNA, e.g., adenine, cytosine, guanine, and uracil, but is not so limited. Other nucleobases, including but not limited to thymine and inosine, can also be present in some embodiments.

Once the nucleotide sequence of a target is known, one of ordinary skill in the art is able to generate suitable siRNA that can inhibit protein production. Methods of generating siRNA to targets is known in the art. The nucleotide sequences of the targets ABCF1, HSP90, CDC37 and TBK1 provided herein and/or are known in the art.

Small Molecule

The invention contemplates that the inhibitors of the invention may be small molecules. The term "small molecule" is art-recognized and refers to a composition which has a molecular weight of less than about 2000 g/mole, or less than about 1000 g/mole, and even less than about 500 g/mole. Small molecules may include, for example, nucleic acids, peptides, peptide nucleic acids, peptidomimetics, carbohydrates, lipids or other organic (carbon containing) or inorganic molecules. Many pharmaceutical companies have extensive libraries of chemical and/or biological mixtures, often fungal, bacterial, or algal extracts, which can be screened with any of the assays of the invention. The term "small organic molecule" refers to a small molecule that is often identified as being an organic or medicinal compound, and does not include molecules that are exclusively nucleic acids, peptides, or polypeptides. In some cases, the small organic molecule is a pharmaceutically active agent (i.e., a drug).

A small molecule may be a non-peptidic, non-oligomeric organic compound either synthesized in the laboratory or found in nature. Small molecules, as used herein, can refer to compounds that are "natural product-like", such as small molecule that are similar in structure to a natural product or are similar with respect to density of stereocenters, density of functional groups, ring systems, 3-D structure, etc.; however, the term "small molecule" is not limited to "natural product-like" compounds and may include compounds that are not based on and are not similar to known natural products. A small molecule may contain several carbon-carbon bonds, although this characterization is not intended to be limiting for the purposes of the present invention.

Diagnosing Aberrant DNA Sensing Pathways and Concomitant Diseases

In some embodiments the invention relates to diagnosing diseases associated with aberrant DNA sensing and/or identifying subjects to be treated based on the presence of one or more markers of aberrant DNA sensing. Certain diagnostics for determining the presence of disease or identifying subjects with aberrant DNA sensing may include: (i) ex vivo stimulation of patient cells (monocyte-derived dendritic cells or skin fibroblasts) with transfected DNA or retrovirus, and measurement of interferon or interferon-stimulated gene (ISG) production; (ii) gene expression of blood cells to look for upregulation of ISGs; (iii) measurement of interferon proteins in peripheral blood serum or cerebrospinal fluid; (iv) stimulation of control cells with patient serum followed by measurement of ISG expression; (v) sequencing of Trex1, Dnase1, Dnase2, Fen1 (DnaseIV), RnaseH2, SAMHD1 or other nucleases and nucleotidases to look for deleterious mutations that result in abnormally increased levels of cytosolic DNA, RNA or components thereof. Other markers are discussed herein as well.

It is to be understood that the samples to be tested according to the foregoing methods may comprise cells and fluids from any region of the body, including but not limited to blood cells, skin cells, non-skin fibroblasts, and the like.

Trex1 Mutation

In some embodiments, a marker of aberrant DNA sensing is a mutation in the Trex1 gene locus. As used herein, a mutation in the Trex1 gene locus refers to a mutation that reduces or eliminates synthesis of the TREX1 protein or that encodes a TREX1 protein with reduced or no nuclease activity. Mutations of interest include those that result in aberrant accumulation of cytosolic DNA, as compared to for example cells having no nuclease mutation. Mutations in the Trex1 locus include point mutations, insertions, deletions, duplications, inversions, translocations, and the like. An example of such a mutation is a missense mutation that results in the amino acid substitution of D18N. Other mutations result in TREX1 amino acid substitutions such as R114H, A158V, G227S, A247P, R240S, P290L, Y305C, G306A, the frame shift (fs) mutations P212fs and D272fs, and the point deletion 979delC in the TREX1 3' UTR. Additional TREX1 mutations are disclosed in published PCT application WO2008/037311 and are incorporated by reference herein.

These and other mutations of interest can be readily identified by one skilled in the art using standard sequencing methodologies. For example, sequencing analysis may be performed on mRNA transcripts or cDNA counterparts (e.g., for coding region mutations) or on genomic DNA (for regulatory and/or coding region mutations). As used herein, regulatory regions are those nucleotide sequences (and regions) that control the temporal and/or spatial expression of a gene but typically do not contribute to the amino acid sequence of the gene product. As used herein, coding regions are those nucleotide sequences (and regions) that dictate the amino acid sequence of the gene product. Assays that can identify protein abnormalities are known in the art and include enzyme-linked immunosorbent assay (ELISA) and other immunological detection methods such as Westerns.

The nucleotide sequences of the human and mouse Trex1 loci are provided in Table 1.

Autoimmune Disorder

The invention contemplates identifying subjects having aberrant DNA sensing pathways and treating such subjects so identified using the methods provided herein. These subjects may have or may be at risk of developing an autoimmune disorder.

As used herein, an autoimmune disorder is a disorder that results when a subject's immune system attacks its own organs or tissues, producing a clinical condition associated with the destruction of that tissue. Examples of autoimmune disorders include but are not limited to systemic lupus erythematosus (SLE), rheumatoid arthritis, psoriatic arthritis, Type 1 immune-mediated or insulin-dependent diabetes mellitus, hemolytic anemias, rheumatic fever, Crohn's disease, Guillain-Barre syndrome, psoriasis, thyroiditis such as chronic thyroiditis and Hashimoto's thyroiditis, Grave's disease, myasthenia gravis, glomerulonephritis, polymyalgia, autoimmune hepatitis, temporal arteritis, cryoglobulinemia, multiple sclerosis, scleroderma, Wegener's granulomatosis, Addison's disease, autoimmune uveitis, autoimmune hemolytic anemia, pernicious anemia, autoimmune thrombocytopenia, temporal arteritis, antiphospholipid syndrome, Behcet's disease, dermatitis herpetiformis, pemphigus vulgaris, vitiligo, ulcerative colitis, primary biliary cirrhosis, autoimmune oophoritis and orchitis, autoimmune disorder of the adrenal gland, polymyositis, dermatomyositis, allograft rejection, autoimmune uveoretinitis, giant cell arteritis, regional enteritis, granulomatous enteritis, distal ileitis, regional ileitis, terminal ileitis, sarcoidosis, spondyloarthropathies such as ankylosing spondylitis, Sjogren's syndrome, familial chilblain lupus (FCL), and retinal vasculopathy with cerebral leukodystrophy (RVCL). Some of these autoimmune disorders are due primarily to the action of T cells and these include insulin-dependent diabetes mellitus, multiple sclerosis and rheumatoid arthritis.

Immune Stimulation/Enhancement

The invention provides methods for stimulating or enhancing an existing immune response in certain subjects under certain situations. Such situations include those in which the subject is in need of an immune response. As an example, the invention contemplates stimulating or enhancing an immune response in a subject that has or is at risk of developing an infection such as a viral infection. As another example, the invention contemplates stimulating or enhancing an immune response is a subject that has cancer or that was previously diagnosed with cancer and may be in remission. As yet another example, the invention contemplates stimulating or enhancing an immune response is a subject that is being vaccinated, including a subject being vaccinated with a DNA or RNA vaccine.

In these embodiments, the invention contemplates administering to such subjects inhibitors of PTPN1 or PPP6C, alone or in combination with each other, and optionally in combination with other active agents.

Infection

As used herein, the term "infection" refers to an abnormal presence of an infectious microbe or infectious agent in a host. An infection with an infectious microbe specifically includes a bacterial, viral, fungal, or parasitic infection, and any combination thereof. A viral infection may be an infection by a DNA virus or an RNA virus.

DNA viruses are defined as viruses in which the genetic material is DNA rather than RNA. The DNA may be either double- or single-stranded. Illustrative DNA viruses include, but are not limited to, the family Poxyiridae, including the genus Orthopoxyirus (Variola major, Variolaminor, Monkey pox Vaccinia, Cowpox, Buffalopox, Rabbitpox, Ectromelia), the genus Leporipoxyirus (Myxoma, Fibroma), the genus Avipoxyirus (Fowlpox, other avian poxyirus), the genus *Capripoxyirus* (sheeppox, goatpox), the genus *Suipoxyirus* (Swinepox), the genus *Parapoxyirus* (contagious postular dermatitis virus, pseudocowpox, bovine papular stomatitis virus); the family Iridoviridae (African swine fever virus, Frog viruses 2 and 3, Lymphocystis virus of fish); the family Herpesviridae, including the alpha-Herpesviruses (Herpes Simplex Types 1 and 2, Varicella-Zoster. Equine abortion virus. Equine herpes virus 2 and 3, pseudorabies virus, infectious bovine keratoconjunctivitis virus, infectious bovine rhinotracheitis virus, feline rhinotracheitis virus, infectious laryngotracheitis virus) the Beta-herpesviruses (Human cytomegalovirus and cytomegaloviruses of swine and monkeys); the gamma-herpesviruses (Epstein-Barr virus (EBV), Marek's disease virus, Herpes saimiri, Herpesvirus ateles, Herpesvirus sylvilagus, guinea pig herpes virus, Lucke tumor virus); the family Adenoviridae, including the genus Mastadenovirus (Human subgroups A, B, C, D, E and ungrouped; simian adenoviruses (at least 23 serotypes), infectious canine hepatitis, and adenoviruses of cattle, pigs, sheep, frogs and many other species, the genus *Aviadenovirus* (Avian adenoviruses); and non-cultivatable adenoviruses; the family Papoviridae, including the genus *Papillomavirus* (Human papilloma viruses, bovine papilloma viruses, Shope rabbit papilloma virus, and various pathogenic papilloma viruses of other species), the genus *Polyomavirus* (polyomavirus, Simian vacuolating agent (SV-40), Rabbit vacuolating agent (RKV), K virus, BK virus, JC virus, and other primate polyoma viruses such as Lymphotmphic papilloma virus); the family Parvoviridae including the genus Adeno-associated viruses, the genus *Parvovirus* (Feline panleukopenia virus, bovine parvovirus, canine parvovirus, Aleutian mink disease virus, etc). Finally, DNA viruses may include viruses which do not fit into the above families such as Kuru and Creutzfeldt-Jacob disease viruses and chronic infectious neuropathic agents (CHINA virus).

RNA Virus

RNA viruses are viruses having genetic material that is RNA rather than DNA. The RNA may be either double- or single-stranded. Illustrative RNA viruses include, but are not limited to *allexivirus* genus, arenaviridae, arteriviridae, astroviridae, avsunviroidae, barnaviridae, *benyvirus* genus, birnaviridae, *bornavirus* genus, bromoviridae, bunyaviridae, caliciviridae, *capillovirus* genus, *carlavirus* genus, closteroviridae, comoviridae, coronaviridae, cricket paralysis virus genus, cystoviridae, *deltavirus* genus, *enamovirus* genus, filoviridae, flaviviridae, *foveavirus* genus, *furovirus* genus, hepatitis E-like virus genus, *hordeivirus* genus, hypoviridae, *idaeovirus* genus, leviviridae, luteoviridae, *marafivirus* genus, metaviridae, namaviridae, nodaviridae, *ophiovirus* genus, orthomyxoviridae, *ourmiavirus* genus, paramyxoviridae, partitiviridae, *pecluvirus* genus, picornaviridae, *pomo-*

*virus* genus, pospiviroidae, potexvirus genus, potyviridae, pseudoviridae, reoviridae, retroviridae, rhabdoviridae, sequiviridae, *sobemovirus* genus, *tenuivirus* genus, tetraviridae, *tobamovirus* genus, *tobravirus* genus, togaviridae, tombusviridae, totiviridae, *trichovirus* genus, *tymovirus* genus, *umbravirus* genus, *varicosavirus* genus, and *vitivirus* genus viruses.

Cancer

"Cancer" as used herein refers to an uncontrolled growth of cells which interferes with the normal functioning of the bodily organs and systems. Cancers which migrate from their original location and seed vital organs can eventually lead to the death of the subject through the functional deterioration of the affected organs. Hemopoietic cancers, such as leukemia, are able to outcompete the normal hemopoietic compartments in a subject, thereby leading to hemopoietic failure (in the form of anemia, thrombocytopenia and neutropenia) ultimately causing death.

A metastasis is a region of cancer cells, distinct from the primary tumor location resulting from the dissemination of cancer cells from the primary tumor to other parts of the body. At the time of diagnosis of the primary tumor mass, the subject may be monitored for the presence of metastases. Metastases are most often detected through the sole or combined use of magnetic resonance imaging (MRI) scans, computed tomography (CT) scans, blood and platelet counts, liver function studies, chest X-rays and bone scans in addition to the monitoring of specific symptoms.

Cancers include, but are not limited to, basal cell carcinoma, biliary tract cancer, bladder cancer; bone cancer; brain and CNS cancer; breast cancer; cervical cancer; choriocarcinoma; colon and rectum cancer; connective tissue cancer, cancer of the digestive system; endometrial cancer, esophageal cancer; eye cancer; cancer of the head and neck; gastric cancer; intra-epithelial neoplasm; kidney cancer; larynx cancer; leukemia; liver cancer; lung cancer (e.g. small cell and non-small cell); lymphoma including Hodgkin's and Non-Hodgkin's lymphoma; melanoma; myeloma; neuroblastoma; oral cavity cancer (e.g., lip, tongue, mouth, and pharynx); ovarian cancer; pancreatic cancer; prostate cancer; retinoblastoma; rhabdomyosarcoma; rectal cancer; renal cancer, cancer of the respiratory system; sarcoma; skin cancer; stomach cancer; testicular cancer; thyroid cancer, uterine cancer; cancer of the urinary system, as well as other carcinomas and sarcomas.

DNA Vaccines

In some embodiments, methods are provided for stimulating or enhancing an immune response to a DNA vaccine. DNA vaccines allow the direct injection of genetic material in the form of DNA, into a subject, thereby causing some cells to produce gene products from the introduced DNA. While not limiting the disclosure to one mechanism of action, it is contemplated that the gene products then illicit immune responses. DNA vaccines can produce robust immune responses in a variety of animal models as well as in humans, as exemplified in Donnelly, et al., Annu. Rev. Immunol. 15:617-648 (1997) and Manickan, et al., Crit. Rev. Immunol: 17(2):139-154 (1997). Methods for generating a DNA vaccine are known in the art, and are exemplified in U.S. Pat. No. 8,263,394 (DNA vaccines directed against HIC polypeptides); U.S. Pat. No. 8,257,713 (DNA vaccines against *Aeromonas hydrophila*); and U.S. Pat. No. 8,278,093 (DNA vaccines against human cytomegalovirus infection).

Subject

As used herein, the term "subject" refers to a human or non-human mammal or animal. Non-human mammals include livestock animals, companion animals, laboratory animals, and non-human primates. Non-human subjects also specifically include, without limitation, horses, cows, pigs, goats, dogs, cats, mice, rats, guinea pigs, gerbils, hamsters, mink, and rabbits. In some embodiments of the invention, a subject is referred to as a "patient." In some embodiments, a patient or subject may be under the care of a physician or other health care worker, including, but not limited to, someone who has consulted with, received advice from or received a prescription or other recommendation from a physician or other health care worker.

Treatment

As used herein, treatment includes preventing a disease or condition from occurring (e.g., in a subject predisposed to such a disease or condition but not manifesting any symptoms associated therewith) or inhibiting a pre-existing disease or condition (e.g., either reducing the disease load or eliminating the disease altogether). The methods of the invention may also be used to reduce or ameliorate symptoms associated with the disease or condition.

Effective Amount, Pharmaceutical Compositions, and Routes of Administration

As described, the agents of the invention, namely agents which modulate or inhibit factors involved in the DNA sensing pathway including but not limited to ABCF1, HSP90, CDC37, and TBK1, are administered in effective amounts. In general, an effective amount is any amount that can cause a beneficial change in a desired tissue. Preferably, an effective amount is that amount sufficient to cause a favorable phenotypic change in a particular condition such as a lessening, alleviation or elimination of the condition as a whole.

In general, an effective amount is that amount of a pharmaceutical preparation that alone, or together with further doses, produces the desired response. This may involve only slowing the progression of the disease temporarily, although more preferably, it involves halting the progression of the disease permanently or delaying the onset of or preventing the disease or condition from occurring. This can be monitored by routine methods. In some embodiments, the effective amount is one that prevents the occurrence or onset of more than one, preferably the majority, and even more preferably all of the markers of the DNA-triggered innate immune response.

Generally, doses of active compounds would be from about 0.01 mg/kg per day to 1000 mg/kg per day. It is expected that doses ranging from 50-500 mg/kg will be suitable, preferably orally and in one or several administrations per day.

Such amounts will depend, of course, on the particular condition being treated, the severity of the condition, the individual patient parameters including age, physical condition, size and weight, the duration of the treatment, the nature of concurrent therapy (if any), the specific route of administration and like factors within the knowledge and expertise of the health practitioner. Lower doses will result from certain forms of administration, such as intravenous administration. In the event that a response in a subject is insufficient at the initial doses applied, higher doses (or effectively higher doses by a different, more localized delivery route) may be employed to the extent that patient tolerance permits. Multiple doses per day are contemplated to achieve appropriate systemic levels of compounds. It is preferred generally that a maximum dose be used, that is, the highest safe dose according to sound medical judgment. It will be understood by those of ordinary skill in the art, however, that a patient may insist upon a lower dose or tolerable dose for medical reasons, psychological reasons or for virtually any other reasons.

The agents of the invention, including but not limited to ABCF1, HSP90, CDC37, and TBK1 inhibitors, may be combined, optionally, with a pharmaceutically-acceptable carrier to form a pharmaceutical preparation. The term "pharmaceutically-acceptable carrier" as used herein means one or more compatible solid or liquid fillers, diluents or encapsulating substances which are suitable for administration into a human. The term "carrier" denotes an organic or inorganic ingredient, natural or synthetic, with which the active ingredient is combined to facilitate the application. The components of the pharmaceutical compositions also are capable of being co-mingled with the molecules of the present invention, and with each other, in a manner such that there is no interaction which would substantially impair the desired pharmaceutical efficacy. In some aspects, the pharmaceutical preparations comprise an agent of the invention in an amount effective to treat a disorder.

The active agents described herein may be used individually or together. When agents are used together (or in conjunction), they may be formulated and thus administered together or they may be formulated separately and administered together or separately.

The pharmaceutical preparations may contain suitable buffering agents, including: acetic acid in a salt; citric acid in a salt; boric acid in a salt; and phosphoric acid in a salt. The pharmaceutical compositions also may contain, optionally, suitable preservatives, such as benzalkonium chloride; chlorobutanol; parabens and thimerosal.

A variety of administration routes are available. The particular mode selected will depend, of course, upon the particular drug selected, the severity of the condition being treated and the dosage required for therapeutic efficacy. The methods of the invention, generally speaking, may be practiced using any mode of administration that is medically acceptable, meaning any mode that produces effective levels of the active compounds without causing clinically unacceptable adverse effects. Such modes of administration include oral, rectal, topical, nasal, interdermal, or parenteral routes. The term "parenteral" includes subcutaneous, intravenous, intramuscular, or infusion. Intravenous or intramuscular routes are not particularly suitable for long-term therapy and prophylaxis. As an example, pharmaceutical compositions for the acute treatment of subjects having a migraine headache may be formulated in a variety of different ways and for a variety of administration modes including tablets, capsules, powders, suppositories, injections and nasal sprays.

The pharmaceutical preparations may conveniently be presented in unit dosage form and may be prepared by any of the methods known in the art of pharmacy. All methods include the step of bringing the active agent into association with a carrier which constitutes one or more accessory ingredients. In general, the compositions are prepared by uniformly and intimately bringing the active compound into association with a liquid carrier, a finely divided solid carrier, or both, and then, if necessary, shaping the product.

Compositions suitable for oral administration may be presented as discrete units, such as capsules, tablets, lozenges, each containing a predetermined amount of the active compound. Other compositions include suspensions in aqueous liquids or non-aqueous liquids such as a syrup, elixir or an emulsion.

Compositions suitable for parenteral administration conveniently comprise a sterile aqueous preparation of the agents of the invention, which is preferably isotonic with the blood of the recipient. This aqueous preparation may be formulated according to known methods using suitable dispersing or wetting agents and suspending agents. The sterile injectable preparation also may be a sterile injectable solution or suspension in a non-toxic parenterally-acceptable diluent or solvent, for example, as a solution in 1,3-butane diol. Among the acceptable vehicles and solvents that may be employed are water, Ringer's solution, and isotonic sodium chloride solution. In addition, sterile, fixed oils are conventionally employed as a solvent or suspending medium. For this purpose any bland fixed oil may be employed including synthetic mono- or di-glycerides. In addition, fatty acids such as oleic acid may be used in the preparation of injectables. Carrier formulation suitable for oral, subcutaneous, intravenous, intramuscular, etc. administrations can be found in Remington's Pharmaceutical Sciences, Mack Publishing Co., Easton, Pa.

Other delivery systems can include time-release, delayed release or sustained release delivery systems. Such systems can avoid repeated administrations of the active compound, increasing convenience to the subject and the physician. Many types of release delivery systems are available and known to those of ordinary skill in the art. They include polymer base systems such as poly(lactide-glycolide), copolyoxalates, polycaprolactones, polyesteramides, polyorthoesters, polyhydroxybutyric acid, and polyanhydrides. Microcapsules of the foregoing polymers containing drugs are described in, for example, U.S. Pat. No. 5,075,109. Delivery systems also include non-polymer systems that are: lipids including sterols such as cholesterol, cholesterol esters and fatty acids or neutral fats such as mono-di- and tri-glycerides; hydrogel release systems; sylastic systems; peptide based systems; wax coatings; compressed tablets using conventional binders and excipients; partially fused implants; and the like. Specific examples include, but are not limited to: (a) erosional systems in which the active compound is contained in a form within a matrix such as those described in U.S. Pat. Nos. 4,452,775, 4,675,189 and 5,736,152, and (b) diffusional systems in which an active component permeates at a controlled rate from a polymer such as described in U.S. Pat. Nos. 3,854,480, 5,133,974 and 5,407,686. In addition, pump-based hardware delivery systems can be used, some of which are adapted for implantation.

Use of a long-term sustained release implant may be desirable. Long-term release, are used herein, means that the implant is constructed and arranged to delivery therapeutic levels of the active ingredient for at least 30 days, and preferably 60 days. Long-term sustained release implants are known to those of ordinary skill in the art and include some of the release systems described above.

Although the present invention and its advantages have been described in detail, it should be understood that various changes, substitutions and alterations can be made herein without departing from the spirit and scope of the invention as defined in the appended claims.

The present invention will be further illustrated in the following Examples which are given for illustration purposes only and are not intended to limit the invention in any way.

EXAMPLES

Materials

Cells, viruses, and reagents. Primary murine lung fibroblasts were derived from lung tissue of 4-8 wk old female C57BL/6 mice as previously described (Barbalat et al., Annu Rev Immunol, 2011, 29: 185-214). p53−/− MEFs were a gift from D. M. Sabatini and D. J. Kwiatkowski (Zhang et al., J Clin Invest, 2003, 112: 1223-1233.). Trex1–/– MEFs and C57BL/6 wild type (wt) control MEFs were a gift from T. Lindahl. Ptpn1–/– MEFs and Ptpn1–/– MEFs rescued with Ptpn1 cDNA were a gift from B. G. Neel (Klaman et al., Mol Cell Biol, 2000, 20:5479-5489). 293T cells were obtained from ATCC. cDCs were prepared from B6.C3H-sst1 (Sp110 LoF) as previously described (Altfeld et al., Nat. Rev. Immunol., 2011, 11: 176-186; Yan et al., Nat Immunol, 2010, 11: 1005-1013). Cells were maintained in DMEM (Mediatech) supplemented with 10% FBS (Sigma). Human monocytes were isolated by negative selection (Life Technologies) from peripheral blood mononuclear cells, and differentiated into dendritic cells by a seven day culture in GM-CSF (R&D) and IL-4 (R&D) in RPMI (Life Technologies) supplemented with 10% FBS (Life Technologies). Sendai virus was obtained from ATCC and used at an MOI of 1. HSV-1 d19 was obtained as a gift from N. A. DeLuca and was used at an MOI of 10 (Samaniego et al., J Virol, 1998, 72: 3307-3320). Self-inactivating minimal HIV-1 virus was produced in 293T cells using the vector pLX301 (TRC, Broad Institute), the packaging construct psPAX2, and the envelope plasmid pCMV-VSVG. Interferon stimulatory DNA (ISD), HIV gag-100, and HSV60 dsDNA were annealed from oligonucleotides (IDT) as described previously (Yan et al., Nat. Rev. Immunol., 2010, 11: 1005-1013; Stetson et al., Immunity, 2006, 24: 93-103; Unterholzner et al., Nat. Rev. Immunol., 2010, 11: 997-1004). Sequences are listed in—Table 1. In vitro transcribed RNA was synthesized as described previously (Hornung et al., Science, 2006, 314: 994-997). Nucleic acids were mixed with Lipofectamine LTX (Life Technologies) at a ratio of 1:3 (wt/vol) in Opti-MEM (Life Technologies), and added to cells at a final concentration of 1 ug/mL (DNA) or 0.1 ug/mL (RNA) unless otherwise indicated. Recombinant IFNβ was obtained from PBL InterferonSource. Murine CXCL10 ELISA kit was obtained from R&D. Antibodies were obtained from the following sources: anti-P-TBK1 Ser172 (5483; Cell Signaling), anti-P-IRF3 Ser396 (4947; Cell Signaling), anti-TBK1 (3504; Cell Signaling), anti-IRF3 (4302; Cell Signaling), anti-CDC37 (4793; Cell Signaling), anti-ABCF1 (SAB2106638, Sigma), anti-HMGB2 antibody (ab67282, Abcam), anti-SET (sc25564, Santa Cruz), anti-IFI24 (SAB2105265, Sigma), anti-α-tubulin (T5168, Sigma), anti-β-actin (ab6276, Abcam), anti-HA (High Affinity 3F1; Roche), Anti-SMARCB1 (H-3, Santa Cruz) and rat IgG control (Jackson Laboratories). PTPN1 inhibitor (CAS 765317-72-4), okadaic acid, and celastrol were obtained from Millipore. BX795 and 17-(Dimethylaminoethyl-amino)-17-demethoxygeldanamycin (17-DMAG) were obtained from Invivogen.

Methods

Identification of DNA-interacting proteins by SILAC mass spectrometry p53–/– MEFs were grown for six cell doublings in DMEM depleted of L-arginine and L-lysine (Caisson Labs Inc.) and supplemented with 10% dialyzed FBS (Sigma) and either light (L), medium (M), or heavy (H) isotope-labeled amino acids. The L and H cells were stimulated with 1000 U/mL IFNβ for 18 h. The cells were pelleted and incubated in hypotonic lysis buffer (10 mM HEPES pH 7.4, 10 mM KCl, 1 mM EDTA) containing protease inhibitors (Roche) for 10 min on ice followed by lysis for 1 min in hypotonic lysis buffer supplemented with 0.3% Triton X-100. Nuclei and insoluble proteins were removed by centrifugation. 11 mg of the H and L lysates were mixed with a 1:1 mix of biotinylated ISD and ISD with a tetraethylene glycol arm between the biotin and the nucleic acid (IDT), and then split into two samples. No ISD was added to 11 mg of sample M. Equal volumes of streptavidin beads (Ultralink; Pierce) were added to all three samples, and samples were rotated for 2.5 h at 4° C. Beads were pelleted and washed extensively with wash buffer (50 mM Tris-HCl pH 7.8, 150 mM NaCl, 1 mM EDTA, 0.75% NP-40, 0.175% sodium deoxycholate). The three samples were mixed, cysteines were reduced by DTT and alkylated with iodoacetamide, and proteins were eluted by heating in SDS sample buffer (Life Technologies) for 10 min before separation on a 4-12% gradient gel (NuPAGE; Life Technologies). The resolved proteins were divided into 13 fractions and subjected to proteolysis with trypsin. Peptide extracts were cleaned up offline with C18 StageTips prior to 90 min nanoESI-LCMS analyses with a gradient of 3%-35% acetonitrile/0.1% formic acid. Protein and peptide identification and quantification was performed with MaxQuant (v. 1.0.12.31) using the IPI mouse v3.52 as the search database. Search parameters specified trypsin cleavage with 2 missed cleavages, peptide mass tolerance of 6 ppm and fragment mass tolerance of 0.5 Da; carbamidomethylated cysteines and variable modifications of oxidized methionine, acetylation of protein N-termini and sample-specific modifications of Arg-0,6,10 and Lys-0,4,8 for SILAC triple labeling. Protein ratios were medians of ratios from at least two quantified peptides. To identify significant proteins, P-values were calculated via Gaussian modeling of the log(H/M) data, and a significance threshold of $P<1\times10^{-4}$ was used.

Identification of ABCF1-interacting proteins by SILAC mass spectrometry. Light (L), medium (M), and heavy (H) isotope-labeled p53–/– MEFs mock infected (L) or stably expressing Abcf1-HA (M and H) were stimulated with 1000 U/mL IFNβ for 18 h. H cells were transfected with ISD for 2.5 h. Cells were lysed in 5 mM Tris-HCl pH 7.8, 150 mM NaCl, 1 mM EDTA, .2% NP-40, and insoluble proteins were removed by centrifugation. 18 mg of each lysate was mixed with 1 ug/mL anti-HA antibody and Protein G beads (Pierce), and rotated for 2.5 h at 4° C. Beads were pelleted and washed extensively with wash buffer (above). The three samples were mixed, cysteines were reduced by DTT and alkylated with iodoacetamide, and proteins were eluted by heating in SDS sample buffer for 1 min before separation on a 4-12% gradient gel. The whole gel lane was cut into 8 slices, proteins were digested inside the gel with trypsin, and peptides were extracted from the gel. Extracted peptides were purified with StageTips and analyzed with a 100 min acquisition method on a Thermo EASY-nLC 1000 UHPLC coupled to a Q Exactive mass spectrometer. Raw data files were processed in MaxQuant (v. 1.2.2.5) using the IPI mouse v3.68 as the search database. All proteins were identified with at least 2 or more unique peptides and quantified with 3 or more ratios. SILAC ratios were normalized over the median of all protein ratios to correct for sample losses between parallel immunoprecipitation steps. To identify significant interactions, P-values were calculated via Gaussian modeling of the log(M/L) and log(H/L) data, and a significance threshold of $P<0.01$ was used.

RNA interference screen. 750 p53–/– MEFs per well were seeded in 96-well plates in 60% DMEM and 40% Opti-MEM. 25 nM siRNA was complexed with 0.5 uL Lipofectamine RNAiMax (Life Technologies) in Opti-MEM, incubated for 12 min at 22° C., and added to the wells. 72 h later, cells were transfected with ISD. 26 h later, supernatants were collected and CXCL1 was quantified by ELISA. Cell viability was estimated by the CellTiter-Glo Luminescent Cell Viability Assay (Promega); CellTiter-Glo values below 3.75e5 were considered toxic. Dharmacon siGENOME SMARTpools from Harvard ICCB were used for screening. ON-TARGETplus Non-targeting Pool was used as negative control (siNeg). Individual siRNAs were from Dharmacon, Life Technologies, Qiagen, and Sigma. siRNA sequences are listed in Table 1.

Plasmid construction. To create the tet-on lentiviral vector (pCW57d-P2AR), the pLKO.1 (Pichlmair et al., Nature, 2012, 487(7408):486-90.) vector was modified as follows: the U6 shRNA cassette was removed from LKO.1 and the TRE with a MCS was inserted upstream of the PGK promoter, the rtTA was cloned 3' of the puroR (with a 2A multicistronic cleavage site between these two genes) along with a WPRE. To create the Abcf1(rescue) construct, silent mutations were made in the siAbcf1(si-1) targeting site using overlap extension PCR; the rescue cDNA was then cloned into pCW57d-P2AR. Renilla-HA was cloned into pCW57d-P2AR as a control. To generate the HA-tagged Abcf1 expression vector, an HA tag was added to the C-terminus of the cDNA during PCR, and the construct was cloned into pLX301. Primer sequences are listed in Table 1. To generate the HA-tagged Sting expression vector, an HA tag was added to the C-terminus of the cDNA during PCR, and the construct was cloned into pLX301.

cDNA rescue. p53−/− MEFs stably expressing cDNA in the pCW57d-P2AR vector were subjected to siRNA. 72 h later, doxycycline (Sigma) at 0, 0.3, 3, or 3 ug/mL was added to the cells, and cells were stimulated with ISD. 26 h later, supernatants were collected and CXCL10 was quantified by ELISA.

Quantitative RT-PCR. Total RNA was prepared from cells using the RNeasy Mini kit (Qiagen). cDNA was synthesized using the High Capacity cDNA Reverse Transcription Kit (Applied Biosystems). Real time qPCR was performed using SYBR Green (Roche) and the LightCycler 480 system (Roche) according to instructions provided by the manufacturer. Relative amounts of mRNA were normalized to Gapdh levels in each sample. The primers used for qPCR are listed in Table 1.

Co-immunoprecipitation assays. p53−/− MEFs stably expressing doxycycline-inducible Abcf1-HA were treated with 3 ug/mL doxycycline for 0, 24, or 48 hours, and then lysed in 1 mM Tris-HCl, 2 mM EDTA. 0.4% NP-40 with complete EDTA-free protease inhibitors (Roche). Anti-HA antibody was crosslinked to Protein G beads (Roche) at a concentration of 1 ug antibody per 20 uL beads using dimethyl pimelimidate dihydrochloride (Sigma). Cleared supernatants were incubated with the antibody-bound beads, and rotated overnight at 4° C. Rat IgG control bound to Protein G were used as IP control with the 48 h doxy-treated lysates. The beads were washed extensively with wash buffer (10 mM Tris-HCl, 2 mM EDTA, 1% NP-40). Immunoprecipitates were eluted with 100 uL 2.5 M Glycine (pH 3) and immediately buffered to pH 7.5 by adding 25 uL of 2 M Tris. Samples were boiled in reducing Laemmli buffer for 10 min, separated by SDS-PAGE, and immunoblotted using anti-HA, anti-SET, and anti-HMGB2 antibodies.

Immunofluorescence assays. $5 \times 10^4$ p53−/− MEFs stably expressing doxycycline-inducible Abcf1-HA were grown overnight on glass coverslips in standard DMEM with 10% FBS. Abcf1-HA expression was induced by adding 3 ug/mL doxycycline for 48 h. Cells were fixed using 4% PFA for 15 min and permeabilized using PBS'0.2% Triton X-100. Cells were then treated with respective primary antibodies at a concentration of 1/200 for 1 h, followed by treatment with respective fluorophore labeled secondary antibodies. The cells were mounted on glass sides using DAPI-containing VECTASHIELD (Vector Laboratories). The cells were visualized using 503 Platform from Intelligent Imaging Innovations, under 40× and 63× oil immersion. 8 Z-stacks were taken per image at 1 um per step and the image were deconvolved using nearest neighbor algorithm. The images were processed using Slidebook version 5.

Network analysis. Network analysis was carried out using PPI data from Ingenuity, the STRING database (http://string.embl.de), and PPIs found experimentally in published studies and in above-described SILAC experiments (Li, Immunity, 2011, 35: 426-440; Boumeester, Nat Cell Biol, 2004, 6: 97-105; Rozenblatt-Rosen et al., Nature, 2012; 487(7408):491-5; (Pichlmair et al., Nature, 2012; Cristea et al., J Virol, 2010, 84: 7803-7814).

Statistics. Statistical significance was determined by Student's t-test.

Lysate preparation. p53−/− MEFs were pelleted and then lysed in panel of lysis buffers. (i) NE-PER (Pierce) was used following manufacturer recommendations to isolate cytoplasmic and nuclear fractions. (ii) Cells were incubated in HLB (10 mM HEPES pH 7.4, 10 mM KCl, 1 mM EDTA) containing protease inhibitors (Roche) for 10 min at 4° C. followed by lysis for 1 min in HLB supplemented with 0.3% Triton X-100. (iii) Cells were incubated in 0.2% NP-40 buffer (50 mM Tris-HCl pH 7.5, 150 mM NaCl, 1 mM EDTA, 0.2% NP-40) for 15 min at 4° C. (iv) Cells were incubated in wash buffer (50 mM Tris-HCl pH 7.8, 150 mM NaCl, 1 mM EDTA, 0.75% NP-40, 0.175% sodium deoxycholate) for 15 min at 4° C. For all lysates, insoluble proteins were removed by centrifugation at 14000 RPM for 10 min at 4° C.

DNA pull-down assays. p53−/− MEFs were stimulated with 1 U/mL interferon-beta (IFNβ) for 18 h or left untreated. Cytoplasmic extracts were prepared using HLB lysis (above). Biotinylated ISD (or buffer alone) and streptavidin beads were added to lysates, and samples were rotated for 2.5 h at 4° C. Beads were pelleted and washed extensively with wash buffer (above). Precipitates were separated by SDS-PAGE, and stained with Coomassie blue (SimplyBlue SafeStain; Life Technologies). For S35-labeled pulldowns, the same protocol was followed, but cells were incubated with 1000 U/mL IFNβ for 6 h and with EXPRESS35S Protein Labeling Mix (Perkin Elmer) in DMEM without methionine (MP Biomedicals) for 2 h before cytoplasmic lysis; bands were visualized by autoradiography after pulldown and SDS-PAGE.

Identification of STING-interacting proteins by SILAC mass spectrometry. Light (L) and heavy (H) isotope-labeled p53−/− MEFs mock infected (L) or stably expressing Sting-HA (H) were stimulated with 1000 U/mL IFNβ for 18 h. H cells were transfected with ISD for 2.5 h. Cells were lysed in 0.2% NP-40 buffer (above), and insoluble proteins were removed by centrifugation. 18 mg of each lysate was mixed with 1 ug/mL anti-HA antibody and Protein G beads (Pierce), and rotated for 2.5 h at 4° C. Beads were pelleted and washed extensively with wash buffer (above). The two samples were mixed, cysteines were reduced by DTT and alkylated with iodoacetamide, and proteins were eluted by heating in SDS sample buffer (Life Technologies) for 10 min before separation on a 4-12% gradient gel. The whole gel lane was cut into 8 slices, proteins were digested inside the gel with trypsin, and peptides were extracted from the gel as described4. Extracted peptides were purified with StageTips5 and analyzed with a 1 min acquisition method on a Thermo EASY-nLC 1000 UHPLC coupled to a Q Exactive mass spectrometer. Survey scans were acquired at a resolution of 70,000 with 1e6 AGC target and 5 ms maximum ion injection time, whereas MS/MS scans were acquired at a 10 resolution of 17,500 with 5e4 AGC target and 120 ms maximum ion injection time. Up to 12 MS/MS scans were triggered in a data dependent mode per duty cycle after peptide isolation with an isolation window of 2.5 m/z and HCD fragmentation at a normalized collision energy of 25. Raw data files were processed in MaxQuant (v. 1.2.2.5)6 using the IPI mouse v3.68 as the search database. All proteins were identified with at least 2 or more unique peptides and quantified with 3 or more ratios. SILAC ratios were normalized over the median of all protein ratios to correct for sample losses between parallel immunoprecipitation steps. To identify significant interactions, P-values were calculated via Gaussian modeling of the log(H/L) data, and proteins with P<0.05 were designated as candidates for siRNA screening.

DNA microarray analysis. (i) 293T cells were stimulated with 1000 U/mL recombinant IFNβ followed by lysis 6 h later in RLT buffer (Qiagen). Total RNA was isolated using the RNeasy Mini kit (Qiagen). Genome-wide gene expression profiling was obtained by hybridizing the RNA to the Affymetrix Human U133 Plus 2.0 array. The cDNA synthesis, labeling, and subsequent hybridization to the microarrays were performed at the Molecular Profiling Laboratory, MGH Center for Cancer Research. (ii) p53−/− MEFs were treated with siRNAs for 72 h and then transfected with ISD. 6 h later, cells were lysed in RLT buffer. Each sample was performed in biological duplicates. Total RNA was isolated using the RNeasy Mini kit. RNA quantification and quality was assessed using Agilent 2100 Bioanalyzer (Agilent Technologies). Genome-wide gene expression profiling was obtained by hybridizing the RNA to the Affymetrix GeneChip® Mouse Gene 1.0 ST Array. The cDNA synthesis, labeling, and subsequent hybridization to the microarrays were performed by the company Expression Analysis (Durham, N.C.).

Curation of microarray data. Genes were curated as follows: (i) Top 340 upregulated genes (>6.1-fold upregulation after stimulation of MEFs with poly(dA-dT)-poly(dT-dA) for 4 h) from GDS17737; (ii) Top 200 upregulated genes (>3.9-fold upregulation after stimulation of NIH3T3 cells with recombinant IFNb for 4 h), and top 300 upregulated genes (>6.25-fold upregulation after stimulation of L929 cells with recombinant IFNb for 4 h) from GSE 144138. (iii) Top 150 upregulated genes (>1.3-fold upregulation after stimulation of 293T cells with recombinant IFNβ for 8 h) from above-described arrays.

Results

Generation of a Candidate Gene Set by Curation and Quantitative Proteomics.

A set of candidate genes were generated from proteomic, genomic, and domain-based datasets that were hypothesized to contain unidentified ISD pathway components (FIG. 1A). First, protein-protein interaction (PPI) datasets were used to select 36 candidate proteins that interacted with the DNA-sensing signaling proteins STING (Ishikawa et al., Nature, 2008, 455: 674-678; Ishikawa et al., Nature, 29, 461: 788-792), TBK1 (Tanaka et al., Sci Signal, 212, 5: ra20, Ishii, Nat Immunol, 2006, 7: 40-48), IKKi (Ishii, Nat Immunol, 2006, 7: 40-48), and IRF3 (Stetson et al., Immunity, 2006, 24: 93-103), from a recent mass spectrometry study (Li, Immunity, 2011, 35: 426-440), as well as 99 discovered candidates from the mass spectrometry-based list of putative STING-interacting proteins (data not shown). Second, 321 DNA- and interferon-stimulated genes (ISGs) were selected from microarray datasets discovered from the methods described herein (Unterholzner et al., Nat. Rev. Immunol., 2010, 11: 997-1004; Tsuchida. Immunity, 2010, 33: 765-776). Third, 126 annotated phosphatases (Gene Ontology (GO):0004721) and 71 deubiquitinases (GO:0004221 and ref. 24) were selected as part of the pilot screen to identify regulators of the ISD pathway (13,23).

As no existing dataset of cytoplasmic DNA-interacting proteins was available, quantitative proteomics was used to discover such proteins. Cytoplasmic extracts were prepared from mouse embryonic fibroblasts (MEFs) (FIG. 8), and added biotinylated 45 base pair double-stranded DNA ('ISD' sequence) coupled to streptavidin beads as bait (Stetson et al., Immunity, 2006, 24: 93-103). Three-state SILAC (stable isotope labeling by amino acids in cell culture) were utilized to label and quantitate peptides using mass spectrometry (Ong et al., Mol Cell Proteomics, 2002, 1: 376-386), with medium isotope-labeled cells used for a negative control (beads alone), light isotope-labeled cells for bead-DNA precipitation, and heavy isotope-labeled cells for bead-DNA precipitation preceded by IFNβ stimulation to upregulate pathway components (FIG. 1B).

While only a handful of bands were visually distinguishable by protein electrophoresis (FIGS. 8B, C), 184 proteins were identified with SILAC ratios that showed enrichment for DNA binding following mass spectrometry (FIGS. 1C and 8D). Among the 184 proteins, 121 (64.2%) were classified by Gene Ontology as having nucleic acid binding function (P=5.95×10$^{-58}$; GO:0003676), and others were components of DNA-binding complexes.

In total, twenty of the identified proteins (10.9%) represent the majority of players involved in the immune sensing of cytosolic DNA (FIG. 1D). Components of DNA sensing pathways were identified including: the HMGB family proteins (HMGB1, HMGB2, HMGB3) (Yanai et al, Nature, 2009, 462: 99-103), components of the AIM2 inflammasome (IFI202B and the HMGB proteins) (Yanai et al, Nature, 2009, 462: 99-103; Roberts, Science, 2009, 323: 1057-1060), and the cytosolic RNA polymerase III complex (POLR3A, POLR3B, POLR3C, POLR3D, POLR3E, POLR3F, POLR3G, POLR3H, POLR1C, POLR1D, POLR2E, POLR2H, and CRCP). Three members of the SET complex (TREX1, APEX1, and HMGB2) were identified that regulate the ISD pathway as well as HIV-1 detection and infection Yan et al., Nat Immunol, 2010, 11: 1005-1013; Stetson et al., Cell, 2008, 134: 587-598; Yanai et al, Nature, 2009, 462: 99-103; Yan et al., PLoS Pathog, 2009, 5: e1000327). Also identified, were associated proteins responsible for the autoimmune disorder, Aicardi-Goutières syndrome (SAMHD1 and TREX1 (Crow et al., Nat Genet, 2006, 38: 917-920; Rice et al., Nat Genet, 2009, 41: 829-832), which are involved in regulating retroviral and retroelement detection (Stetson et al., Cell, 2008, 134: 587-598; Laguette, Trends Immunol, 2012, 33: 26-33). These findings validate the utility of quantitative mass spectrometry as an approach to find candidate components of cytosolic DNA sensing pathways.

High-Throughput Loss-of-Function Screening of Candidates and Network Analysis.

In total, a list of 809 proteomic, genomic, or domain-based candidates were generated to test as potential components of the ISD pathway. A robust high-throughput siRNA (small interfering RNA) screening assay (FIG. 9A) was developed in which genes were knocked down in MEFs, the wells were stimulated with transfected dsDNA (ISD), and production of the IFN-inducible protein, CXCL10, was measured by ELISA (FIG. 2A). Cell survival was measured after knockdown to control for cytotoxic effects of siRNA knockdown. The averages of triplicate wells are shown in FIG. 2B (also data not shown). Knockdown of selected hits was confirmed by qRT-PCR (FIG. 9B).

Positions for selected hits in the ISD pathway described by bringing together information from discovered and given PPI datasets (FIG. 2C) (Li et al., Immunity, 2011, 35: 426-440; Boumeester et al., Nat Cell Biol, 2004: 97-105). The knockdown phenotypes of several of the screening hits were then validated using targeted knockouts, cDNA rescue, and chemical inhibition, as further described.

Validation by Targeted Knockout, cDNA Rescue, and Chemical Inhibition

The ISD signaling pathway was divided broadly into three main processes: DNA sensing, primary signaling, and secondary (IFN) signaling (FIG. 2C). At the level of DNA sensing, several of the discovered cytoplasmic DNA-interacting mass spectrometry hits were found to have functional phenotypes in the siRNA screen, including Hmgb2 and Abcf1 (data not shown). HMGB2 is a nucleic acid sensing pathway member that interacts with DNA (Yanai et al, Nature, 2009, 462: 99-103). Knockout of Hmgb2 reduced ISD-induced Ifnb1 and Cxcl10 production 2-3 fold (FIG. 10A), consistent with the role of Hmgb2 in the response to B-DNA (poly(dA-dT)-poly(dT-dA)) which stimulates the ISD and RNA polymerase III pathways (Yanai et al, Nature, 2009, 462: 99-103; Chiu et al., Cell, 2009, 138: 576-591; (Ablassar et al, Nat Immunol, 2009, 1: 1065-1072). The Abcf1 phenotype was validated using additional siRNAs and cDNA rescue. Using 14 different siRNAs targeting Abcf1, Abcf1 mRNA expression was measured as well as CXCL10 induction in response to ISD stimulation. Knockdown of Abcf1 correlated with CXCL10 induction ($R^2$=0.62), with the screening siRNA pool (si-0) and two other siRNAs (si-1 and -2) inhibiting both Abcf7 mRNA and protein expression and CXCL10 induction most strongly (FIG. 3A). The strongest Abcf1 siRNA (si-1) was validated by cDNA rescue. First an siRNA-resistant cDNA (Abcf7 (rescue) gene was created (FIG. 3B). This cDNA was cloned into a tet-on lentiviral vector (FIG. 3B), the construct was transduced into MEFs, and siRNA-mediated knockdown was repeated in the presence of varying amounts of doxycycline to titrate the expression of the cDNA. The cells were stimulated with ISD and CXCL10 production was read out by ELISA. Knockdown of Abcf1 reduced CXCL10 production by 14.9-fold (P<0.01; FIG. 3C). Expression of Abcf1 (rescue) cDNA, but not of a *Renilla* cDNA control, significantly rescued this phenotype in a dose-dependent manner (P<0.001; FIG. 3C and FIG. 10C).

Abcf1 is a cytosolic and ER-localized member of the ATP-Binding Cassette (ABC) family of transporters with a role in translational control (Paytubi et al., Biol Chem, 2009, 284: 24061-24073), but unlike other members of this family, the Abcf subfamily genes lack transmembrane domains. Although a role in DNA sensing had not been previously observed, there is evidence that human polyomavirus 6 and 7 proteins interact with ABCF1 (Rozenblatt-Rosen et al., Nature, 2012; 487(7408):491-5), suggesting that this DNA virus may derive a benefit from targeting this node (FIG. 2C).

In the primary signaling network (FIG. 2C), components such as Sting, Tbk1, and Irf3 were strong hits in the screen; knockdown of these genes reduced ISD-stimulated CXCL10 production by more than 10-fold each (data not shown), validating the assay. Several screening hits that were hypothesized to interact with these proteins were also found to have phenotypes in the loss-of-function screen, including Cdc37, Numa1, and Cyb5r3 (FIG. 2C). Knockdown of Cdc37 reduced ISD-stimulated CXCL1 production as strongly as the known components (data not shown). Consistent with this result, treatment of murine or human cells with celastrol, a small molecule inhibitor of the CDC37-HSP90 interaction (Zhang et al., Mol Cancer Ther, 2008, 7: 162-170; (Gray et al., Nat Rev Cancer, 2008, 8: 491-495), potently reduced Ifnb1 and CXCL10 induction (FIG. 4A and FIG. 11A). CDC37 is a molecular chaperone that interacts with HSP90 to stabilize specific proteins, notably protein kinases (Gray et al., Nat Rev Cancer, 2008, 8: 491-495), and is a putative interactor of TBK1 (Li et al., Immunity, 2011, 35: 426-440; Boumeester et al., Nat Cell Biol, 2004: 97-105).

The ability of CDC37 to regulate TBK1 expression was tested. Knockdown of Cdc37 substantially reduced protein levels of TBK1 (FIG. 4B). As expected from this result, knockdown of Cdc37 abrogated phosphorylated (serine-172) TBK1 and phosphorylated (serine-396) IRF3—hallmarks of the ISD pathway's activation—following ISD stimulation (FIG. 4B).

Chemical inhibition of HSP90 (by 17-DMAG) or of TBK1 (by BX795) had similar phenotypes as CDC37 inhibition (FIG. 4B and FIG. 11B). Thus, targeting the members of this complex with small molecules may block the ISD response by inhibiting TBK1 protein levels or activity, a phenotype that may be applicable to the treatment of certain autoimmune disorders (see below).

Secondary signaling downstream of the IFN receptor (FIG. 2C) is also important in the ISD response, and we identified known (e.g. Irf9 and Stat1) and previously unknown candidate mediators (e.g. Ptpn1 (Myers et al., J biol Chem, 2001, 276: 47771-47774)) of the secondary signaling network (FIGS. 2C and 11B). Knockout of the protein tyrosine phosphatase, PTPN1, increased ISD-induced CXCL10 production 2.4-fold (FIG. 4C and FIG. 11C), validating the screening phenotype. Consistent with this result, small molecule inhibition of PTPN1 increased CXCL10 production 9.1-fold in human MoDCs stimulated with ISD (FIG. 4D).

Finally, hits were tested in which the molecular interaction partners in the ISD pathway remain unclear. SP110 is an IFN-regulated nuclear body protein, and a natural genetic variation in Sp110 (Pan et al., Nature, 2005, 434: 767-772) led to decrease in DNA-stimulated Ifnb1 induction 1.5-3 fold (FIG. 11D). The protein serine/threonine phosphatase, PPP6C, is a candidate interactor of IκB-ε (Boumeester et al., Nat Cell Biol, 2004: 97-105), but its target in the ISD pathway is unknown. Consistent with the siRNA-induced screen phenotype, small molecule inhibition of PPP6C increased ISD-stimulated CXCL10 production in human MoDCs 2.6-fold. (FIG. 4D).

Targeting the two inhibitory phosphatases, PTPN1 and PPP6C, by small molecules may serve as a way to enhance the immune response to certain DNA viruses and retroviruses (as described herein), and possibly to enhance the immunogenicity of DNA vaccines (Ishikawa et al., Nature, 2009, 461: 788-792; Ishii, Nature, 2008, 451: 725-729).

Quantitative Proteomics Analysis of the DNA-sensing Network

It was further sought to understand the DNA-sensing network (FIG. 2C) by determining the interaction partners of ABCF1, having found that this protein regulates the ISD response (FIG. 2B) and associates with DNA (FIG. 1C and FIG. 8D). Again, an unbiased quantitative mass spectrometry-based approach was used in which we precipitated stably-expressed ABCF1-HA in MEFs with anti-HA antibody and performed SILAC mass spectrometry (FIG. 5A). 53 proteins were identified with SILAC ratios that demonstrated co-precipitation with ABCF1 at a P-value <0.01

(FIG. 5A). Three of the proteins that co-precipitated with ABCF1—SET, HMGB2, and ANP32A—are members of the ER-associated SET complex (FIG. 5B,C), of which HMGB2 was previously isolated, and the DNA exonucleases TREX1 and APEX1 by DNA precipitation (FIG. 1C, D). None of these interactions were seen with STING-HA pulldown (data not shown), indicating specificity for ABCF1. Immunofluorescence showed that ABCF1 colocalized with SET, further supporting the interaction between ABCF1 and the SET complex (FIG. 5D).

The SET complex member, HMGB2 may function as a co-ligand for nucleic acid sensors though the precise role of HMGB2 has remained unclear (Yanai et al, Nature, 2009, 462: 99-103). It was observed that not only HMGB2, but also IFI24—a predicted DNA sensor also known as IFI16 (Unterholzner et al., Nat. Rev. Immunol., 2010, 11: 997-1004)—was a candidate interactor of ABCF1 (FIGS. 5B and C). The experiments show that that ABCF1 may interact with HMGB2, IFI16, and the SET complex.

Consistent with the functions of Hmgb2 and Ifi16 (Unterholzner et al., Nat. Rev. Immunol., 2010, 11: 997-1004; Yanai et al, Nature, 2009, 462: 99-103), knockdown of Abcf1 suppressed TBK1 and IRF3 phosphorylation in MEFs stimulated with ISD (FIG. 5E and FIG. 12A). While Abcf1 knockdown significantly reduced Ifnb1 and ISG induction following dsDNA (HIV gag-100 sequence) stimulation or HSV-1 d109 infection (FIGS. 5F,G and 12B,C), Abcf1 knockdown did not have a significant effect on IFN or ISG induction by Sendai virus (which stimulates the RIG I pathway) or by recombinant IFNβ itself (FIGS. 5G,H, and 12D). These results show that ABCF1 may be a critical node in the DNA sensing network.

Innate Immune Response to Retroviral Infection in Trex1−/− Cells

Whether these finds were relevant to Trex1-dependent autoimmunity and retroviral infection was further examined. While in culture Trex1−/− cells may not spontaneously produce type I IFNs or ISGs, retroviral infection of these cells induces IFN and ISG production in the absence of Trex1 (FIG. 13A and (Yan et al., Nat Immunol, 2010, 11: 1005-1013). Major screening hits were knocked down in Trex1−/− MEFs and infected the cells with an HIV-based retrovirus. Knockdown of 4 of these genes (i.e. Ptpn1, Tiparp, Mdp1, and Ppp6c) significantly enhanced the ability of retroviral infection to induce IFN and ISG production ($P<0.05$), while knockdown of 12 of these genes (including Abcf1 and Cdc37) as well as 4 known signal transduction components (i.e. Trim56, Sting, Tbk1, and Irf3) significantly abrogated the immune response ($P<0.05$; FIG. 6A-C and FIG. 13B).

Figure 6A:
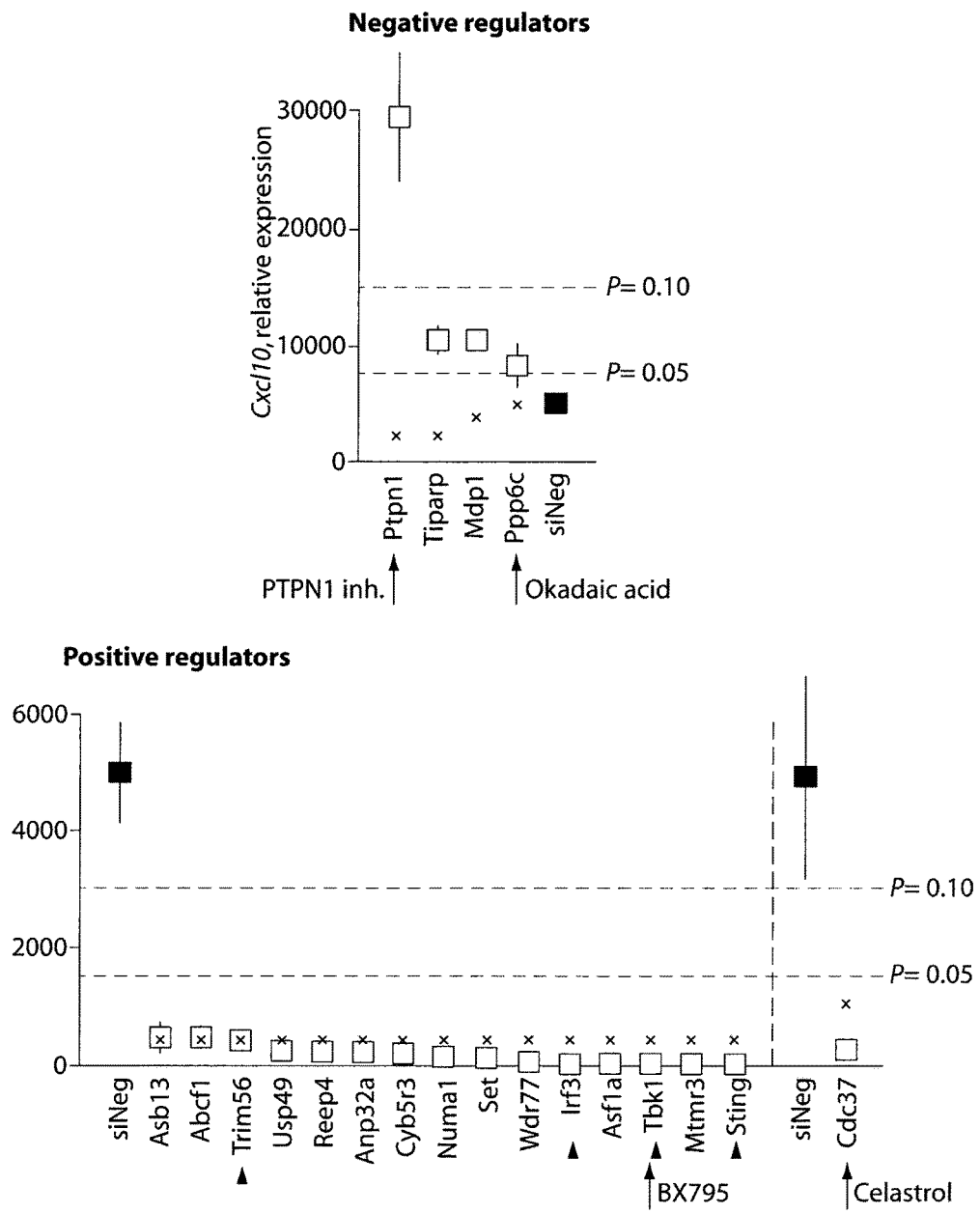
Figure 6B:
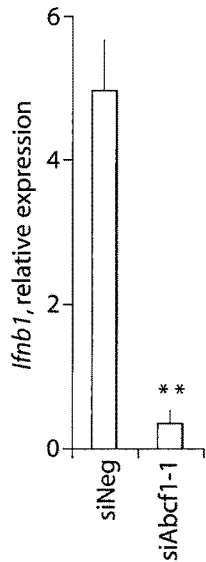
Figure 6C:
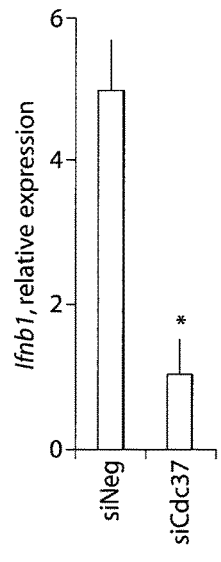
Figure 6D:
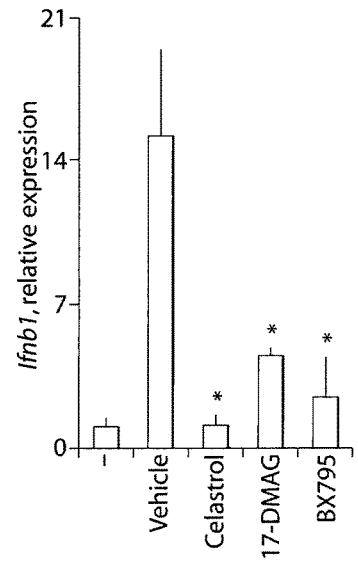
Figure 6E:
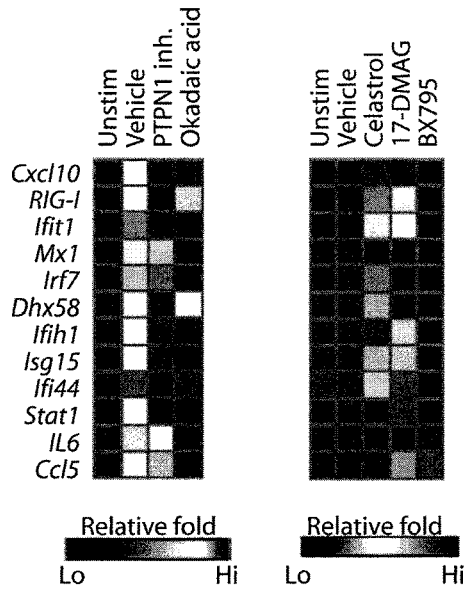

Chemical inhibition of CDC37, HSP90, or TBK1 potently abrogated retroviral infection-induced Ifnb1 induction in Trex1−/− MEFs (FIGS. 6D,E and FIG. 13C). In contrast, chemical inhibition of PTPN1 or PPP6C increased ISG induction in response to retroviral infection in a dose-dependent manner (FIG. 6E and FIG. 13C). Thus, celastrol, 17-DMAG, and BX795 may be therapeutic leads in Trex1-dependent autoimmune disorders, while PTPN1 inhibitor and okadaic acid may exacerbate the autoimmune phenotype but may enhance the innate immune response to retroviral infection.

Human Patient Cells

Human fibroblasts were cultured from a healthy control and a patient with Aicardi-Goutieres syndrome (AGS) who was compound heterozygote for mutations in the Trex1 gene (R114H/D201ins). Cells were treated with vehicle alone or small molecule inhibitors and infected with retrovirus (FIG. 7). Induction levels of Mx1 were determined by qRT-PCR. Data was graphed as averages of triplicate wells (FIG. 7). Small molecules were used at: 500 nM celastrol, 100 nM 17-DMAG, and 500 nM BX795 (FIG. 7).

Discussion

The approach described herein integrated complementary genomic and proteomic datasets to identify new components and physical interactions in the ISD signaling network. DNA-protein interaction, protein-protein interaction, and loss-of-function screening datasets were generated and used to identify new ISD pathway components; validated several of the newly identified components; demonstrated that a subset also function in the response to retroviral infection in Trex1−/− cells; and showed that small molecule inhibitors of several of these components can modulate the innate immune response to dsDNA and retroviral infection.

In the DNA precipitation experiment, 184 candidate cytoplasmic DNA-interacting proteins where identified that encompass most of the published components of DNA-sensing pathways (including ISD, RNA polymerase III, AIM2 inflammasome, and AGS proteins), with several exceptions (e.g. AIM2 and DDX41 which may be specific to cells of the monocyte lineage (Zhang et al., Nat Immunol, 2011, 12: 959-965; Schroder et al., Cell, 2010, 14: 821-832). After screening the candidates for a potential role in the ISD response, we identified ABCF1 as a cytoplasmic protein that associates with dsDNA, IFI16, and HMGB2, and regulates the interferon response to transfected dsDNA and retroviral infection. These results implicate ABCF1 as a key component of the ISD pathway.

The experiments also identified SET complex members (SET, ANP32A, and HMGB2) as ABCF1 interactors. The SET complex contains three DNA nucleases (TREX1, APEX1, and NME1); the chromatin-modifying proteins SET and ANP32A; and HMGB2, which functions as a co-receptor for nucleic acid receptors among other roles (Chowdhury et al., Anuu Rev Immunol, 2008, 26: 389-420). The interactions which were observed among dsDNA, ABCF1, HMGB2, and other SET complex members show that early steps in DNA recognition may occur at the ER-localized SET complex. Consistent with this hypothesis, the complex member TREX1 may prevent HIV-1 DNA detection, and its absence may result in accumulation of retroelement DNA at the ER which drives an ISD response (Yan et al., Nat Immunol, 2010, 11: 1005-1013; Stetson et al., Cell, 2008, 134: 587-598; Yang et al., Cell, 2007, 131: 873-886). Furthermore, the complex members SET and NME1 may also detect HIV-1 DNA, and in turn regulate HIV-1 infectivity (Yan et al., PLoS Pathog, 2009, 5: e1000327). A recent model suggests that the SET complex may recognize viral DNA as damaged DNA, specifically via its base excision repair (BER) activity and/or its distorted structure (e.g. HMGB2) (Yan, Proc Natl Acad Sci USA, 2011, 108: 9244-9249). Consistent with this model, it was found that ISD interactors include the SET and BER complex member, APEX1, as well as nearly the entire BER complex (e.g. PARP1, PARP2, POLB, LIG3, XRCC1, FEN1, and PCNA). These results suggest that the SET complex plays a central role in DNA sensing and forms a coordinated system for detecting, modifying, and degrading viral or retroelement DNA.

The impact of small molecule inhibitors on the DNA-sensing response was tested. It was found that inhibition of PTPN1, PPP6C, CDC37, HSP90, or TBK1 modulates the innate immune response to cytosolic DNA in human dendritic cells and to retroviral infection in Trex1-deficient cells. Current treatments for Trex1-dependent autoimmune disorders, such as Aicardi-Goutieres syndrome and familial chilblain lupus, do not target the cause of these diseases. Small molecules like celastrol, 17-DMAG and BX795 that inhibit the ISD response represent new therapeutics for this class of disorders.

Other Embodiments

While several embodiments of the present invention have been described and illustrated herein, those of ordinary skill in the art will readily envision a variety of other means and/or structures for performing the functions and/or obtaining the results and/or one or more of the advantages described herein, and each of such variations and/or modifications is deemed to be within the scope of the present invention. More generally, those skilled in the art will readily appreciate that all parameters, dimensions, materials, and configurations described herein are meant to be exemplary and that the actual parameters, dimensions, materials, and/or configurations will depend upon the specific application or applications for which the teachings of the present invention is/are used. Those skilled in the art will recognize, or be able to ascertain using no more than routine experimentation, many equivalents to the specific embodiments of the invention described herein. It is, therefore, to be understood that the foregoing embodiments are presented by way of example only and that, within the scope of the appended claims and equivalents thereto, the invention may be practiced otherwise than as specifically described and claimed. The present invention is directed to each individual feature, system, article, material, kit, and/or method described herein. In addition, any combination of two or more such features, systems, articles, materials, kits, and/or methods, if such features, systems, articles, materials, kits, and/or methods are not mutually inconsistent, is included within the scope of the present invention.

All definitions, as defined and used herein, should be understood to control over dictionary definitions, definitions in documents incorporated by reference, and/or ordinary meanings of the defined terms.

The indefinite articles "a" and "an," as used herein in the specification and in the claims, unless clearly indicated to the contrary, should be understood to mean "at least one."

The phrase "and/or," as used herein in the specification and in the claims, should be understood to mean "either or both" of the elements so conjoined, i.e., elements that are conjunctively present in some cases and disjunctively present in other cases. Multiple elements listed with "and/or" should be construed in the same fashion, i.e., "one or more" of the elements so conjoined. Other elements may optionally be present other than the elements specifically identified by the "and/or" clause, whether related or unrelated to those elements specifically identified. Thus, as a non-limiting example, a reference to "A and/or B", when used in conjunction with open-ended language such as "comprising" can refer, in one embodiment, to A only (optionally including elements other than B); in another embodiment, to B only (optionally including elements other than A); in yet another embodiment, to both A and B (optionally including other elements); etc.

As used herein in the specification and in the claims, "or" should be understood to have the same meaning as "and/or" as defined above. For example, when separating items in a list, "or" or "and/or" shall be interpreted as being inclusive, i.e., the inclusion of at least one, but also including more than one, of a number or list of elements, and, optionally, additional unlisted items. Only terms clearly indicated to the contrary, such as "only one of" or "exactly one of," or, when used in the claims, "consisting of," will refer to the inclusion of exactly one element of a number or list of elements. In general, the term "or" as used herein shall only be interpreted as indicating exclusive alternatives (i.e. "one or the other but not both") when preceded by terms of exclusivity, such as "either," "one of," "only one of," or "exactly one of."

As used herein in the specification and in the claims, the phrase "at least one," in reference to a list of one or more elements, should be understood to mean at least one element selected from any one or more of the elements in the list of elements, but not necessarily including at least one of each and every element specifically listed within the list of elements and not excluding any combinations of elements in the list of elements. This definition also allows that elements may optionally be present other than the elements specifically identified within the list of elements to which the phrase "at least one" refers, whether related or unrelated to those elements specifically identified. Thus, as a non-limiting example, "at least one of A and B" (or, equivalently, "at least one of A or B," or, equivalently "at least one of A and/or B") can refer, in one embodiment, to at least one, optionally including more than one, A, with no B present (and optionally including elements other than B); in another embodiment, to at least one, optionally including more than one, B, with no A present (and optionally including elements other than A); in yet another embodiment, to at least one, optionally including more than one, A, and at least one, optionally including more than one, B (and optionally including other elements); etc.

It should also be understood that, unless clearly indicated to the contrary, in any methods claimed herein that include more than one step or act, the order of the steps or acts of the method is not necessarily limited to the order in which the steps or acts of the method are recited.

The invention is further described by the following numbered paragraphs:

1. A method comprising
measuring presence or level of a DNA sensing pathway marker in a subject, and
administering to a subject having an aberrant level of the DNA sensing pathway marker an effective amount of an active agent selected from the group consisting of an ABCF1 inhibitor, an HSP90 inhibitor, a CDC37 inhibitor, and a TBK1 inhibitor, or a combination thereof.

2. A method comprising
administering to a subject, identified as having an aberrant level of a DNA sensing pathway marker, an effective amount of an active agent selected from the group consisting of an ABCF1 inhibitor, an HSP90 inhibitor, a CDC37 inhibitor, and a TBK1 inhibitor, or a combination thereof.

3. The method of claim 1 or 2, wherein the DNA sensing pathway marker is aberrant interferon-stimulated gene (ISG) expression, a Trex1 mutation, a Dnase1 mutation, a Dnase2 mutation, a Fen1 (DnaseIV) mutation, RnaseH2 mutation, or an SAMHD1 mutation.

4. The method of any one of claims 1-3, wherein the active agent is an ABCF1 inhibitor.

5. The method of any one of claims 1-3, wherein the active agent is an HSP90 inhibitor.

6. The method of any one of claims 1-3, wherein the active agent is a CDC37 inhibitor.

7. The method of any one of claims 1-3, wherein the active agent is a TBK1 inhibitor.

8. The method of any one of claims 1-7, wherein the ABCF1 inhibitor, the HSP90 inhibitor, the CDC37 inhibitor, or the TBK1 inhibitor is a small molecule.

9. The method of any one of claims 1-7, wherein the ABCF1 inhibitor, the HSP90 inhibitor, the CDC37 inhibitor, or the TBK1 inhibitor is an siRNA.

10. The method of any one of claims 1-7, wherein the HSP90 inhibitor is 17-DMAG, 17-AAG, or geldanamycin.

11. The method of any one of claims 1-7, wherein the CDC37 inhibitor is celastrol.

12. The method of any one of claims 1-7, wherein the TBK1 inhibitor is BX795 or MRT67307.

13. The method of any one of claims 1-12, wherein the active agent is administered prior to the onset of symptoms associated with an autoimmune disorder.

14. A method for treating a subject having Aicardi-Goutieres syndrome (AGS) comprising
administering to said subject an effective amount of an ABCF1 inhibitor, an HSP90 inhibitor or a CDC37 inhibitor, or a combination thereof.

15. A method for treating a subject having familial chilblain lupus (FCL) comprising
administering to said subject an effective amount of an ABCF1 inhibitor, an HSP90 inhibitor, a CDC37 inhibitor, or a TBK1 inhibitor, or a combination thereof.

16. A method for treating a subject having retinal vasculopathy with cerebral leukodystrophy (RVCL) comprising
administering to said subject an effective amount of an ABCF1 inhibitor, an HSP90 inhibitor, a CDC37 inhibitor, or a TBK1 inhibitor, or a combination thereof.

17. The method of any one of claims 14-16, wherein the subject carries a Trex1 mutation.

18. The method of any one of claims 14-17, wherein the ABCF1 inhibitor, the HSP90 inhibitor, the CDC37 inhibitor, or the TBK1 inhibitor is a small molecule.

19. The method of any one of claims 14-17, wherein the ABCF1 inhibitor, the HSP90 inhibitor, the CDC37 inhibitor, or the TBK1 inhibitor is an siRNA.

20. The method of any one of claims 14-17, wherein the HSP90 inhibitor is 17-DMAG, 17-AAG, geldanamycin, or ganetespib.

21. The method of any one of claims 14-17, wherein the CDC37 inhibitor is celastrol.

22. The method of any one of claims 14-17, wherein the TBK1 inhibitor is BX795 or MRT67307.

23. A method for stimulating an immune response in a subject comprising
administering to a subject an effective amount of a PTPN1 inhibitor, a PPP6C inhibitor, or a combination thereof.

24. The method of claim 23, wherein the subject has a viral infection.

25. The method of claim 24, wherein the viral infection is a retroviral infection.

26. The method of claim 25, wherein the retroviral infection is an HIV infection.

27. The method of claim 24, wherein the viral infection is an infection with a DNA virus.

28. The method of claim 27, wherein the DNA virus is HSV.

29. The method of claim 23, wherein the subject has cancer.

30. The method of claim 23, wherein the PTPN1, the PPP6C inhibitor of the combination thereof is used in combination with a DNA vaccine.

31. The method of any one of claims 23-30, wherein the immune response is an innate immune response.

32. The method of any one of claims 23-31, wherein the PTPN1 inhibitor is 3-(3,5-Dibromo-4-hydroxy-benzoyl)-2-ethyl-benzofuran-6-sulfonicacid-(4-(thiazol-2-ylsulfamyl)-phenyl)-amide.

* * *

Having thus described in detail preferred embodiments of the present invention, it is to be understood that the invention defined by the above paragraphs is not to be limited to particular details set forth in the above description as many apparent variations thereof are possible without departing from the spirit or scope of the present invention.

TABLE 1

Sequences

DNA ligands

| Name | Sequences | |
|---|---|---|
| ISD | 5'-TACAGATCTACTAGTGATCTATGACTGTACATGATCTACA-3' | (SEQ ID NO: 1) |
| | 5'-TGTAGATCATGTACAGATCAGTAGATCACTAGTAGATCTGTA-3' | (SEQ ID NO: 2) |
| HIV gag-100 | 5'-ATGGTTGTAGCTGTCCCAATATTTGTCTACAGCCTTCTGATGTCTAAAAGACCAGGATTAACTGCGAATCGTTCTAGCTCCCTGCTTACCACTACTA-3' | (SEQ ID NO: 3) |
| | 5'-ATAGTATGGGTAAGCAGTGGAGCTAGAACAATATTGGACAGTTAATCGCAGTTAATCCTGGTCTTTTAGAGACCATCAGAAGGCTGTAGACAAATCTGTTTGTAAAATTTATTAAGGGTACAACAT-3' | (SEQ ID NO: 4) |
| HSV60 | 5'-TAAGACACGATGCGATAAAATCTGTTTGTAAAATTTATTAAGGGTACAAATTGCCCTAGC-3' | (SEQ ID NO: 5) |
| | 5'-GCTAGGGCAATTTGTACCCTTAATAAATTTTACAAACAGATTTTATCGCATCGTGTCTTA-3' | (SEQ ID NO: 6) |
| 5'-biotin-SD | 5'-biotin-TACAGATCTACTAGTGATCTATGACTGTACATGATCTACA-3' | (SEQ ID NO: 7) |
| | 5'-TGTAGATCATGTACAGATCAGTAGATCACTAGTAGATCTGTA-3' | (SEQ ID NO: 8) |
| 5'-biotin-ISD-Ad1 | 5'-Biotin-TGAAGTCATGTGTGTATATCACACTGTGATATCACACATGACTTCA-3' | (SEQ ID NO: 9) |
| | 5'-CCATGAAGTCTAGCCACATGCAGTGTGATATCACACATGACTTCA-3' | (SEQ ID NO: 10) |
| 5'-biotin-ISD-act2 | 5'-Biotin-GTGGCTCCATCCTGGCCTCACTGTCCACCTTCCAGCAGATGTGGA-3' | (SEQ ID NO: 11) |
| | 5'-TCCACATCGTCTGCTGAAGGTGGACAGTGAGGCCAGGATGGAGCCAC-3' | (SEQ ID NO: 12) |
| 5'-biotin-gag-100 | 5'-biotin-ATGGTTGTAGCTGTCCCAATATTTGTCTACAGCCTTCTGATGTCTAAAAGACCAGGATTAACTGCGAATCGTTCTAGCTCCCTGCTTACCCATACTA-3' | (SEQ ID NO: 13) |
| | 5'-ATAGTATGGGTAAGCAGGGAGCTAGAACGATTCGCAGTTAATCCTGGTCTTTTAGAGACATCAGAAGGCTGTAGACAAATATTGGGACAGCTACAACCAT-3' | (SEQ ID NO: 14) | siRNA Sequences

| Species | Gene | GeneID | Sense sequence | Notes | SEQ ID NO |
|---|---|---|---|---|---|
| Mo | Abcf1 | 224742 | Dharmacon siGENOME SMARTpool | si-0 | 15 |
| Mo | Abcf1 | 224742 | 5'-AGGAAGUCCUGACUCGAAA-3' | si-1 | 16 |
| Mo | Abcf1 | 224742 | 5'-CGATGATAGTGATGAGAGA-3' | si-2 | 17 |
| Mo | IRF3 | 54131 | 5'-CCGACAAGCUUGUGAAGGA-3' | | 18 |
| Mo | Cdc37 | 12539 | 5'-GCGCCAAGCUGCGAAUUAGA-3' | | 19 |
| Mo | Ptpn1 | 19246 | 5'-GACCACAGUCCAGCGAUUAAAU-3' | | 20 |
| Mo | Tiparp | 99929 | 5'-GAAACAUCACCGUAUUG-3' | | 21 |
| Mo | Mdp1 | 67881 | 5'-AACGUUAACUCAAGGAUUA-3' | | 22 |
| Mo | Ppp6c | 67857 | 5'-GCACGAAGGCUAUAAGUUU-3' | | 23 |
| Mo | Asb13 | 142688 | 5'-UAGAGAAAGUCGCCAAGUU-3' | | 24 |
| Mo | Trim56 | 384309 | 5'-GAAGCCAACAUUGCGCUCUG-3' | | 25 |
| Mo | Usp49 | 224836 | 5'-GACCUGAAGUUGCUGAGAA-3' | | 26 |
| Mo | Reep4 | 72549 | 5'-GAUGAUCUGUCCGCCUGGUA-3' | | 27 |
| Mo | Anp32a | 11737 | 5'-CAAUAGGCCGCUGAAGAA-3' | | 28 |
| Mo | Cyb5r3 | 109754 | 5'-CCAAUGGGCUACUGUGUCUA-3' | | 29 |
| Mo | Numa1 | 101706 | 5'-GGACGGCCAUUCUCUAGUA-3' | | 30 |
| Mo | Set | 56086 | 5'-GGAAGATATTGATGAAGAA-3' | | 31 |
| Mo | Wdr77 | 70465 | 5'-GGGUGUCACUAGACUGGUA-3' | | 32 |
| Mo | Asf1a | 66403 | 5'-AAUCUACAGUCCCUCUUU-3' | | |

TABLE 1-continued

| | | Sequences | |
|---|---|---|---|
| Mo | TBK1 | 56480 5'-CAGACUAGCUUAUAAUGAA-3' | 33 |
| Mo | Mtmr3 | 74302 5'-GGGAAGAGGUCCCUGCUAU-3' | 34 |
| Mo | Sting | 72512 5'-GGAUCCGAAUGUUCAAUCA-3' | 35 |
| Mo | RIG-I | 230073 SMARTpool Dharmacon ON-TARGETplus | |
| Mo | Ifnar1 | 15975 Dharmacon siGENOME SMARTpool | |
| Mo | Jak1 | 16451 Dharmacon siGENOME SMARTpool | |

Cloning primers

The following primers were used for cloning into pCW57d-P2A2R:

Abcf1 forward 5'-CATCATGCTAGCGCCGCCACCATGCCGAAGGTCTCCAAG-3' (SEQ ID NO: 36)
Abcf1 reverse 5'-ATGATGACCGGTTCAATCCCGAGGACGTTGAC-3' (SEQ ID NO: 37)
Abcf1-HA reverse 5'-ATGATGACCGGTTCATGCGTCAGGACATCGTAAGGGTATGCATCCCGAGGACGTTGACCA-3' (SEQ ID NO: 38)
Abcf1 rescue forward 5'-CAAAAGAGGTGTTAACACGGTAAAACAGCAGGTGCCGACG-3' (SEQ ID NO: 39)
Abcf1 rescue reverse 5'-GCTGTTGACGTGTTAACACCTCTTTTGTTGCTTTCCGTGCTTG-3' (SEQ ID NO: 40)
Irf3 forward 5'-CATCATGCTAGCGCCGCCACCATGGAAACCCGAAACCGCGGA-3' (SEQ ID NO: 41)
Irf3 reverse 5'-ATGATGACCGGTTCAGATATTTCAGTGGCCTGGAAGT-3' (SEQ ID NO: 42)
Irf3 rescue forward 5'-TCTGACTGATAAATTGGTCAAAGAGTACGTGGGGCAGGTGC-3' (SEQ ID NO: 43)
Irf3 rescue reverse 5'-CACGTACTCTTTGACCAATTTATCAGTCAGAAACCCTCAGGATCG-3' (SEQ ID NO: 44)
Renilla forward 5'-CATCATGCTAGCGCCGCCACCATGACTTCGAAAGTTTATGATCCAGAACAAGGA-3' (SEQ ID NO: 45)
Renilla-HA reverse 5'-ATGATGACCGGTTCATGCGTAATCAGGCACATCGTAAGGGTATGCTTGTTCATTTTGAGAACTCGCTCAACGAAC-3' (SEQ ID NO: 46)

The following primers were used for cloning into pLX301:

Abcf1 forward 5'-CATCATGAATTCGCCGCCACCATGCCGAAGGTCTCCAAG-3' (SEQ ID NO: 47)
Abcf1 reverse 5'-ATGATGCTCGAGTCAATCCCGAGGACGTTGAC-3' (SEQ ID NO: 48)
Abcf1-HA reverse 5'-ATGATGCTCGAGTCATGCGTCAGGACATCGTAAGGGTATGCATCCCGAGGACGTTGACCA-3' (SEQ ID NO: 49)
Sting forward 5'-CATCATGAATTCgccGCCACCatgCCGTAATCAGGCACATCGTAAGGGTATGCATCCCGATGAGGTCAGTGCGGA-3' (SEQ ID NO: 50)
Sting-HA reverse 5'-ATGATGCTCGAGTCAAACTGACTGCTGCAATAATGT-3' (SEQ ID NO: 51)

qPCR primers

| Species | Gene | GeneID | Forward | SEQ ID NO | Reverse | SEQ ID NO |
|---|---|---|---|---|---|---|
| Mo | Gapdh | 14433 | 5'-GGCAAATTCAACGGCACAGT-3' | 52 | 5'-AGATGGTGATGGGCTTCCC-3' | 84 |
| Mo | Ifnb1 | 15977 | 5'-CTGGCTTCCATCATGAACAA-3' | 53 | 5'-AGAGGGCTGTGGTGAGAA-3' | 85 |
| Mo | Cxcl10 | 15945 | 5'-CCAAGTGCTGCCGTCATTTTC-3' | 54 | 5'-GGCTCGCAGGGATGATTTCAA-3' | 86 |
| Mo | Abcf1 | 224742 | 5'-AGAAAGCCCGAGTGTGTTG-3' | 55 | 5'-GCCCCTTGTAGTCGTTGATG-3' | 87 |
| Mo | RIG-I | 230073 | 5'-ACTTGGGTACAACATTGCGAG-3' | 56 | 5'-GTTCACAAGAATCTGGGGTGTC-3' | 88 |
| Mo | IfitI | 15957 | 5'-CTGAGATGTCACTTCACATGGAA-3' | 57 | 5'-GTGCATCCCAATGGGTTCT-3' | 89 |
| Mo | MxI | 17857 | 5'-GACCATAGGGGTCTTGACCAA-3' | 58 | 5'-AGACTTGCTCTTTTCTGAAAAGCC-3' | 90 |
| Mo | Ifih1 | 71586 | 5'-AGATCAACACCTGTGGTAACACC-3' | 59 | 5'-CTCTAGGGCTTCCCACGAACA-3' | 91 |
| Mo | IL6 | 16193 | 5'-TAGTCCTTCCTACCCCAATTTCC-3' | 60 | 5'-TTGGTCCTTAGCCACTCCTTC-3' | 92 |
| Mo | Irf7 | 54123 | 5'-GAGACTTGGCTATTGGGGAG-3' | 61 | 5'-GACCGAAATGCTTCCAGGG-3' | 93 |
| Mo | Dbx58 | 80861 | 5'-GAAAGTGATCTTACCTGTCTGG-3' | 62 | 5'-TTGCCTCTGTCTGTCTACCGTCT-3' | 94 |
| Mo | Isg15 | 100038882 | 5'-CGCCGAGtcatGCCGTAATCAGGCACATCCAACTCCAT-3' | 63 | 5'-TGGAAAGGGTAAGACCGTCCT-3' | 95 |
| Mo | Ifi44 | 99999 | 5'-AACTGACTGCTGCAATAATGT-3' | 64 | 5'-GTAACAGCAGCAATGCCTCTTGT-3' | 96 |

TABLE 1-continued

| | | | Sequences | | |
|---|---|---|---|---|---|
| Mo | StatI | 20846 | 5'-TCACAGTGGTTCGAGCTTCAG-3' | 65 | 5'-GCAAACGAGACATCATAGGCA-3' | 97 |
| Mo | Cc15 | 20304 | 5'-GCTGCTTTGCCTACCTCTCC-3' | 66 | 5'-TCGAGTGACAAACACGACTGC-3' | 98 |
| Mo | Ptpn1 | 19246 | 5'-GGAACTGGGCGGCTATTTACC-3' | 67 | 5'-CAAAAGGGCTGACATCTCGGT-3' | 99 |
| Mo | Tiparp | 99929 | 5'-GCCAGACTGTGTAGTACAGCC-3' | 68 | 5'-GGGTTCCAGTTCCCAATCTTTT-3' | 100 |
| Mo | Ppp6c | 67857 | 5'-CCGCTGGATCTGACAAGTAT-3' | 69 | 5'-ACACTGCTGAACATTCGACT-3' | 101 |
| Mo | Mdp1 | 67881 | 5'-TTGATCTGGATTACACGCCTCTGG-3' | 70 | 5'-CCATCGCTGCTCTTGTGGAAT-3' | 102 |
| Mo | Asb13 | 142688 | 5'-TCCTGGGAGATGTGGGTTTCT-3' | 71 | 5'-AAGGGGTGTGATCGAGTCCA-3' | 103 |
| Mo | Trim56 | 384309 | 5'-AAGACTTCCTCCCAACTCTG-3' | 72 | 5'-GGCAATAGGTATGTAGGCATGG-3' | 104 |
| Mo | Usp49 | 224836 | 5'-AGTTCCGGAATGTTTCCTGA-3' | 73 | 5'-CTCCTTACTGACAACTCTGCG-3' | 105 |
| Mo | Reep4 | 72549 | 5'-GCCTGGTAGTGCTCATATTTGG-3' | 74 | 5'-GCCATGAAGATCGCAAAGACAA-3' | 106 |
| Mo | Cyb5r3 | 109754 | 5'-CAGGGCTTCGTGAATGAGGAG-3' | 75 | 5'-TCCACACATCAGTATCAGCGG-3' | 107 |
| Mo | Numa1 | 101706 | 5'-CCCAAGGGAGGAATAGCTTCT-3' | 76 | 5'-CTCTGCGATGCGGTTCAA-3' | 108 |
| Mo | Wdr77 | 70465 | 5'-CTTGCTGTCTGGATTCAAGC-3' | 77 | 5'-CAACTGTGGTAAGAAGGGAGTG-3' | 109 |
| Mo | Irf3 | 54131 | 5'-GAGAGCCGAACCAGGTTCAG-3' | 78 | 5'-CTTCCAGGTTGACACGTCCG-3' | 110 |
| Mo | Asf1a | 66403 | 5'-GTGGTGCTGATAACCCGTC-3' | 79 | 5'-GGGACCCACTAAAACAGAGTCTA-3' | 111 |
| Mo | Tbk1 | 56480 | 5'-ACTGGTGATCTTCTATGCTGTCA-3' | 80 | 5'-TTTCTGGAAGTCCATACGCATTG-3' | 112 |
| Mo | Mtmr3 | 74302 | 5'-ATGACTCGTTGCTACCTGAC-3' | 81 | 5'-GAACCGGAACCTTCTGTTAC-3' | 113 |
| Mo | sting | 72512 | 5'-GGTCACCGCTCCAAATATGTAG-3' | 82 | 5'-CAGTAGTCCAAGTTCGTGCGA-3' | 114 |
| Mo | Cdc37 | 12539 | 5'-GACTACAGCGTTTGGGATCAC-3' | 83 | 5'-CCCCGGTTCCAGTTCCTCTT-3' | 115 |

SEQ ID NO: 116, human TREX1
GTCATTGCTTTGGGCCATGGGAAGAAACCATTGTGTGCAGGGA
AGGAGGTGGCTCTTGCCCAGGCCTAAACCAGGAAAGCTGGGAAACTG
GGACCCACAGGTGGGCATGAAAGGCCGCAGCAGGGGCTCCAGCAGTG
TGTAAGACCGGAGCTGGTCTGCACCACTGCCTGGTCCTTCCAGCTGC
CTGTCACTGGTATGATGGCCCCGGTGCATTGTGCCACAGCAGGCACAG
CTGTGGATCTGGAAGGCCTCTGGGGTCCCCGGGAGGAGGGAGTGGGT
GTGGGGGAACGGATGGTGTGACGGGGACAGACCAGGCAGGCTGACG
AGCAGGGCGGGCCTGGCCCTGTAGGCGGGCGGGCCCACGCCAAG
TTTCATTCCCGCCATGCTGCCAGCAGAGCGCGGGAGAGTGTGCAGC
CGAGTCACTAGTGCGCAGGCGAGGAGGGCCCAGTCATGTGAAGAGGGAGACCCTC
CAATGGATGCGCCCAGGGAGGGGCCCAGTCATGTGAAGAGGGAGACCCTC
TAAGGGGGCACTAGGGAGGGAGGGCCCACTAAGGAAAACCACTCACCCTC
TCAGACAGTCGAATGTCGTCCCACTAAGGAAAACCACTCACCCTCTC
CAACTTCCTCCTGAAATGCCCTGAGCTCGCACCAGGCAGGATT
GTGCAGGGAAGGCCTGAGATGTGTTCTGCCACCCCACCCACTCCC
CCCCTTCGGATCTTAACACTGGGCACTCACACACCACCCATGCTCCTC
TCCAGGCTCAGCAGGTACGTACCATGGGCTGCCAGGCCCTGC
CCCGGGGCCCCATGCAGACCCTCATCTTTTTCGACATGGAGGCCACTGGC
TTGCCCTTCTCCAGCCCAAGGTCACGGAGCTGCTGCTGGCTGTCAC
AGATGTGCCCTGGAGAGCCCCCCCACCTCTTCAGGGCCCACCTCCCACAGT
TCCTCCACCACCGCGTGTGAGACAAGCTCTCCCTGTGTGGCTCCGG
GGAAGGCCTCGAGCCAGCAGCGAGATCACAGGTCTGAGCAGCAG
TGTGCTGGAGCAGCCATGGCGCCTCAATGTTTGATGACAACCTGGCCAACC
TCCTCCTAGCCTTCCTGCGGCGCTACGACTTCCCCCTCCAAGCAGAGCTGGCTAT
CACAGGTGTGACGGCTGTCTTGAAGTGCTCTTCTTTGTGTGATAGCATCAC
TGCCCTGGAGCCCTGGAGCCAGCGAGCAGCATCTACACTGCCTGTATGGCAGTC
AGGAAGAGCTACAGCCTAGGACAGCATCTACACTGCCTGTATGGGCAGTC
CCCTCCACCACCGCCTACGACTTCCCCGAGGTGATGTCCTGCTCAGCA
TCTGTCAGTGGAGACAGACCACAGCCCTGTGCGGTGGGTGATGCTCACGCC TABLE 1-continued Sequences AGGCCTTTCGGCACCATCAGGCCCATGTATGGGGTCACAGCCTCTGCTAG
GACCAAGCCAAGACCATTCTGTCACAACCACTGCACACCTGGCCCACAA
CCAGGAACACTAGTCCCAGCCTTGGAGAGAGCAGGGGTACCAAGGATCT
TCCTCCAGTGAAGACCCTGGAGCCCTATCCAGGAGGGGCTGCTGGCCC
CACTGGGTCTGCCTGGCCATCCTGACCTTGGCAGTAGCCACACTGTATGGA
CTATCCCTGGCCCACACCTGGGGAGTAGGCCAAGAAGGAAAATCTGACGA
ATAAAGACCCCCGCTGCCCATA SEQ ID NO: 117, mouse TREX1
GTGTGGCTGAGGAGGGAGGGACAGGGCAGACCAAGAATTGATGAGATGAC
TCCTGCTGAGATTGAGATGGCCCCCATGGTAACTGATCTGCCCTGAGGAA
AAACCCTGCCCCTTCTTCGGAATTACCCTGAGTCATAGCTTTGGGCGGGG
GCCGTGGTGGGGCAGGGGTACGTTTGTGCCAAGGAGGCAGCCCTTTTT
AGGAAGGCCTGGATCAAGGACTGGGGGAAAGACAAGAAAAGGCAGAGG
CTCACGGGCACATTTGAATCTAGAGACAACCCAGTTTGAGTTGTCAGTG
TTGGGGCAGTAGTCCATTTTACCAGCCAGCAGGATCACAGATATGGATCT
AGGAGGCCTTTGGGGTGCTGGGAGGGAGGGAGGAGCGTCAGCACGA
GGGCCAGGCCTGGCAGGCTAACAGCAGGGCGGGCCCTGTTCAGGAGGCA
GGCTATGGGTGGACCCAGGCAGTTTTACTTCCTCAGCCACACTGCTGCC
CAGCAGCAGCCCAGCGGAGTGCCTTGCTGCCTGCTTTCTCGGTAAGTGTGG
AGTAAGGTATGGGGTAAGGCAGACAGAGAATAGGGTTCCCTCACCCTGA
AGGTAGTCAGCACTAGGGAGGGGCCTCCCTCAAAAGGCAAATAAGTAG
TGGATCCATCCCACTAGAACAACCCTGCCCCTCCAGCTTCTAGTGGCCCTG
GATAGTACCTTCTGAAGGAAGGGCTGAGCTGCCTTTCTGCACCCACCT
CAGCCCACATTGAGACCTTCTGCTACTCATTACCCCATTCTTCCTCCCCA
GGTTCAGCATGGCTCACAGACCCTGCCCTGCCCTCCATGGTCACATGCAGACCCTC
ATCTTCTTAGACCTGGAAGCCACTGGCCTGCCCTTGCTCTCGGCCCGAAGTC
ACAGAGCTGTGCCTGCTGGCTGTCCACAGACGTGCTCTGGAGAACACTTC
CATTTCTCAGGACATCCACCTCCAGTGCCCAGTGCCCCGTGTGGTGG
ACAAGTCTCTCTGTGCATTGCTCCAGGAAAGCCTGTAGCCTGTGGGCC
AGTGAGATCACAGGTCTGAGCAAAGCTGAGCTGAAGTGAAGCTGAGTA
CAGGGCGTC
AACGCTTCGATGACAACCTGGCCATCCTGCCCTCCCAGCCTTCCTGCAGCGC
CAGCCACAGCCTTGCTGCCTTGTGGCCACACAACCGTGACCGCTATGACTT
TCCTCTGCTCCAGACAGAGTTCCTAGGCTGAGCACTCCCAGTCCCTAG
ATGGTACCTTCTCTGTGTGGACAGCATCGCTCGCCCTAAAGGCCTTGGAACAA
GCTAGCAGCCCCCTCAGGGATGGTTCGAGGAAAAGCTACAGCCTGGGCA
GCATCTACACCGCCCTGCTACTGGCCAAGCACCGACACTCACATACTGCT
GAAGGTGATGTTCTAACCCTGCTGCCTGTCAGTGGAAGCCACAGGC
CCTACTGCAGTGGGTGGACGAACATGCCCGCCCTTTAGCACCGTCAAGC
CCATGTACGGCACTCCGGCTACACCCTGGCCACCTGGAACAACCTAAGGCCACAT
TGGCAGGAGCAGGCACCTAAGAGTCCTCTCCAGAGAAGGTCCCAGAA
GCCCCATCACAGGGAATATGGGAAATATAAAGACTTCCATAGCACTGAC
GACCTTGGCAATAGCCACTCGTATGGACTCTTCCGGCCTCACCTGGGCA
GTAAGTCAAGAGGGGAATATGATGAAATAAAGACTTCCATAGCACTGAC

What is claimed is:

1. A method of treatment comprising administering to a subject identified as having an overactive DNA sensing pathway an effective amount of at least one active agent, said agent comprising: an ABCF1 inhibitor selected from the group consisting of ABCF1 antibodies or fragments thereof, antisense oligonucleotides, siRNAs; and a combination thereof.

2. The method of claim 1, wherein the subject, identified as having an overactive DNA sensing pathway, has an aberrant expression level of a DNA sensing pathway marker and/or has an aberrant DNA sensing pathway marker.

3. The method of claim 2, further comprising measuring the presence of a DNA sensing pathway marker and/or the expression level of a DNA sensing pathway marker in the subject before administering the effective amount of an active agent.

4. The method of claim 2, wherein the DNA sensing pathway marker is an interferon-stimulated gene (ISG), a Dnase1 mutation, a Dnase2 mutation, a Fen1 (DnaseIV) mutation, a RnaseH2 mutation, or an SAMHD1 mutation.

5. The method of claim 4, wherein the aberrant expression level of a DNA sensing pathway marker is aberrant interferon-stimulated gene (ISG) expression, and the aberrant DNA sensing pathway marker is a Dnase1 mutation, a Dnase2 mutation, a Fen1 (DnaseIV) mutation, a RnaseH2 mutation, or an SAMHD1 mutation.

6. The method of claim 1, wherein the subject identified as having an overactive DNA sensing pathway has an autoimmune disease.

7. The method of claim 6, wherein the active agent is administered prior to the onset of symptoms associated with an autoimmune disorder.

8. The method of claim 6, wherein the subject has Aicardi-Goutieres syndrome (AGS).

9. A method of modulating an innate immune response by targeting the DNA sensing pathway comprising: administering to a subject, identified as having an overactive DNA sensing pathway, an effective amount of an active agent comprising an ABCF1 inhibitor, wherein the ABCF1 inhibitor is selected from the group consisting of ABCF1 antibodies or fragments thereof, antisense oligonucleotides, siRNAs; and a combination thereof.

10. The method of claim 9, wherein the subject, identified as having an overactive DNA sensing pathway, has an aberrant expression level of a DNA sensing pathway marker and/or has an aberrant DNA sensing pathway marker.

11. The method of claim 10, further comprising measuring the presence of a DNA sensing pathway marker and/or the expression level of a DNA sensing pathway marker in the subject before administering the effective amount of an active agent.

12. The method of claim 10, wherein the DNA sensing pathway marker is an interferon-stimulated gene (ISG), a Dnase1 mutation, a Dnase2 mutation, a Fen1 (DnaseIV) mutation, a RnaseH2 mutation, or an SAMHD1 mutation.

13. The method of claim 12, wherein the aberrant expression level of a DNA sensing pathway marker is aberrant interferon-stimulated gene (ISG) expression, and the aberrant DNA sensing pathway marker is a Dnase1 mutation, a Dnase2 mutation, a Fen1 (DnaseIV) mutation, a RnaseH2 mutation, or an SAMHD1 mutation.

14. The method of any one of claims 1, 2-5, 6-8, and 9-13, wherein the ABCF1 inhibitor comprises siRNA.

15. The method of claim 9, wherein the subject identified as having an overactive DNA sensing pathway has an autoimmune disease.

16. The method of claim 15, wherein the active agent is administered prior to the onset of symptoms associated with an autoimmune disorder.

17. The method of claim 15, wherein the subject has Aicardi-Goutieres syndrome (AGS).

18. The method of any one of claims 15-17, wherein the ABCF1 inhibitor comprises siRNA.

19. The method of any one of claims 1, 2-5, 6-8, 9-13 and 15-17 wherein the ABCF1 inhibitor comprises ABCF1 antibodies or fragments thereof.

20. The method of any one of claims 1, 2-5, 6-8, 9-13 and 15-17 wherein the ABCF1 inhibitor comprises antisense oligonucleotides.

* * * * *

SEQUENCE LISTING

<160> NUMBER OF SEQ ID NOS: 117

<210> SEQ ID NO 1
<211> LENGTH: 45
<212> TYPE: DNA
<213> ORGANISM: Artificial Sequence
<220> FEATURE:
<223> OTHER INFORMATION: Synthetic polynucleotide

<400> SEQUENCE: 1
tacagatcta ctagtgatct atgactgatc tgtacatgat ctaca            45

<210> SEQ ID NO 2
<211> LENGTH: 45
<212> TYPE: DNA
<213> ORGANISM: Artificial Sequence
<220> FEATURE:
<223> OTHER INFORMATION: Synthetic polynucleotide

<400> SEQUENCE: 2
tgtagatcat gtacagatca gtcatagatc actagtagat ctgta            45

<210> SEQ ID NO 3
<211> LENGTH: 99
<212> TYPE: DNA
<213> ORGANISM: Artificial Sequence
<220> FEATURE:
<223> OTHER INFORMATION: Synthetic polynucleotide

<400> SEQUENCE: 3
atggttgtag ctgtcccaat atttgtctac agccttctga tgtctctaaa agaccaggat    60
taactgcgaa tcgttctagc tccctgctta cccatacta                          99

<210> SEQ ID NO 4
<211> LENGTH: 100
<212> TYPE: DNA
<213> ORGANISM: Artificial Sequence
<220> FEATURE:
<223> OTHER INFORMATION: Synthetic polynucleotide

<400> SEQUENCE: 4
atagtatggg taagcaggga gctagaacga ttcgcagtta atcctggtct tttagagaca    60
tcagaaggct gtagacaaat attgggacag ctacaaccat                        100

<210> SEQ ID NO 5
<211> LENGTH: 60
<212> TYPE: DNA
<213> ORGANISM: Artificial Sequence
<220> FEATURE:
<223> OTHER INFORMATION: Synthetic polynucleotide

<400> SEQUENCE: 5
taagacacga tgcgataaaa tctgtttgta aaatttatta agggtacaaa ttgccctagc    60

<210> SEQ ID NO 6
<211> LENGTH: 60
<212> TYPE: DNA
<213> ORGANISM: Artificial Sequence
<220> FEATURE:
<223> OTHER INFORMATION: Synthetic polynucleotide

<400> SEQUENCE: 6
gctagggcaa tttgtaccct taataaattt tacaaacaga ttttatcgca tcgtgtctta    60

```
<210> SEQ ID NO 7
<211> LENGTH: 45
<212> TYPE: DNA
<213> ORGANISM: Artificial Sequence
<220> FEATURE:
<223> OTHER INFORMATION: Synthetic polynucleotide

<400> SEQUENCE: 7
tacagatcta ctagtgatct atgactgatc tgtacatgat ctaca          45

<210> SEQ ID NO 8
<211> LENGTH: 45
<212> TYPE: DNA
<213> ORGANISM: Artificial Sequence
<220> FEATURE:
<223> OTHER INFORMATION: Synthetic polynucleotide

<400> SEQUENCE: 8
tgtagatcat gtacagatca gtcatagatc actagtagat ctgta          45

<210> SEQ ID NO 9
<211> LENGTH: 45
<212> TYPE: DNA
<213> ORGANISM: Artificial Sequence
<220> FEATURE:
<223> OTHER INFORMATION: Synthetic polynucleotide

<400> SEQUENCE: 9
tgaagtcatg tgtgatatca cactgcatgt ggctagactt catgg          45

<210> SEQ ID NO 10
<211> LENGTH: 45
<212> TYPE: DNA
<213> ORGANISM: Artificial Sequence
<220> FEATURE:
<223> OTHER INFORMATION: Synthetic polynucleotide

<400> SEQUENCE: 10
ccatgaagtc tagccacatg cagtgtgata tcacacatga cttca          45

<210> SEQ ID NO 11
<211> LENGTH: 45
<212> TYPE: DNA
<213> ORGANISM: Artificial Sequence
<220> FEATURE:
<223> OTHER INFORMATION: Synthetic polynucleotide

<400> SEQUENCE: 11
gtggctccat cctggcctca ctgtccacct tccagcagat gtgga          45

<210> SEQ ID NO 12
<211> LENGTH: 45
<212> TYPE: DNA
<213> ORGANISM: Artificial Sequence
<220> FEATURE:
<223> OTHER INFORMATION: Synthetic polynucleotide

<400> SEQUENCE: 12
tccacatctg ctggaaggtg gacagtgagg ccaggatgga gccac          45

<210> SEQ ID NO 13
<211> LENGTH: 99
<212> TYPE: DNA
<213> ORGANISM: Artificial Sequence
<220> FEATURE:
<223> OTHER INFORMATION: Synthetic polynucleotide
```

```
<400> SEQUENCE: 13
atggttgtag ctgtcccaat atttgtctac agccttctga tgtctctaaa agaccaggat    60
taactgcgaa tcgttctagc tccctgctta cccatacta                           99

<210> SEQ ID NO 14
<211> LENGTH: 100
<212> TYPE: DNA
<213> ORGANISM: Artificial Sequence
<220> FEATURE:
<223> OTHER INFORMATION: Synthetic polynucleotide

<400> SEQUENCE: 14
atagtatggg taagcaggga gctagaacga ttcgcagtta atcctggtct tttagagaca    60
tcagaaggct gtagacaaat attgggacag ctacaaccat                          100

<210> SEQ ID NO 15
<211> LENGTH: 19
<212> TYPE: RNA
<213> ORGANISM: Artificial Sequence
<220> FEATURE:
<223> OTHER INFORMATION: Synthetic polynucleotide

<400> SEQUENCE: 15
aggaaguccu gacucgaaa                                                 19

<210> SEQ ID NO 16
<211> LENGTH: 19
<212> TYPE: DNA
<213> ORGANISM: Artificial Sequence
<220> FEATURE:
<223> OTHER INFORMATION: Synthetic polynucleotide

<400> SEQUENCE: 16
cgatgatagt gatgagaga                                                 19

<210> SEQ ID NO 17
<211> LENGTH: 19
<212> TYPE: RNA
<213> ORGANISM: Artificial Sequence
<220> FEATURE:
<223> OTHER INFORMATION: Synthetic polynucleotide

<400> SEQUENCE: 17
cggacaagcu ugugaagga                                                 19

<210> SEQ ID NO 18
<211> LENGTH: 19
<212> TYPE: RNA
<213> ORGANISM: Artificial Sequence
<220> FEATURE:
<223> OTHER INFORMATION: Synthetic polynucleotide

<400> SEQUENCE: 18
gcgccaagcu gcgaauaga                                                 19

<210> SEQ ID NO 19
<211> LENGTH: 19
<212> TYPE: RNA
<213> ORGANISM: Artificial Sequence
<220> FEATURE:
<223> OTHER INFORMATION: Synthetic polynucleotide

<400> SEQUENCE: 19
gaccacaguc ggauuaaau                                                 19
```

```
<210> SEQ ID NO 20
<211> LENGTH: 19
<212> TYPE: RNA
<213> ORGANISM: Artificial Sequence
<220> FEATURE:
<223> OTHER INFORMATION: Synthetic polynucleotide

<400> SEQUENCE: 20
gaaacaucac accguauug                                                19

<210> SEQ ID NO 21
<211> LENGTH: 19
<212> TYPE: RNA
<213> ORGANISM: Artificial Sequence
<220> FEATURE:
<223> OTHER INFORMATION: Synthetic polynucleotide

<400> SEQUENCE: 21
aacguuaacu caaggauua                                                19

<210> SEQ ID NO 22
<211> LENGTH: 19
<212> TYPE: RNA
<213> ORGANISM: Artificial Sequence
<220> FEATURE:
<223> OTHER INFORMATION: Synthetic polynucleotide

<400> SEQUENCE: 22
gcacgaaggc uauaaguuu                                                19

<210> SEQ ID NO 23
<211> LENGTH: 19
<212> TYPE: RNA
<213> ORGANISM: Artificial Sequence
<220> FEATURE:
<223> OTHER INFORMATION: Synthetic polynucleotide

<400> SEQUENCE: 23
uagagaaagu cgccaaguu                                                19

<210> SEQ ID NO 24
<211> LENGTH: 19
<212> TYPE: RNA
<213> ORGANISM: Artificial Sequence
<220> FEATURE:
<223> OTHER INFORMATION: Synthetic polynucleotide

<400> SEQUENCE: 24
gaagccaacu ugcgcucug                                                19

<210> SEQ ID NO 25
<211> LENGTH: 19
<212> TYPE: RNA
<213> ORGANISM: Artificial Sequence
<220> FEATURE:
<223> OTHER INFORMATION: Synthetic polynucleotide

<400> SEQUENCE: 25
gaccugaagu ugcugagaa                                                19

<210> SEQ ID NO 26
<211> LENGTH: 19
<212> TYPE: RNA
<213> ORGANISM: Artificial Sequence
<220> FEATURE:
```

```
<223> OTHER INFORMATION: Synthetic polynucleotide

<400> SEQUENCE: 26
gaugaucugu cgccuggua                                                    19

<210> SEQ ID NO 27
<211> LENGTH: 19
<212> TYPE: DNA
<213> ORGANISM: Artificial Sequence
<220> FEATURE:
<223> OTHER INFORMATION: Synthetic polynucleotide

<400> SEQUENCE: 27
caatagagcc gctgaagaa                                                    19

<210> SEQ ID NO 28
<211> LENGTH: 19
<212> TYPE: RNA
<213> ORGANISM: Artificial Sequence
<220> FEATURE:
<223> OTHER INFORMATION: Synthetic polynucleotide

<400> SEQUENCE: 28 ccaugggcu acuggucua                                                     19

<210> SEQ ID NO 29
<211> LENGTH: 19
<212> TYPE: RNA
<213> ORGANISM: Artificial Sequence
<220> FEATURE:
<223> OTHER INFORMATION: Synthetic polynucleotide

<400> SEQUENCE: 29
ggacggccau ucucuagua                                                    19

<210> SEQ ID NO 30
<211> LENGTH: 19
<212> TYPE: DNA
<213> ORGANISM: Artificial Sequence
<220> FEATURE:
<223> OTHER INFORMATION: Synthetic polynucleotide

<400> SEQUENCE: 30
ggaagatatt gatgaagaa                                                    19

<210> SEQ ID NO 31
<211> LENGTH: 19
<212> TYPE: RNA
<213> ORGANISM: Artificial Sequence
<220> FEATURE:
<223> OTHER INFORMATION: Synthetic polynucleotide

<400> SEQUENCE: 31
gggugucacu agacuggua                                                    19

<210> SEQ ID NO 32
<211> LENGTH: 19
<212> TYPE: RNA
<213> ORGANISM: Artificial Sequence
<220> FEATURE:
<223> OTHER INFORMATION: Synthetic polynucleotide

<400> SEQUENCE: 32
aaucuacagu cccuucuuu                                                    19
```

```
<210> SEQ ID NO 33
<211> LENGTH: 19
<212> TYPE: RNA
<213> ORGANISM: Artificial Sequence
<220> FEATURE:
<223> OTHER INFORMATION: Synthetic polynucleotide

<400> SEQUENCE: 33
cagacuagcu uauaaugaa                                               19

<210> SEQ ID NO 34
<211> LENGTH: 19
<212> TYPE: RNA
<213> ORGANISM: Artificial Sequence
<220> FEATURE:
<223> OTHER INFORMATION: Synthetic polynucleotide

<400> SEQUENCE: 34
gggaagaggu gccugcuau                                               19

<210> SEQ ID NO 35
<211> LENGTH: 19
<212> TYPE: RNA
<213> ORGANISM: Artificial Sequence
<220> FEATURE:
<223> OTHER INFORMATION: Synthetic polynucleotide

<400> SEQUENCE: 35
ggauccgaau guucaauca                                               19

<210> SEQ ID NO 36
<211> LENGTH: 39
<212> TYPE: DNA
<213> ORGANISM: Artificial Sequence
<220> FEATURE:
<223> OTHER INFORMATION: Synthetic polynucleotide

<400> SEQUENCE: 36
catcatgcta gcgccgccac catgccgaag ggtcccaag                         39

<210> SEQ ID NO 37
<211> LENGTH: 33
<212> TYPE: DNA
<213> ORGANISM: Artificial Sequence
<220> FEATURE:
<223> OTHER INFORMATION: Synthetic polynucleotide

<400> SEQUENCE: 37
atgatgaccg gttcaatccc gaggacggtt gac                               33

<210> SEQ ID NO 38
<211> LENGTH: 65
<212> TYPE: DNA
<213> ORGANISM: Artificial Sequence
<220> FEATURE:
<223> OTHER INFORMATION: Synthetic polynucleotide

<400> SEQUENCE: 38
atgatgaccg gttcatgcgt aatcaggcac atcgtaaggg tatgcatccc gaggacggtt  60
gacca                                                              65

<210> SEQ ID NO 39
<211> LENGTH: 40
<212> TYPE: DNA
<213> ORGANISM: Artificial Sequence
<220> FEATURE:
```

<223> OTHER INFORMATION: Synthetic polynucleotide

<400> SEQUENCE: 39
caaaagaggt gttaacacgt aaacagcaga agtgccgacg                                40

<210> SEQ ID NO 40
<211> LENGTH: 47
<212> TYPE: DNA
<213> ORGANISM: Artificial Sequence
<220> FEATURE:
<223> OTHER INFORMATION: Synthetic polynucleotide

<400> SEQUENCE: 40
gctgtttacg tgttaacacc tcttttgttt gcttttccgc ttgcttg                        47

<210> SEQ ID NO 41
<211> LENGTH: 43
<212> TYPE: DNA
<213> ORGANISM: Artificial Sequence
<220> FEATURE:
<223> OTHER INFORMATION: Synthetic polynucleotide

<400> SEQUENCE: 41
catcatgcta gcgccgccac catggaaacc ccgaaaccgc gga                            43

<210> SEQ ID NO 42
<211> LENGTH: 38
<212> TYPE: DNA
<213> ORGANISM: Artificial Sequence
<220> FEATURE:
<223> OTHER INFORMATION: Synthetic polynucleotide

<400> SEQUENCE: 42
atgatgaccg gttcagatat ttccagtggc ctggaagt                                  38

<210> SEQ ID NO 43
<211> LENGTH: 41
<212> TYPE: DNA
<213> ORGANISM: Artificial Sequence
<220> FEATURE:
<223> OTHER INFORMATION: Synthetic polynucleotide

<400> SEQUENCE: 43
tctgactgat aaattggtca aagagtacgt ggggcaggtg c                              41

<210> SEQ ID NO 44
<211> LENGTH: 46
<212> TYPE: DNA
<213> ORGANISM: Artificial Sequence
<220> FEATURE:
<223> OTHER INFORMATION: Synthetic polynucleotide

<400> SEQUENCE: 44
cacgtactct tgaccaatt tatcagtcag aaacccctca ggatcg                          46

<210> SEQ ID NO 45
<211> LENGTH: 55
<212> TYPE: DNA
<213> ORGANISM: Artificial Sequence
<220> FEATURE:
<223> OTHER INFORMATION: Synthetic polynucleotide

<400> SEQUENCE: 45
catcatgcta gcgccgccac catgacttcg aaagtttatg atccagaaca aagga               55

```
<210> SEQ ID NO 46
<211> LENGTH: 76
<212> TYPE: DNA
<213> ORGANISM: Artificial Sequence
<220> FEATURE:
<223> OTHER INFORMATION: Synthetic polynucleotide

<400> SEQUENCE: 46
atgatgaccg gttcatgcgt aatcaggcac atcgtaaggg tatgcttgtt cattttgag      60 aactcgctca acgaac                                                     76

<210> SEQ ID NO 47
<211> LENGTH: 39
<212> TYPE: DNA
<213> ORGANISM: Artificial Sequence
<220> FEATURE:
<223> OTHER INFORMATION: Synthetic polynucleotide

<400> SEQUENCE: 47
catcatgaat tcgccgccac catgccgaag ggtcccaag                             39

<210> SEQ ID NO 48
<211> LENGTH: 33
<212> TYPE: DNA
<213> ORGANISM: Artificial Sequence
<220> FEATURE:
<223> OTHER INFORMATION: Synthetic polynucleotide

<400> SEQUENCE: 48
atgatgctcg agtcaatccc gaggacggtt gac                                  33

<210> SEQ ID NO 49
<211> LENGTH: 65
<212> TYPE: DNA
<213> ORGANISM: Artificial Sequence
<220> FEATURE:
<223> OTHER INFORMATION: Synthetic polynucleotide

<400> SEQUENCE: 49
atgatgctcg agtcatgcgt aatcaggcac atcgtaaggg tatgcatccc gaggacggtt     60
gacca                                                                 65

<210> SEQ ID NO 50
<211> LENGTH: 43
<212> TYPE: DNA
<213> ORGANISM: Artificial Sequence
<220> FEATURE:
<223> OTHER INFORMATION: Synthetic polynucleotide

<400> SEQUENCE: 50
catcatgaat tcgccgccac catgccatac tccaacctgc atc                       43

<210> SEQ ID NO 51
<211> LENGTH: 62
<212> TYPE: DNA
<213> ORGANISM: Artificial Sequence
<220> FEATURE:
<223> OTHER INFORMATION: Synthetic polynucleotide

<400> SEQUENCE: 51
atgatgctcg agtcatgcgt aatcaggcac atcgtaaggg tatgcgatga ggtcagtgcg     60
ga                                                                    62

<210> SEQ ID NO 52
```

<210> SEQ ID NO 52
<211> LENGTH: 20
<212> TYPE: DNA
<213> ORGANISM: Artificial Sequence
<220> FEATURE:
<223> OTHER INFORMATION: Synthetic polynucleotide

<400> SEQUENCE: 52
ggcaaattca acggcacagt                                              20

<210> SEQ ID NO 53
<211> LENGTH: 20
<212> TYPE: DNA
<213> ORGANISM: Artificial Sequence
<220> FEATURE:
<223> OTHER INFORMATION: Synthetic polynucleotide

<400> SEQUENCE: 53
ctggcttcca tcatgaacaa                                              20

<210> SEQ ID NO 54
<211> LENGTH: 21
<212> TYPE: DNA
<213> ORGANISM: Artificial Sequence
<220> FEATURE:
<223> OTHER INFORMATION: Synthetic polynucleotide

<400> SEQUENCE: 54
ccaagtgctg ccgtcatttt c                                            21

<210> SEQ ID NO 55
<211> LENGTH: 21
<212> TYPE: DNA
<213> ORGANISM: Artificial Sequence
<220> FEATURE:
<223> OTHER INFORMATION: Synthetic polynucleotide

<400> SEQUENCE: 55
agaaagcccg agttgtgttt g                                            21

<210> SEQ ID NO 56
<211> LENGTH: 21
<212> TYPE: DNA
<213> ORGANISM: Artificial Sequence
<220> FEATURE:
<223> OTHER INFORMATION: Synthetic polynucleotide

<400> SEQUENCE: 56
acttgggtac aacattgcga g                                            21

<210> SEQ ID NO 57
<211> LENGTH: 23
<212> TYPE: DNA
<213> ORGANISM: Artificial Sequence
<220> FEATURE:
<223> OTHER INFORMATION: Synthetic polynucleotide

<400> SEQUENCE: 57
ctgagatgtc acttcacatg gaa                                          23

<210> SEQ ID NO 58
<211> LENGTH: 21
<212> TYPE: DNA
<213> ORGANISM: Artificial Sequence
<220> FEATURE:
<223> OTHER INFORMATION: Synthetic polynucleotide

<400> SEQUENCE: 58

```
gaccataggg gtcttgacca a                                              21

<210> SEQ ID NO 59
<211> LENGTH: 23
<212> TYPE: DNA
<213> ORGANISM: Artificial Sequence
<220> FEATURE:
<223> OTHER INFORMATION: Synthetic polynucleotide

<400> SEQUENCE: 59
agatcaacac ctgtggtaac acc                                            23

<210> SEQ ID NO 60
<211> LENGTH: 23
<212> TYPE: DNA
<213> ORGANISM: Artificial Sequence
<220> FEATURE:
<223> OTHER INFORMATION: Synthetic polynucleotide

<400> SEQUENCE: 60
tagtccttcc taccccaatt tcc                                            23

<210> SEQ ID NO 61
<211> LENGTH: 20
<212> TYPE: DNA
<213> ORGANISM: Artificial Sequence
<220> FEATURE:
<223> OTHER INFORMATION: Synthetic polynucleotide

<400> SEQUENCE: 61
gagactggct attgggggag                                                20

<210> SEQ ID NO 62
<211> LENGTH: 23
<212> TYPE: DNA
<213> ORGANISM: Artificial Sequence
<220> FEATURE:
<223> OTHER INFORMATION: Synthetic polynucleotide

<400> SEQUENCE: 62
ggaagtgatc ttacctgctc tgg                                            23

<210> SEQ ID NO 63
<211> LENGTH: 21
<212> TYPE: DNA
<213> ORGANISM: Artificial Sequence
<220> FEATURE:
<223> OTHER INFORMATION: Synthetic polynucleotide

<400> SEQUENCE: 63
ggtgtccgtg actaactcca t                                              21

<210> SEQ ID NO 64
<211> LENGTH: 22
<212> TYPE: DNA
<213> ORGANISM: Artificial Sequence
<220> FEATURE:
<223> OTHER INFORMATION: Synthetic polynucleotide

<400> SEQUENCE: 64
aactgactgc tcgcaataat gt                                             22

<210> SEQ ID NO 65
<211> LENGTH: 21
<212> TYPE: DNA
```

<213> ORGANISM: Artificial Sequence
<220> FEATURE:
<223> OTHER INFORMATION: Synthetic polynucleotide

<400> SEQUENCE: 65
tcacagtggt tcgagcttca g                                      21

<210> SEQ ID NO 66
<211> LENGTH: 20
<212> TYPE: DNA
<213> ORGANISM: Artificial Sequence
<220> FEATURE:
<223> OTHER INFORMATION: Synthetic polynucleotide

<400> SEQUENCE: 66
gctgctttgc ctacctctcc                                        20

<210> SEQ ID NO 67
<211> LENGTH: 21
<212> TYPE: DNA
<213> ORGANISM: Artificial Sequence
<220> FEATURE:
<223> OTHER INFORMATION: Synthetic polynucleotide

<400> SEQUENCE: 67
ggaactgggc ggctatttac c                                      21

<210> SEQ ID NO 68
<211> LENGTH: 21
<212> TYPE: DNA
<213> ORGANISM: Artificial Sequence
<220> FEATURE:
<223> OTHER INFORMATION: Synthetic polynucleotide

<400> SEQUENCE: 68
gccagactgt gtagtacagc c                                      21

<210> SEQ ID NO 69
<211> LENGTH: 21
<212> TYPE: DNA
<213> ORGANISM: Artificial Sequence
<220> FEATURE:
<223> OTHER INFORMATION: Synthetic polynucleotide

<400> SEQUENCE: 69
ccgctggatc tggacaagta t                                      21

<210> SEQ ID NO 70
<211> LENGTH: 23
<212> TYPE: DNA
<213> ORGANISM: Artificial Sequence
<220> FEATURE:
<223> OTHER INFORMATION: Synthetic polynucleotide

<400> SEQUENCE: 70
ttgatctgga ttacacgctc tgg                                    23

<210> SEQ ID NO 71
<211> LENGTH: 21
<212> TYPE: DNA
<213> ORGANISM: Artificial Sequence
<220> FEATURE:
<223> OTHER INFORMATION: Synthetic polynucleotide

<400> SEQUENCE: 71
tcctgggaga tgtgggtttc t                                      21

<210> SEQ ID NO 72
<211> LENGTH: 20
<212> TYPE: DNA
<213> ORGANISM: Artificial Sequence
<220> FEATURE:
<223> OTHER INFORMATION: Synthetic polynucleotide

<400> SEQUENCE: 72
aagactcctc cccaactctg					20

<210> SEQ ID NO 73
<211> LENGTH: 21
<212> TYPE: DNA
<213> ORGANISM: Artificial Sequence
<220> FEATURE:
<223> OTHER INFORMATION: Synthetic polynucleotide

<400> SEQUENCE: 73
agttccggga atgtttcctg a					21

<210> SEQ ID NO 74
<211> LENGTH: 22
<212> TYPE: DNA
<213> ORGANISM: Artificial Sequence
<220> FEATURE:
<223> OTHER INFORMATION: Synthetic polynucleotide

<400> SEQUENCE: 74
gcctggtagt gctcatattt gg				22

<210> SEQ ID NO 75
<211> LENGTH: 21
<212> TYPE: DNA
<213> ORGANISM: Artificial Sequence
<220> FEATURE:
<223> OTHER INFORMATION: Synthetic polynucleotide

<400> SEQUENCE: 75
cagggcttcg tgaatgagga g					21

<210> SEQ ID NO 76
<211> LENGTH: 21
<212> TYPE: DNA
<213> ORGANISM: Artificial Sequence
<220> FEATURE:
<223> OTHER INFORMATION: Synthetic polynucleotide

<400> SEQUENCE: 76
cccaagggag gaatagcttc t					21

<210> SEQ ID NO 77
<211> LENGTH: 21
<212> TYPE: DNA
<213> ORGANISM: Artificial Sequence
<220> FEATURE:
<223> OTHER INFORMATION: Synthetic polynucleotide

<400> SEQUENCE: 77
cttgctgtgc tggattcaag c					21

<210> SEQ ID NO 78
<211> LENGTH: 20
<212> TYPE: DNA
<213> ORGANISM: Artificial Sequence
<220> FEATURE:

<223> OTHER INFORMATION: Synthetic polynucleotide

<400> SEQUENCE: 78
gagagccgaa cgaggttcag                                               20

<210> SEQ ID NO 79
<211> LENGTH: 20
<212> TYPE: DNA
<213> ORGANISM: Artificial Sequence
<220> FEATURE:
<223> OTHER INFORMATION: Synthetic polynucleotide

<400> SEQUENCE: 79
gtggtgctgg ataacccgtc                                               20

<210> SEQ ID NO 80
<211> LENGTH: 22
<212> TYPE: DNA
<213> ORGANISM: Artificial Sequence
<220> FEATURE:
<223> OTHER INFORMATION: Synthetic polynucleotide

<400> SEQUENCE: 80
actggtgatc tctatgctgt ca                                            22

<210> SEQ ID NO 81
<211> LENGTH: 21
<212> TYPE: DNA
<213> ORGANISM: Artificial Sequence
<220> FEATURE:
<223> OTHER INFORMATION: Synthetic polynucleotide

<400> SEQUENCE: 81
atgactcgtt ggctacctga c                                             21

<210> SEQ ID NO 82
<211> LENGTH: 22
<212> TYPE: DNA
<213> ORGANISM: Artificial Sequence
<220> FEATURE:
<223> OTHER INFORMATION: Synthetic polynucleotide

<400> SEQUENCE: 82
ggtcaccgct ccaaatatgt ag                                            22

<210> SEQ ID NO 83
<211> LENGTH: 21
<212> TYPE: DNA
<213> ORGANISM: Artificial Sequence
<220> FEATURE:
<223> OTHER INFORMATION: Synthetic polynucleotide

<400> SEQUENCE: 83
gactacagcg tttgggatca c                                             21

<210> SEQ ID NO 84
<211> LENGTH: 19
<212> TYPE: DNA
<213> ORGANISM: Artificial Sequence
<220> FEATURE:
<223> OTHER INFORMATION: Synthetic polynucleotide

<400> SEQUENCE: 84
agatggtgat gggcttccc                                                19

```
<210> SEQ ID NO 85
<211> LENGTH: 19
<212> TYPE: DNA
<213> ORGANISM: Artificial Sequence
<220> FEATURE:
<223> OTHER INFORMATION: Synthetic polynucleotide

<400> SEQUENCE: 85
agagggctgt ggtggagaa                                                    19

<210> SEQ ID NO 86
<211> LENGTH: 21
<212> TYPE: DNA
<213> ORGANISM: Artificial Sequence
<220> FEATURE:
<223> OTHER INFORMATION: Synthetic polynucleotide

<400> SEQUENCE: 86
ggctcgcagg gatgatttca a                                                 21

<210> SEQ ID NO 87
<211> LENGTH: 21
<212> TYPE: DNA
<213> ORGANISM: Artificial Sequence
<220> FEATURE:
<223> OTHER INFORMATION: Synthetic polynucleotide

<400> SEQUENCE: 87
gcccccttgt agtcgttgat g                                                 21

<210> SEQ ID NO 88
<211> LENGTH: 22
<212> TYPE: DNA
<213> ORGANISM: Artificial Sequence
<220> FEATURE:
<223> OTHER INFORMATION: Synthetic polynucleotide

<400> SEQUENCE: 88
gttcacaaga atctggggtg tc                                                22

<210> SEQ ID NO 89
<211> LENGTH: 20
<212> TYPE: DNA
<213> ORGANISM: Artificial Sequence
<220> FEATURE:
<223> OTHER INFORMATION: Synthetic polynucleotide

<400> SEQUENCE: 89
gtgcatcccc aatgggttct                                                   20

<210> SEQ ID NO 90
<211> LENGTH: 23
<212> TYPE: DNA
<213> ORGANISM: Artificial Sequence
<220> FEATURE:
<223> OTHER INFORMATION: Synthetic polynucleotide

<400> SEQUENCE: 90
agacttgctc tttctgaaaa gcc                                               23

<210> SEQ ID NO 91
<211> LENGTH: 20
<212> TYPE: DNA
<213> ORGANISM: Artificial Sequence
<220> FEATURE:
<223> OTHER INFORMATION: Synthetic polynucleotide
```

-continued

<400> SEQUENCE: 91
ctctagggcc tccacgaaca                                                    20

<210> SEQ ID NO 92
<211> LENGTH: 21
<212> TYPE: DNA
<213> ORGANISM: Artificial Sequence
<220> FEATURE:
<223> OTHER INFORMATION: Synthetic polynucleotide

<400> SEQUENCE: 92
ttggtcctta gccactcctt c                                                  21

<210> SEQ ID NO 93
<211> LENGTH: 19
<212> TYPE: DNA
<213> ORGANISM: Artificial Sequence
<220> FEATURE:
<223> OTHER INFORMATION: Synthetic polynucleotide

<400> SEQUENCE: 93
gaccgaaatg cttccaggg                                                     19

<210> SEQ ID NO 94
<211> LENGTH: 21
<212> TYPE: DNA
<213> ORGANISM: Artificial Sequence
<220> FEATURE:
<223> OTHER INFORMATION: Synthetic polynucleotide

<400> SEQUENCE: 94
ttgcctctgt ctaccgtctc t                                                  21

<210> SEQ ID NO 95
<211> LENGTH: 21
<212> TYPE: DNA
<213> ORGANISM: Artificial Sequence
<220> FEATURE:
<223> OTHER INFORMATION: Synthetic polynucleotide

<400> SEQUENCE: 95
tggaaagggt aagaccgtcc t                                                  21

<210> SEQ ID NO 96
<211> LENGTH: 22
<212> TYPE: DNA
<213> ORGANISM: Artificial Sequence
<220> FEATURE:
<223> OTHER INFORMATION: Synthetic polynucleotide

<400> SEQUENCE: 96
gtaacacagc aatgcctctt gt                                                 22

<210> SEQ ID NO 97
<211> LENGTH: 21
<212> TYPE: DNA
<213> ORGANISM: Artificial Sequence
<220> FEATURE:
<223> OTHER INFORMATION: Synthetic polynucleotide

<400> SEQUENCE: 97
gcaaacgaga catcataggc a                                                  21

<210> SEQ ID NO 98
<211> LENGTH: 21

```
<212> TYPE: DNA
<213> ORGANISM: Artificial Sequence
<220> FEATURE:
<223> OTHER INFORMATION: Synthetic polynucleotide

<400> SEQUENCE: 98
tcgagtgaca aacacgactg c                                              21

<210> SEQ ID NO 99
<211> LENGTH: 21
<212> TYPE: DNA
<213> ORGANISM: Artificial Sequence
<220> FEATURE:
<223> OTHER INFORMATION: Synthetic polynucleotide

<400> SEQUENCE: 99
caaaagggct gacatctcgg t                                              21

<210> SEQ ID NO 100
<211> LENGTH: 22
<212> TYPE: DNA
<213> ORGANISM: Artificial Sequence
<220> FEATURE:
<223> OTHER INFORMATION: Synthetic polynucleotide

<400> SEQUENCE: 100
gggttccagt tcccaatctt tt                                             22

<210> SEQ ID NO 101
<211> LENGTH: 21
<212> TYPE: DNA
<213> ORGANISM: Artificial Sequence
<220> FEATURE:
<223> OTHER INFORMATION: Synthetic polynucleotide

<400> SEQUENCE: 101
acactggctg aacattcgac t                                              21

<210> SEQ ID NO 102
<211> LENGTH: 21
<212> TYPE: DNA
<213> ORGANISM: Artificial Sequence
<220> FEATURE:
<223> OTHER INFORMATION: Synthetic polynucleotide

<400> SEQUENCE: 102
ccatcgctgc tcttgtggaa t                                              21

<210> SEQ ID NO 103
<211> LENGTH: 20
<212> TYPE: DNA
<213> ORGANISM: Artificial Sequence
<220> FEATURE:
<223> OTHER INFORMATION: Synthetic polynucleotide

<400> SEQUENCE: 103 aagggggtgtg atcgagtcca                                               20

<210> SEQ ID NO 104
<211> LENGTH: 22
<212> TYPE: DNA
<213> ORGANISM: Artificial Sequence
<220> FEATURE:
<223> OTHER INFORMATION: Synthetic polynucleotide

<400> SEQUENCE: 104
```
ggcaataggt atgtaggcat gg   22

<210> SEQ ID NO 105
<211> LENGTH: 21
<212> TYPE: DNA
<213> ORGANISM: Artificial Sequence
<220> FEATURE:
<223> OTHER INFORMATION: Synthetic polynucleotide

<400> SEQUENCE: 105
ctccttactg acaactctgc g   21

<210> SEQ ID NO 106
<211> LENGTH: 22
<212> TYPE: DNA
<213> ORGANISM: Artificial Sequence
<220> FEATURE:
<223> OTHER INFORMATION: Synthetic polynucleotide

<400> SEQUENCE: 106
gccatgaaga tcgcaaagac aa   22

<210> SEQ ID NO 107
<211> LENGTH: 21
<212> TYPE: DNA
<213> ORGANISM: Artificial Sequence
<220> FEATURE:
<223> OTHER INFORMATION: Synthetic polynucleotide

<400> SEQUENCE: 107
tccacacatc agtatcagcg g   21

<210> SEQ ID NO 108
<211> LENGTH: 19
<212> TYPE: DNA
<213> ORGANISM: Artificial Sequence
<220> FEATURE:
<223> OTHER INFORMATION: Synthetic polynucleotide

<400> SEQUENCE: 108
ctctgcgatg cggttccaa   19

<210> SEQ ID NO 109
<211> LENGTH: 22
<212> TYPE: DNA
<213> ORGANISM: Artificial Sequence
<220> FEATURE:
<223> OTHER INFORMATION: Synthetic polynucleotide

<400> SEQUENCE: 109
caactgtggt aagaagggag tg   22

<210> SEQ ID NO 110
<211> LENGTH: 20
<212> TYPE: DNA
<213> ORGANISM: Artificial Sequence
<220> FEATURE:
<223> OTHER INFORMATION: Synthetic polynucleotide

<400> SEQUENCE: 110
cttccaggtt gacacgtccg   20

<210> SEQ ID NO 111
<211> LENGTH: 23
<212> TYPE: DNA
<213> ORGANISM: Artificial Sequence

```
<220> FEATURE:
<223> OTHER INFORMATION: Synthetic polynucleotide

<400> SEQUENCE: 111
gggacccact aaaacagagt cta                                              23

<210> SEQ ID NO 112
<211> LENGTH: 22
<212> TYPE: DNA
<213> ORGANISM: Artificial Sequence
<220> FEATURE:
<223> OTHER INFORMATION: Synthetic polynucleotide

<400> SEQUENCE: 112
ttctggaagt ccatacgcat tg                                               22

<210> SEQ ID NO 113
<211> LENGTH: 21
<212> TYPE: DNA
<213> ORGANISM: Artificial Sequence
<220> FEATURE:
<223> OTHER INFORMATION: Synthetic polynucleotide

<400> SEQUENCE: 113
gaaccggaac cttctggtta c                                                21

<210> SEQ ID NO 114
<211> LENGTH: 21
<212> TYPE: DNA
<213> ORGANISM: Artificial Sequence
<220> FEATURE:
<223> OTHER INFORMATION: Synthetic polynucleotide

<400> SEQUENCE: 114
cagtagtcca agttcgtgcg a                                                21

<210> SEQ ID NO 115
<211> LENGTH: 19
<212> TYPE: DNA
<213> ORGANISM: Artificial Sequence
<220> FEATURE:
<223> OTHER INFORMATION: Synthetic polynucleotide

<400> SEQUENCE: 115
ccccggtcca gttcctctt                                                   19

<210> SEQ ID NO 116
<211> LENGTH: 1816
<212> TYPE: DNA
<213> ORGANISM: Homo sapiens

<400> SEQUENCE: 116
gtcattgctt tgggctgggg ccatgggaag aaaccattgt gtggcaggga aggaggtggc       60
tcttggccca ggcctaaacc aggaaagcct gggaaactgg gacccacagg tgggcatgaa      120
agggccgcag cagggctcc cagcagtgtg taagaccggg agctggtctg gcaccactgc       180
cctggtcctt ccagctgcct gtcactggta tgatggcccc ggtgcattgt gccaccagca      240
ggccacagct gtggatcttg gaaggcctct ggggtccccc gggagcaggg gagtgggtgt      300
gggggggaac ggatggtggt gagagggaca gaccaggcag gctgacgagc agggcgggcc      360
tggctcacgt gggcctgtag gcgggcccac gccaagtttc acttcccgcc actgctgcca      420
gcgagagccg cgggagagtg tgcagccgag tcactactgc ctgcctgcct gcctgctacg      480
```

```
gtgagtgtgg cccccacaat gggatggcgc agggcaggag ggccatgggt tcccccaccc    540
cagactaagg gggcactagg ggaggggccg agtcatgtga agagggagac cctctcagac    600
agtcgaatgt gctggtccca ctaaggaaac cacctcaccc tctccaactt cctgcctgaa    660
aatgggccct ggagctcgca gacagggcag gattgtgcag ggaaggcctg agatgtgctt    720
ctgcccaccc cctaccccac tccctcccct tcggatctta acactgggca ctcacacacc    780
caccccatgc tcctctccag gctcagcagc aggtacgtac ccaaccatgg gctcgcaggc    840
cctgcccccg gggcccatgc agaccctcat cttttttcgac atggaggcca ctggcttgcc    900
cttctcccag cccaaggtca cggagctgtg cctgctggct gtccacagat gtgccctgga    960 gagcccccc acctctcagg ggccacctcc cacagttcct ccaccaccgc gtgtggtaga    1020
caagctctcc ctgtgtgtgg ctccggggaa ggcctgcagc cctgcagcca gcagatcac    1080 aggtctgagc acagctgtgc tggcagcgca tgggcgtcaa tgttttgatg acaacctggc    1140
caacctgctc ctagccttcc tgcggcgcca gccacagccc tggtgcctgg tggcacacaa    1200
tggtgaccgc tacgacttcc ccctgctcca agcagagctg gctatgctgg gcctcaccag    1260
tgctctggat ggtgccttct gtgtggatag catcactgcg ctgaaggccc tggagcgagc    1320
aagcagcccc tcagaaacacg gcccaaggaa gagctacagc ctaggcagca tctacactcg    1380
cctgtatggg cagtcccctc cagactcgca cacggctgag ggtgatgtcc tggccctgct    1440
cagcatctgt cagtggagac acaggccct gctgcggtgg gtggatgctc acgcaggcc    1500 tttcggcacc atcaggccca tgtatggggt cacagcctct gctaggacca gccaagacc    1560 atctgctgtc acaaccactg cacacctggc acaaccagg aacactagtc ccagccttgg    1620
agagagcagg ggtaccaagg atcttcctcc agtgaaggac cctggagccc tatccaggga    1680
ggggctgctg gccccactgg gtctgctggc catcctgacc ttggcagtag ccacactgta    1740
tggactatcc ctggccacac ctggggagta ggccaagaag gaaaatctga cgaataaaga    1800
cccccgctgc cccata                                                    1816

<210> SEQ ID NO 117
<211> LENGTH: 1792
<212> TYPE: DNA
<213> ORGANISM: Mus musculus

<400> SEQUENCE: 117
gtgtggctga gagggaggga cagggcagac caagaattga tgagatgact cctgctggag     60
ttgagatggc ccccatggta actgatctgc cctgaggaaa aaccctgccc tcttcgggaa    120
attaccctga gtcatagctt tgggcggggg ccgtggtggg ggcagggggta cgtttgtggc    180 caaggaggca gcccttttta ggaaggcctg gatcaaggac tgggggaaag acaagaaaag    240
gcagaggctc acgggcacat ttgaatccta gagacaaccc agtttgagtt gtcagtgttg    300
gggcagtagt ccattttacc agccagcagg atcacagata tggatctagg aaggcctttg    360
gggtgcttgg ggagggaggg aggagcgtca gcacgagggc caggcctggc aggctaacag    420
cagggcgggc cctgttcagg aggcaggcct atgggtggac ccaggcagtt ttacttcctc    480
agccacactg ctgccagcag cagacccagc ggagtgcctt gctgcctgct tctcggtaag    540
tgtggagtaa gggtatgggg taaggcagaa gagaataggg ttccctcacc ctgaaggtag    600
tcagcactag gggaagggcc tccctcaaaa ggcaaataag tagtggatcc atcccactag    660
aacaaccctg ccctccagct tctagtgcc ctggatagta cctgctgaag ggaagggctg    720
agctgccttt ctgcacccca cctcagccca cttgagacct tcctgctgct actcattacc    780
```

-continued

```
ccatctcctc cccaggttca gcatgggctc acagaccctg ccccatggtc acatgcagac    840
cctcatcttc ttagacctgg aagccactgg cctgccttcg tctcggcccg aagtcacaga    900
gctgtgcctg ctggctgtcc acagacgtgc tctggagaac acttccattt ctcagggaca    960
tccacctcca gtgcccagac cgccccgtgt ggtggacaag ctctctctgt gcattgctcc   1020
agggaaagcc tgtagccctg gggccagtga gatcacaggt ctgagcaaag ctgagctgga   1080
agtacagggg cgtcaacgct tcgatgacaa cctggccatc ctgctccgag ccttcctgca   1140
gcgccagcca cagccttgct gccttgtggc acacaacggt gaccgctatg actttcctct   1200
gctccagaca gagcttgcta ggctgagcac tcccagtccc ctagatggta ccttctgtgt   1260
ggacagcatc gctgccctaa aggccttgga acaagctagc agccctcag ggaatggttc    1320 gaggaaaagc tacagcctgg gcagcatcta caccgcctg tactggcaag caccgacaga    1380
ctcacatact gctgaaggtg atgttctaac cctgctcagc atctgtcagt ggaagccaca   1440
ggccctactg cagtgggtgg acgaacatgc ccggcccttt agcaccgtca agcccatgta   1500
cggcactccg gctaccactg gaacaaccaa cctaaggcca catgctgcca cagctactac   1560 accctggcc acagccaatg gaagtccag caatggcagg agcaggcgac ctaagagtcc     1620
tcctccagag aaggtcccag aagccccatc acaggagggg ctgctggccc cactgagcct   1680
gctgaccctc ctgaccttgg caatagccac tctgtatgga ctcttcctgg cctcacctgg   1740
gcagtaagtc aagaggggaa atatgatgaa taaagacttc catagcactg ac           1792
```